United States Patent
Daniel et al.

(10) Patent No.: US 12,165,070 B2
(45) Date of Patent: Dec. 10, 2024

(54) DNA-BASED NEURAL NETWORK

(71) Applicant: TECHNION RESEARCH & DEVELOPMENT FOUNDATION LIMITED, Haifa (IL)

(72) Inventors: Ramez Daniel, Haifa (IL); Loai Danial, Nazareth (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 1384 days.

(21) Appl. No.: 16/626,824

(22) PCT Filed: Jun. 27, 2018

(86) PCT No.: PCT/IL2018/050706
§ 371 (c)(1),
(2) Date: Dec. 26, 2019

(87) PCT Pub. No.: WO2019/003228
PCT Pub. Date: Jan. 3, 2019

(65) Prior Publication Data
US 2020/0143255 A1    May 7, 2020

Related U.S. Application Data

(60) Provisional application No. 62/525,242, filed on Jun. 27, 2017.

(51) Int. Cl.
G06N 3/123 (2023.01)
C12N 15/63 (2006.01)
(Continued)

(52) U.S. Cl.
CPC ............. *G06N 3/123* (2013.01); *C12N 15/63* (2013.01); *G06N 3/048* (2023.01); *G06N 3/065* (2023.01); *C12N 2830/005* (2013.01)

(58) Field of Classification Search
CPC ........ G06N 3/065; G06N 3/123; G06N 3/048; C12N 15/63
See application file for complete search history.

(56) References Cited

U.S. PATENT DOCUMENTS

2017/0183654 A1*  6/2017  Wong ................... G06N 3/002
2017/0255857 A1*  9/2017  Collins ................... H03M 1/74

FOREIGN PATENT DOCUMENTS

| WO | 2011066539 A2 | 6/2011 |
| WO | 2013155439 A1 | 10/2013 |
| WO | 2015188191 A1 | 12/2015 |

OTHER PUBLICATIONS

Rubens, Jacob R., Gianluca Selvaggio, and Timothy K. Lu. "Synthetic mixed-signal computation in living cells." Nature communications 7.1 (2016): 11658. (Year: 2016).*

(Continued)

*Primary Examiner* — Benjamin P Geib
(74) *Attorney, Agent, or Firm* — The Roy Gross Law Firm, LLC; Roy Gross

(57) ABSTRACT

An analog signal processing circuit comprising: a first promoter operably linked to a nucleic acid sequence encoding a first output molecule, wherein said promoter is responsive to a cooperative input signal comprising at least two cooperative inputs, and wherein expression of said at least two cooperative inputs is tunable.

12 Claims, 28 Drawing Sheets
(11 of 28 Drawing Sheet(s) Filed in Color)

(51) Int. Cl.
G06N 3/048 (2023.01)
G06N 3/065 (2023.01)

(56) References Cited

OTHER PUBLICATIONS

Lakin, Matthew R., and Darko Stefanovic. "Supervised learning in an adaptive DNA strand displacement circuit." DNA Computing and Molecular Programming: 21st International Conference, DNA 21, Boston and Cambridge, MA, USA, Aug. 17-21, 2015. Proceedings 21. Springer International Publishing, 2015. (Year: 2015).*
Chen, Sherry Xi, and Georg Seelig. "A DNA neural network constructed from molecular variable gain amplifiers." International Conference on DNA-Based Computers. Cham: Springer International Publishing, 2017. (Year: 2017).*
Keith R. Loeb and L. A. Loeb, "Significance of multiple mutations in cancer", Carcinogenesis vol. 21 Issue 3 pp. 379-385, 2000.
Kenneth R. Foster et al., "Machine learning, medical diagnosis, and biomedical engineering research—commentary", Biomed Eng Online, vol. 13 Issue 1 p. 94, 2014.
Ramiz Daniel et al., "Modeling and Measurement of a Whole-cell Bioluminescent Biosensor Based on a Single Photon Avalanche Diode", Biosensors and Bioelectronics vol. 24 Issue 4 pp. 882-887, 2008.
Jayavardhana Gubbi et al., "Internet of Things (Iot): A vision, architectural elements, and future directions", Future Generation Computer Systems, vol. 29 Issue 7 pp. 1645-1660, 2013.
Frank Rosenblatt, "The Perceptron—A Perceiving and Recognizing Automaton" Report No. 85, pp. 460-461, Cornell Aeronautical Laboratory, Buffalo, New York, 1957.
David J. C. Mackay, "Information Theory, Inference, and Learning Algorithms. Learning", pp. 348-349, University of Cambridge, 2003.
Tae Seok Moon et al., "Genetic programs constructed from layered logic gates in single cells", Nature, vol. 491 Issue 7423 pp. 249-253, 2012.
Luna Rizik et al., "Noise Tolerance Analysis for Reliable Analog and Digital Computation in Living Cells", Journal of Bioengineering and Biomedical Science, vol. 6 Issue 2, 2016.
Dmitri B. Strukov et al., "The missing memristor found", Nature, vol. 453 Issue 7191 pp. 80-83, 2008.
Michael B. Elowitz, Stanislas Leibler, "A synthetic oscillatory network of transcriptional regulators", Nature, vol. 403 Issue 6767 pp. 335-338, 2000.
Timothy S. Gardner et al. "Construction of a genetic toggle switch in *Escherichia coli*", Nature, vol. 403 Issue 6767 pp. 339-342, 2000.
Ron Milo et al., "Network motifs: simple building blocks of complex networks", Science, vol. 298 Issue 5594 pp. 824-827, 2002.

Stefano Cardinale and Adam P. Arkin, "Contextualizing context for synthetic biology—identifying causes of failure of synthetic biological systems", Biotechnology Journal, vol. 7 Issue 7 pp. 856-866, 2012.
Ramiz Daniel et al., "Synthetic analog computation in living cells", Nature, vol. 497 Issue 7451 pp. 619-623, 2013.
Herbert M. Sauro and Kyung Kim, "It's an analog world" Nature, vol. 497 pp. 572-573, 2013.
Ramiz Daniel et al., "Analog transistor models of bacterial genetic circuits", IEEE Biomedical Circuits and Systems Conference, BioCAS, pp. 333-336, 2011.
Piro Siuti et al., "Synthetic circuits integrating logic and memory in living cells", Nature Biotechnology, vol. 31 Issue 5 pp. 448-452, 2013.
Robert Sidney Cox et al., "Programming gene expression with combinatorial promoters", Mol Syst Biol., vol. 3 p. 145, 2007.
Tatenda Shopera et al., "Robust, tunable genetic memory from protein sequestration combined with positive feedback", Nucleic Acids Res. vol. 43 Issue 18 pp. 9086-9094, 2015.
Ligang Gao et al., "Digital-to-analog and analog-to-digital conversion with metal oxide memristors for ultra-low power computing", IEEE/ACM International Symposium on Nanoscale Architectures, NANOARCH, vol. 1 pp. 19-22, 2013.
J. J. Hopfield, "Neural networks and physical systems with emergent collective computational abilities", Proc. Natl. Acad. Sci. USA, vol. 79, pp. 2554-2558, Apr. 1982.
Geoffrey E. Hinton and J. Sejnowski, "Learning and relearning in Boltzmann machines", Parallel Distributed Processing: Explorations in the Microstructure of Cognition. vol. 1 Foundations, MIT Press, Cambridge, MA, 1986.
PCT Search Report for International Application No. PCT/IL2018/050706 mailed on Oct. 22, 2018, 3 pp.
PCT Written Opinion for International Application No. PCT/IL2018/050706 mailed on Oct. 22, 2018, 8 pp.
PCT International Preliminary Report on Patentability or International Application No. PCT/IL2018/050706 issued on Dec. 31, 2019, 9 pp.
Shotaro Ayukawa et al: Construction of a genetic AND gate under a new standard for assembly of genetic parts, BMC Genomics 2010, 11(Suppl 4):S16.
Barbara Jusiak et al: "Synthetic Gene Circuits", In: Encyclopedia of Molecular Cell Biology and Molecular Medicine, Oct. 2014, pp. 1-56.
Jasmine Shong and Cynthia H. Collins: "Quorum Sensing-Modulated AND-Gate Promoters Control Gene Expression in Response to a Combination of Endogenous and Exogenous Signals", ACS Synth. Biol. 2014, 3, 238-246.
Vijai Singh: "Recent advancements in synthetic biology: Current status and challenges", Gene 535 (2014) 1-11.
Jonathan J. Y. Teo et al: "Synthetic Biology: A Unifying View and Review Using Analog Circuits", IEEE Transactions on Biomedical Circuits and Systems, vol. 9, No. 4, Aug. 2015, pp. 453-474.

* cited by examiner

Figure 7B
| A | B | Cin | A·B·Cin | Sum | Cout |
|---|---|---|---|---|---|
| | Digital | | Analog | Digital | |
| 1 | 1 | 1 | 1 | 1 | 1 |
| 1 | 1 | 10 | 10 | 10 | 1 |
| 1 | 10 | 1 | 10 | 10 | 1 |
| 1 | 10 | 10 | 100 | 1 | 10 |
| 10 | 1 | 1 | 10 | 10 | 1 |
| 10 | 1 | 10 | 100 | 1 | 10 |
| 10 | 10 | 1 | 100 | 1 | 10 |
| 10 | 10 | 10 | 1000 | 10 | 10 |
Figure 7C
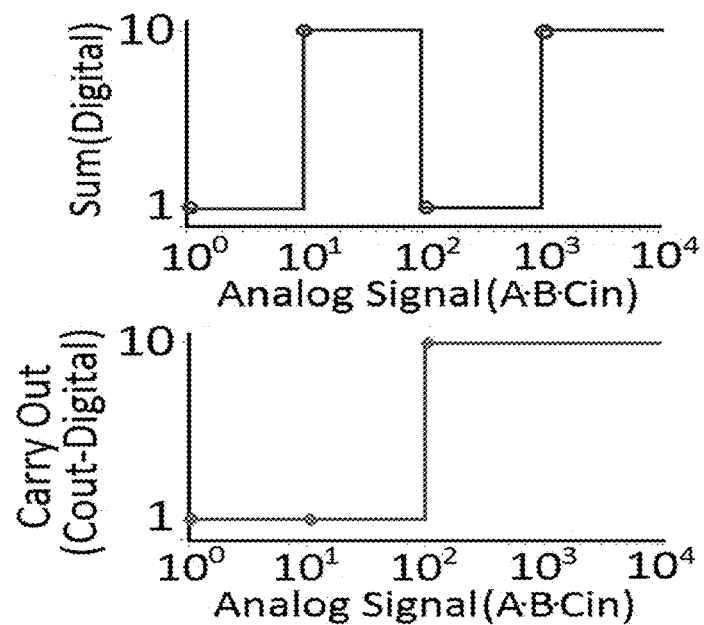
Figure 7D
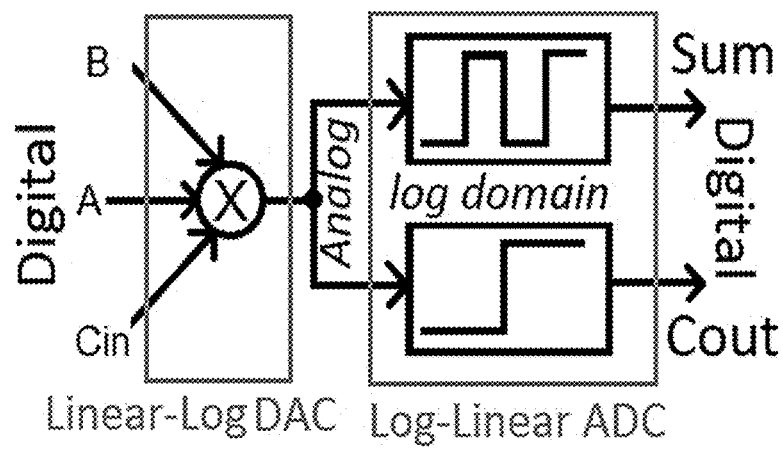

DNA-BASED NEURAL NETWORK

CROSS-REFERENCE TO RELATED APPLICATIONS

This application is a National Phase of PCT Patent Application No. PCT/IL2018/050706 having International filing date of Jun. 27, 2018, which claims the benefit of U.S. Provisional Patent Application No. 62/525,242, filed Jun. 27, 2017, and entitled "MACHINE LEARNING ALGORITHM AND USES THEREOF", the contents of which are incorporated herein by reference in its their entirety.

FIELD OF INVENTION

The present invention is directed to computer program products in the field of machine learning and synthetic biology.

BACKGROUND OF THE INVENTION

Biological systems are comprised of remarkable parallel and distributed computing networks with adaptive, self-repairing and replicative capacities in performance of real-world tasks. Scientists and engineers have been inspired to mimic these features in design of artificial intelligent systems. For example, neuromorphic computing applies abstract models of neural systems, such as the perceptron, using microelectronics, to build intelligent machines. However, because the neuromorphic computing discipline demands a deep understanding of biological mechanisms in brains, the field has progressed slowly.

During the past decade, researchers have successfully applied biophysical models to create basic biological networks with predictable behaviors in living cells, and have shown that biological networks are constructed from only a few types of design patterns that are implemented with different genes. At the same time, significant advancements in genomic DNA engineering and assembly techniques have been achieved, subsequently laying down an extraordinary set of design rules proposed to explain the complexity of biological systems and which have been exploited to construct synthetic gene networks in living cells. These rules are mostly inspired by computer and electrical engineering concepts. For example, several biological networks have been shown to act in an 'AND-logic-gate' manner to control promoter activity while others synthesize a toggle switch in bacteria. However, signals in living cells are stochastic (noisy) and analog (graded) in nature, such that digital logic abstraction is often an oversimplified means of capturing design features. Thus, the challenge remains in scaling-up gene networks, increasing biological robustness, and building adaptive biological systems, in view of cellular resource limitations, a deficiency of orthogonal genetic devices, and lack of simple learning mechanisms. Recently, it was shown that synthetic gene circuits can be engineered to execute analog computational functions in living cells. Such gene circuits exploit feedback loops to perform logarithmically linear sensing, addition, ratio-meter, and power-law computations. These circuits involve fewer components and execute more complex operations than their digital counterparts. In the same context, it has been shown that biological systems can be mapped to ultra-low-power analog translinear electronics systems, which is termed cytomorphics. For example, regulation of gene expression can be modeled by networks of subthreshold MOS (Metal-Oxide-Semiconductor) transistors.

Biological architectures in living cells contain extensively noisy, imprecise, and unreliable analog parts that collectively interact through analog and digital signals to solve interactively noise-tolerant parallel tasks online with astoundingly low power consumption, vastly exceeding the characteristics of present-day computers. For example, a single cell in the body performs $10^7$ biochemical reactions per second from its noisy molecular inputs, expending less than 1 $pW^{19}$. Furthermore, neural and molecular networks both use bit stream data-encoding pulses (spikes in neuron and mRNA transcript in cell biology) for processing and transcommunicating. Additionally, both systems use naturally graded signals for computation (post-synaptic potential in neurons or translation of mRNA to protein concentration in cell biology). Furthermore, both system types are composed of similar complex networks topologies (e.g. feed-forward, negative and positive feedbacks) and highly interconnected nodes. Both systems have two types of activation and repression and are adaptive to new environmental conditions by employing learning and evolution mechanisms.

SUMMARY

The following embodiments and aspects thereof are described and illustrated in conjunction with systems, tools and methods which are meant to be exemplary and illustrative, not limiting in scope.

There is provided, in accordance with an embodiment, an analog signal processing circuit comprising: a first promoter operably linked to a nucleic acid sequence encoding a first output molecule, wherein the promoter is responsive to a cooperative input signal comprising at least two cooperative inputs, and wherein expression of the at least two cooperative inputs is tunable.

In some embodiments, the cooperativity of the at least two inputs is tunable.

In some embodiments, the first promoter is a hybrid promoter comprising at least two transcriptional-regulator binding sites.

In some embodiments, at least one of the at least two regulator binding sites binds an activator and at least one of the at least two regulator binding sites binds a repressor.

In some embodiments, the at least two inputs bind to the at least two regulator binding sites, or the at least two inputs bind to at least two regulators that bind to the at least two regulator binding sites.

In some embodiments, the at least two regulator binding sites are a LuxR binding site and a LacI binding site.

In some embodiments, the at least two inputs are acyl-homoserine lactone (AHL) and isopropyl β-d-thiogalactopyranoside (IPTG).

In some embodiments, the analog signal processing further comprises a second promoter operably linked to a nucleic acid sequence encoding at least one of the cooperative inputs, wherein the second promoter comprises a binding site for the at least one of the cooperative inputs.

In some embodiments, the binding site in the second promoter comprises a modification that alters a binding affinity of the at least one cooperative input to the binding site relative to a binding affinity of the at least one cooperative input to an unmodified binding site.

In some embodiments, a binding affinity to the first promoter of the at least two inputs, or the at least two regulators bound to the inputs, is tunable.

In some embodiments, the analog signal processing circuit further comprises a third promoter operably linked to a nucleic acid sequence encoding a second output molecule, wherein the third promoter is responsive to the first output molecule.

In some embodiments, the third promoter comprises a pBAD promoter, and the first output molecule is araC protein.

In some embodiments, the analog signal processing circuit further comprises arabinose.

In some embodiments, the analog signal processing circuit further comprises: (a) a regulatory sequence that regulates translation of the first output molecule and is located between the first promoter and the nucleic acid sequence encoding the first output molecule; (b) a regulatory sequence that regulates translation of the second output molecule and is located between the third promoter and the nucleic acid sequence encoding the second output molecule; or both (a) and (b).

In some embodiments, the regulatory sequence is a riboswitch responsive to theophylline.

In some embodiments, the first promoter is responsive to a protein or protein complex consisting of more than one subunit, wherein the at least two cooperative inputs are at least two of the subunits.

In some embodiments, the protein consisting of more than one subunit is T7 RNA polymerase and the at least two cooperative inputs are an alpha-fragment subunit of T7 RNA polymerase, a sigma-fragment subunit of T7 RNA polymerase and a beta-core fragment subunit of T7 RNA polymerase.

In some embodiments, the analog signal processing circuit further comprises a nucleic acid sequence coding for the alpha-fragment subunit, a nucleic acid sequence coding for the sigma-fragment subunit and a nucleic acid sequence coding for the beta-core fragment subunit, wherein the nucleic acid sequences coding for the T7 RNA polymerase subunits are operably linked to at least one promoter.

In some embodiments, the nucleic acid sequences coding for the T7 RNA polymerase subunits are operably linked to a plurality of promoters, wherein all three nucleic acid sequences are not linked to the same promoter, and wherein the cooperativity of the inputs is determined by the binding affinities of the plurality of promoters.

In some embodiments, the protein consisting of more than one subunit is Cas9.

In some embodiments, the at least two cooperative inputs are Cas9 and a small guide RNA (sgRNA).

In some embodiments, the tunability of the Cas9 and the sgRNA is determined by mutating the sgRNA sequence to alter a binding affinity of the Cas9 to the sgRNA.

In some embodiments, the at least two cooperative inputs are at least two factors that share a common binding site, and wherein the first promoter comprises the common binding site.

In some embodiments, the analog signal processing circuit of the present invention further comprises the at least two factors that share a common binding site.

In some embodiments, the at least two factors that share a common binding site are a Sigma factor and an anti-Sigma factor.

In some embodiments, the first promoter operably linked to a nucleic acid sequence encoding a first output molecule further comprises a fourth promoter that transcribes in a direction opposite to a transcriptional direction of the first promoter, wherein binding of at least one of the at least two cooperative inputs to the fourth promoter interferes with transcription from the first promoter.

There is also provided, in accordance with an embodiment, an analog signal processing circuit comprising: (a) a first tunable promoter operably linked to a nucleic acid sequence coding for a DNA recombinase; (b) a second constitutive promoter operably linked to a nucleic acid sequence that, when inverted, codes for a first output molecule, wherein the nucleic acid sequence is flanked by recognition sites for the DNA recombinase; and (c) decoy recognition sites for the DNA recombinase, wherein said decoy sites are within (i) a nucleic acid molecule comprising (a), (ii) a nucleic acid molecule comprising (b), or (iii) a third nucleic acid molecule.

In some embodiments, the tunable promoter comprises a Plux binding site, and is tunable by addition of AHL.

In some embodiments, the circuit converts an analog signal into a digital output.

In some embodiments, the circuit further comprises a cell which encloses the components of the system.

In some embodiments, the cell is selected from a prokaryotic or a eukaryotic cell.

In some embodiments, the output molecule is a fluorescent molecule.

There is also provided, in accordance with an embodiment, a cell comprising the analog signal processing circuit of the present invention.

There is further provided, in accordance with an embodiment, a method for converting an analog signal into a digital output, comprising contacting the analog signal processing circuit of the present invention, or the cell of the present invention, with the at least two inputs and detecting the first output molecule, the second output molecule, or both thereby converting an analog signal into a digital output.

In some embodiments, the detecting comprises quantification of the output molecule.

In some embodiments, the digital output is either a positive or a negative output.

In some embodiments, the method further comprises tuning a threshold for converting the analog input into a positive digital output.

In some embodiments, the tuning comprises at least one of: tuning expression of at least one of the at least two regulators; tuning a binding efficiency of at least one of the at least two inputs to a binding site; tuning a binding efficiency of at least one of the at least two regulators to a binding site; adding a molecule that binds to the regulatory sequence; and adding a molecule that binds to the first output molecule and alters binding of the first output molecule to the third promoter.

In some embodiments, the molecule that binds the regulatory sequence is theophylline.

In some embodiments, the molecule that binds to the first output molecule is arabinose.

There is further provided in accordance with an embodiment, a system comprising at least one hardware processor; and a non-transitory computer-readable storage medium having stored thereon program instructions, the program instructions executable by the at least one hardware processor to execute a genetic-type machine learning algorithm configured for: receiving a sequence of inputs, wherein each of said inputs has an associated weight, operating a neural network to generate, as output, a weighted multiplication of said inputs, calculating an error value between said output and a target output, and adjusting the values of one or more of said weights based on said error value and a specified learning rate, wherein said adjusting is determined, at least in part, based on a log-linear gradient descent training rule.

There if further provided in accordance with an embodiment, a method comprising operating at least one hardware processor for executing a genetic-type machine learning algorithm configured for: receiving a sequence of inputs, wherein each of said inputs has an associated weight, operating a neural network to generate, as output, a weighted multiplication of said inputs, calculating an error value between said output and a target output, and adjusting the values of one or more of said weights based on said error value and a specified learning rate, wherein said adjusting is determined, at least in part, based on a log-linear gradient descent training rule.

There if further provided in accordance with an embodiment, a computer program product comprising a non-transitory computer-readable storage medium having program instructions embodied therewith, the program instructions executable by at least one hardware processor to execute a genetic-type machine learning algorithm configured for: receiving a sequence of inputs, wherein each of said inputs has an associated weight, operating a neural network to generate, as output, a weighted multiplication of said inputs, calculating an error value between said output and a target output, and adjusting the values of one or more of said weights based on said error value and a specified learning rate, wherein said adjusting is determined, at least in part, based on a log-linear gradient descent training rule In some embodiments, the hardware processor is a DNA-based processor.

In some embodiments, the algorithm is further configured to repeat iteratively said steps of operating, calculating, and adjusting, until said error value is less than a specified threshold.

In some embodiments, the neural network comprises a plurality of layers. In some embodiments, said adjusting further comprises backpropagating said gradient descent through said plurality of layers, using the chain rule derivatives.

In some embodiments, said calculating comprises determining a mean square error value.

In some embodiments, said learning rate is an adaptive learning rate.

In addition to the exemplary aspects and embodiments described above, further aspects and embodiments will become apparent by reference to the figures and by study of the following detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Exemplary embodiments are illustrated in referenced figures. Dimensions of components and features shown in the figures are generally chosen for convenience and clarity of presentation and are not necessarily shown to scale. The figures are listed below.

FIGS. 7A-H: (7A) implementation of elementary logic gates using a linear threshold (LTU) model, (7B) truth table of 1-bit full adder, (7C) full bit adder outputs as a function of the analog multiplication signal, (7D) implementation of a 1-bit full adder using a log-linear threshold ($L^2TU$) model, (7E) construction and results of a linear-log digital-to-analog converter in living cells, (7F) & (7G) construction and experimental results of log-linear analog-to-digital converter processing unit to implement low/band/high pass circuits in E. coli, and (7H) experimental results of cell-to-cell communication using AHL quorum sensing molecules;

DETAILED DESCRIPTION OF THE INVENTION

Figure 1A:
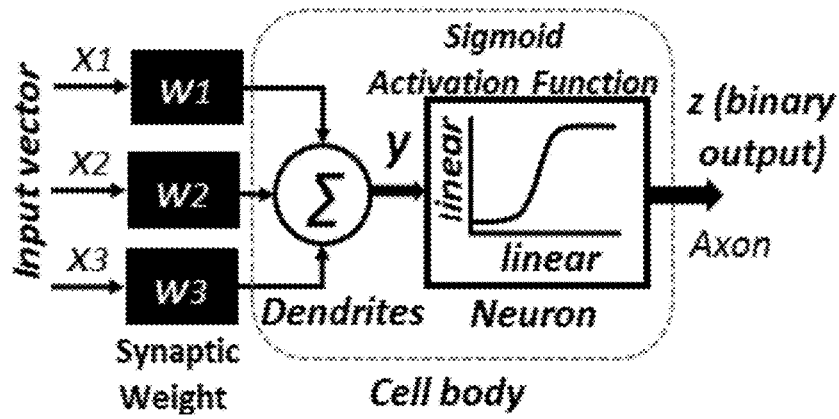
FIGS. 1A-F: (1A) anatomical structure of the perceptron, (1B) shifted sigmoid function, (1C) shifted sigmoid function in a log-linear domain fits a Michaelis-Menten model, (1D) three main models of cooperativity in living cells, (1E) anatomical structure of the perceptgene, and (1F) simulation results of the perceptgene using a signum activation function.

Disclosed herein are a system and a method which provide for synthetic gene networks in living cells that can demonstrate the computational abilities of neural networks. The present invention provides for the mapping of neural networks to molecular biological and nanoelectronic networks, using a simple mathematical transformation. The disclosed approach may be configured for providing a novel computational framework that inherently exists in synthetic gene networks and is implemented by translinear analog circuits and memristor devices to build adaptive systems with emergent collective parallel computational abilities in electronics and living cells.

The present invention is based, at least in part, on the notion that artificial neural networks (ANNs) are a set of theoretical abstract models inspired by neurobiological networks. ANNs have been proposed as a powerful computational framework for translation of interactive cognitive tasks that the human brain appears to solve relatively easily as compared to a conventional computer, such as content addressable memory, pattern classification, object recognition, function approximation, and optimizations solving. ANNs use simple-unreliable analog-weighted elements that collectively interact through non-linear functions, which act to achieve reliable decision-making. The interactions between non-linear functions (nodes) through the analog connections (weights) lead to global behavior of the network, which cannot be observed only by the node elements. The second key feature of ANN is its plasticity—the ability to learn and adapt to new patterns based on dataset history (information) compressed within the analog weights, which are periodically updated.

The perceptron, which is the basic computational element in ANNs, is an abstract model that can capture the computational power of biological neurons. Because biological and neural architectures share many features, a simple transformation between the basic computational structure of perceptron and molecular processing unit can be discerned. Accordingly, an interaction between proteins and DNA that controls the promoter activity ($P_r$, comprising a region of DNA that initiates transcription of a particular gene) can be viewed either as a node or as an activation function which, in turn, can be simply described by a Michaelis-Menten model.

In analogy to the perceptron, it may be assumed that the activity of the promoter in DNA is a signum function. However, in natural and synthetic systems, it is approximated as a log-linear sigmoid function (Hill-function). In some embodiments, the present framework, termed 'perceptgene,' may be modeled on this framework. The perceptgene is inspired by molecular biology and has a computational process identical to that of the perceptron, i.e., consisting of three operations: (i) multiplication of all the inputs in analog fashion; this process is mainly implemented by binding reactions, (ii) each input ($x_i$) is invoked by a power law function with a coefficient $n_i$ that represents the cooperativity binding reaction, and (iii) a log-linear activation function that is implemented by promoter activity or a bio-enzymatic reaction (thresholding).

The present framework is inspired by neural biology, which is inherently present in cellular biology, to build intelligent parallel processing biological systems. In contrast to most current approaches, which emphasize digital paradigms of thought by building artificial logic gates, counter, discrete quantizer and memory devices in living cells, the disclosed framework can execute sophisticated analog computational and learning (evolutionary) functions in concert with decision-making digital circuits within living cells. In some embodiments, the present framework may provide for an intelligent adaptive-robust-parallel computing synthetic biological systems that set constraints on energy and host cell resources. In addition, in some embodiments, the present framework may be able to leverage the multidisciplinary nature of cytomorphics to interpolate/extrapolate principles of molecular networks into engineering, and vice versa, just as neuromorphic engineering has led to biologically inspired engineered systems.

As noted above, because signals in living cells are stochastic (noisy) and analog (graded) in nature, digital logic abstraction is often an oversimplified means of capturing design features. Some of the limitations of analog frameworks include noise sensitivity, low dynamic range, lack of design standards, exhaustive manual design flow and long time-to-market, large developing costs and human resources.

Accordingly, in some embodiments, the present framework provides for novel adaptive synthetic biological systems and collective emergent electronic circuits that operate precisely and with minimal energy requirements. Such systems may be utilized in many fields and areas, by interpolating new applications, such as comprehensive study of complex biological systems (e.g., mutations involved in cancer, see Loeb K R, Loeb L a. Significance of multiple mutations in cancer. *Carcinogenesis.* 2000; 21(3):379-385. doi:10.1093/carcin/21.3.379); embedded electronic systems for big data processing in healthcare (see Foster K R, Koprowski R, Skufca J D. Machine learning, medical diagnosis, and biomedical engineering research—commentary. *Biomed Eng Online.* 2014; 13(1):94. doi:10.1186/1475-925X-13-94); and ultra-low power systems design for biomedical applications (e.g., low-cost microelectronics with equally low-cost genetically engineered microbial sensors; see Sarpeshkar R. *Ultra Low Power Bioelectronics: Fundamentals, Biomedical Applications, and Bio-Inspired Systems;* 2010. doi:http://dx.doi.org/10.1017/CBO9780511841446; Daniel R, Almog R, Ron A, Belkin S, Shachm-Diamand Y. Modeling and Measurement of a Whole-cell Bioluminescent Biosensor Based on a Single Photon Avalanche Diode. Biosensors and Bioelectronics 2008; 24 (882)). The present systems may also be configured for setting the fundamental understanding and competent engineering tools required to build an intelligent hybrid machine-organism system (e.g., to develop bio-classifiers for detection of disease that are connected via the Internet-of-Things, see Gubbi J, Buyya R, Marusic S, Palaniswami M. Internet of Things (IoT): A vision, architectural elements, and future directions. *Futur Gener Comput Syst.* 2013; 29(7):1645-1660. doi:10.1016/j.future.2013.01.010).

In some embodiments, the present invention provides for a novel abstract molecular cell biology model, termed 'perceptgene,' equivalent to the perceptron model which is widely used in artificial neural networks (ANNs) (see, e.g., Rosenblatt F. The Perceptron—A Perceiving and Recognizing Automaton. *Rep 85, Cornell Aeronaut Lab.* 1957:460-461. doi:85-460-1; Mackay D J C. Information Theory, Inference, and Learning Algorithms. *Learning.* 2003; 22(3): 348-349. doi:10.1017/S026357470426043X). This novel model will be inherently implemented in gene networks to construct synthetic molecular networks (SMNs), as well as in translinear electronic circuits to build artificial molecular networks (AMNs).

In some embodiments, the present invention may be configured for developing an alternative learning algorithm based on the perceptgene model, by optimizing the output error using gradient descent in a log-linear domain. The present invention may then be configured for being concurrently applied in SMNs and AMNs to build adaptive biological systems with evolutionary abilities and ultra-low power bioinspired translinear electronic circuits for supervised learning big-data applications.

In some embodiments the present invention may be configured for developing an alternative model of the Hopfield energy function (see, e.g., Hopfield J J. Neural networks and physical systems with emergent collective computational abilities. *Proc Natl Acad Sci USA*. 1982; 79(8): 2554-2558. doi:10.1073/pnas.79.8.2554 33), relying on the perceptgene model in a log-linear domain. This may then be applied in SMNs and AMNs to build biological and electronics systems with parallel computational abilities (Boltzmann machine; see, e.g., Hinton G, Hinton G, Sejnowski T, Sejnowski T. *Learning and Relearning in Boltzmann Machines*. Vol 1; 1986).

In some embodiments, the present invention may be configured for developing an alternative model of the linear threshold unit model, relying on the perceptgene model in a log-linear model. This may then be applied in SMNs to scale gene networks in living cells. Furthermore, the perceptgene model may be utilized to study the architecture of gene networks in natural biological systems for scaling synthetic bio-inspired systems.

In some embodiments, the present invention provides for an analog signal processing circuit comprising a first promoter operably linked to a nucleic acid sequence encoding a first output molecule, wherein the promoter is responsive to a cooperative input signal. In other embodiments, the present invention provides for a cell comprising the analog signal processing circuit of the invention. In yet other embodiments, the present invention provides for a method for converting an analog signal into a digital output, comprising contacting the analog signal processing circuit of the invention or a cell of the invention with a cooperative input signal and detecting at least one output molecule, thereby converting an analog signal into a digital output.

As used herein, an "analog signal" refers to any input with at least one parameter that varies in magnitude. It will be understood by one skilled in the art, that an analog signal is not a signal that is either present or absent, but rather a signal that when present has a variable magnitude. In some embodiments, an analog signal is not an AND/OR signal. In some embodiments, an analog signal is not a digital signal. In some embodiments, an analog signal is not a binary signal. As used herein, a "digital signal" is a binary signal which is measured as only present or absent.

In some embodiments, the cooperative input signal comprises at least two cooperative inputs. In some embodiments, the cooperative inputs are tunable. In some embodiments, the cooperative input signal comprises at least 2, 3, 4, 5 or 10 cooperative inputs. Each possibility represents a separate embodiment of the invention. In some embodiments, the cooperativity of the at least two inputs is tunable. As used herein, the term "tunable" refers to the ability to be changed or modified. As the input to the circuit is analog it has a variable value, as such the inputs which correspond to the analog input are also variable.

As used herein, the term "cooperativity" refers to manner in which two or more molecules interact with each other and effect their ability to function. In some embodiments, the cooperativity is cooperativity in signaling. In some embodiments, the cooperativity is cooperativity in binding. In some embodiments, the cooperativity is cooperativity in binding to a promoter. In some embodiments, the cooperativity is cooperativity of at least two binding sites. In some embodiments, the cooperativity is cooperativity of at least two proteins. In some embodiments, the cooperativity is cooperativity of at least two promoters. In some embodiments, the cooperativity is tunable. By mutating or altering one of the cooperative molecules the cooperativity can be changed.

In some embodiments, altering the binding site tunes cooperativity. In some embodiments, altering the promoter tunes cooperativity. In some embodiments, alteration of a nucleic acid comprises mutation of the nucleic acid. In some embodiments, the mutation is a site directed mutagenesis to a particular mutation. In some embodiments, the mutation is a random mutation.

As used herein, the term "operably linked" means that the nucleic acid sequence of interest is linked to the regulatory element(s), e.g. the promoter, in a manner that allows for expression of the nucleotide sequence. In some embodiments, the promoter is linked by an intervening nucleotide sequence. In some embodiments, the promoter is linked directly to the output nucleic acid sequence. In some embodiments, the output nucleic acid sequence is linked in frame such that the output sequence is translated.

As used herein, the term "responsive to" refers to the promoter's activation status being altered by the cooperative input signal. In some embodiments, the response is to start transcription. In some embodiments, the response is to increase transcription. In some embodiments, the response is to stop transcription. In some embodiments, the response is to decrease transcription. In some embodiments, the response is to block transcription. In some embodiments, the response is any one of: starting, stopping, increasing, decreasing and blocking transcription. In some embodiments, the promoter is responsive to a part of the cooperative input signal. In some embodiments, the promoter is responsive to a part of the cooperative input signal that regulates transcription. In some embodiments, the cooperative input signal regulates transcription and translation.

In some embodiments, the nucleic acid molecules of the invention are in vectors. In some embodiments, the vectors are expression vectors or recombinant expression vectors. Recombinant expression vectors can comprise the circuit of the invention in a form suitable for expression of the nucleic acids in a host cell or expression system, which means that the recombinant expression vectors include one or more regulatory elements, which may be selected on the basis of the host cells to be used for expression, that is operatively-linked to the nucleic acid sequence to be expressed.

A vector nucleic acid sequence generally contains at least an origin of replication for propagation in a cell and optionally additional elements, such as a heterologous polynucleotide sequence, expression control element (e.g., a promoter, enhancer), selectable marker (e.g., antibiotic resistance), poly-Adenine sequence.

The vector may be a DNA plasmid delivered via non-viral methods or via viral methods. The viral vector may be a retroviral vector, a herpesviral vector, an adenoviral vector, an adeno-associated viral vector or a poxviral vector. The promoters may be active in mammalian cells. The promoters may be a viral promoter.

In some embodiments, the vector is introduced into the cell by standard methods including electroporation (e.g., as described in From et al., Proc. Natl. Acad. Sci. USA 82, 5824 (1985)), heat shock, infection by viral vectors, high velocity ballistic penetration by small particles with the nucleic acid either within the matrix of small beads or particles, or on the surface, and/or the like.

General methods in molecular and cellular biochemistry, such as may be useful for carrying out DNA and protein recombination, as well as other techniques described herein, can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998).

In some embodiments, the analog signal processing circuit of the invention further comprises a cell. In some embodiments, the analog signal processing circuit of the invention is enclosed within a cell. In some embodiments, the analog signal processing circuit of the invention is in a cell. In some embodiments, the cell is a prokaryotic cell. In some embodiments, the cell is a eukaryotic cell. In some embodiments, the cell is a prokaryotic or a eukaryotic cell. In some embodiments, the cell is an *E. coli* cell. In some embodiments, the eukaryotic cell is a mammalian cell.

In some embodiments, the first promoter is a hybrid promoter. As used herein, a "hybrid promoter" refers to a synthetic promoter comprising at least two distinct elements from other promoters. In some embodiments, the promoter comprises other elements required for transcription besides the hybrid elements. In some embodiments, the hybrid promoter comprises at least two regulator binding sites. As used herein, "regulators" refer to molecules that regulate or modulate transcription. In some embodiments, the hybrid promoter comprises at least two protein binding sites. In some embodiments, the hybrid promoter comprises binding sites for at least two proteins. In some embodiments, the proteins are transcriptional regulators. In some embodiments, the proteins are transcription factors. In some embodiments, the regulators are nucleic acid molecules. In some embodiments, a regulator is a transcriptional activator. In some embodiments, a regulator is a transcriptional repressor. In some embodiments, the hybrid promoter comprises a binding site for an activator and a binding site for a repressor. In some embodiments, at least one of the at least two regulator binding sites binds an activator. In some embodiments, at least one of the at least two regulator binding sites binds a repressor.

In some embodiments, the at least two inputs are the regulators. In some embodiments, the at least two inputs bind to molecules that are the regulators. In some embodiments, the at least two inputs bind to the at least two regulator binding sites. In some embodiments, the at least two inputs bind to at least two regulators that bind to the at least two regulator binding sites. In some embodiments, binding of an input to a regulator alters the binding affinity of the regulator to the binding site. In some embodiments, an input increases binding affinity. In some embodiments, an input decreases binding affinity. In some embodiments, at least one input increases binding affinity and at least one input decreases binding affinity.

In some embodiments, the at least two regulator binding sites are a LuxR binding site and a LacI binding site. In some embodiments, a regulator binding site is a LuxR binding site. In some embodiments, a regulator binding site is a LacI binding site. In some embodiments, a regulator binding site is a riboswitch. In some embodiments, the regulators are LuxR and LacI. In some embodiments, a regulator is LuxR. In some embodiments, a regulator is LacI. In some embodiments, a regulator is theophylline. In some embodiments, the regulators are LuxR and theophylline. In some embodiments, a regulator comprises a destabilizing moiety. Such a moiety would result in degradation or clearance of the regulator. In some embodiments, binding of an input to the regulator stabilizes the destabilized molecule. In some embodiments, the destabilizing moiety is a ssrA degradation tag. In some embodiments, the at least two inputs are acyl-homoserine lactone (AHL) and isopropyl β-d-thiogalactopyranoside (IPTG). In some embodiments, an input is AHL. In some embodiments, an input is IPTG. In some embodiments, an input is theophylline. In some embodiments, the at least two inputs are AHL and theophylline.

In some embodiments, the analog signal processing circuit further comprises a second promoter operably linked to a nucleic acid sequence encoding at least one of the cooperative inputs. In some embodiments, the second promoter comprises a binding site for the at least one cooperative input. In some embodiments, the second promoter molecule is a positive feedback molecule. In some embodiments, the analog signal processing circuit further comprises a negative feedback molecule. The positive and negative feedback molecules allow for tuning of the amount of the input molecules. In this way the analog signal can be modulated to a very wide dynamic range such as is described herein.

In some embodiments, the binding site in the second promoter comprises a modification that alters a binding affinity of the at least one cooperative input to the binding site. In some embodiments, the altering of the binding affinity is relative to a binding affinity of the at least one cooperative input to an unmodified binding site, or the that binding site before modification. Mutation of this binding site on the feedback molecule allows for tuning of the feedback and thus tuning of the inputs. In some embodiments, a binding affinity to the second promoter of one of the at least two inputs is tunable.

In some embodiments, a binding affinity to the first promoter of at least one of the at least two inputs is tunable. In some embodiments, a binding affinity to the first promoter of the at least two inputs is tunable. In some embodiments, a binding affinity to the first promoter of at least one of the at least two regulators is tunable. In some embodiments, a binding affinity to the first promoter of the at least two regulators is tunable. In some embodiments, a binding affinity to the first promoter of at least one of the at least two regulators bound to an input in tunable. In some embodiments, a binding affinity to the first promoter of the at least two regulators bound to the inputs is tunable.

In some embodiments, the analog signal processing circuit further comprises a third promoter operably linked to a nucleic acid sequence encoding a second output molecule. In some embodiments, the third promoter is responsive to the first output molecule. In some embodiments, the output molecule is a molecule for detection. In some embodiments, the output molecule is a fluorescent molecule. Fluorescent molecules are well known in the art and include, but are not limited to, green fluorescent protein (GFP), mCherry, YFP, Cy3, Cy5, and Cy7. In some embodiments, the first output molecule is not a molecule for detection. In some embodiments the first output molecule is araC protein. In some embodiments, the first output molecule is not for detection and the second output molecule is for detection. In some embodiments, both output molecules are for detection. In some embodiments, the third promoter comprises a binding site for the first output molecule. In some embodiments the first output molecule is araC protein. In some embodiments, the third promoter comprises a pBAD site. In some embodiments, the third promoter is a pBAD promoter.

In some embodiments, the analog signal processing circuit further comprises arabinose. In some embodiments, the analog signal processing circuit further comprises the inputs. In some embodiments, the analog signal processing circuit further comprises at least one input. In some embodiments, the analog signal processing circuit further comprises at least two inputs. In some embodiments, the analog signal processing circuit further comprises AHL. In some embodiments, the analog signal processing circuit further comprises IPTG. In some embodiments, the analog signal processing circuit further comprises theophylline. In some embodiments, the analog signal processing circuit further comprises AHL and IPTG. In some embodiments, the analog signal processing circuit further comprises AHL and theophylline.

In some embodiments, the analog processing circuit further comprises a regulator sequence that regulates translation of the first output molecule and is located between the first promoter and the nucleic acid sequence encoding for the first output molecule. In some embodiments, the analog signal processing circuit further comprises a regulatory sequence that regulates translation of the second output molecule and is located between the third promoter and the nucleic acid sequence encoding the second output molecule. In some embodiments, the analog signal processing circuit further comprises (a) a regulator sequence that regulates translation of the first output molecule and is located between the first promoter and the nucleic acid sequence encoding for the first output molecule; (b) a regulatory sequence that regulates translation of the second output molecule and is located between the third promoter and the nucleic acid sequence encoding the second output molecule; or (a) and (b). In some embodiments, the regulatory sequence is part of the promoter. In some embodiments, the regulatory sequence is separate from the promoter. In some embodiments, the regulatory sequence is in the nucleic acid sequence encoding the output molecule. In some embodiments, the regulatory sequence is not in the nucleic acid sequence encoding the output molecule. In some embodiments, the regulatory sequence is in a non-coding region. the output molecule. In some embodiments, the regulatory sequence is in a non-coding region after the nucleic acid sequence encoding the output molecule. In some embodiments, the regulatory sequence is in a non-coding region before the nucleic acid sequence encoding the output molecule. In some embodiments, the regulatory sequence is in a non-coding region before or after the nucleic acid sequence encoding the output molecule. In some embodiments, the regulatory sequence is in an untranslated region (UTR). In some embodiments, the regulatory sequence is in the 3' UTR. In some embodiments, the regulatory sequence is in the 5' UTR.

In some embodiments, the regulatory sequence is a regulatory RNA binding site. In some embodiments, the regulatory sequence is a miR binding site. In some embodiments, the regulatory sequence is a siRNA binding site. In some embodiments, the regulatory sequence is a lncRNA binding site. In some embodiments, the input is the regulatory RNA. In some embodiments, the input is the miR. In some embodiments, the input is the siRNA. In some embodiments, the input is the lncRNA.

In some embodiments, the regulatory sequence is a riboswitch. In some embodiments, the regulatory sequence codes for a riboswitch in the translated mRNA. As used herein, the term "riboswitch" refers to a segment in an mRNA that binds to specific effector molecules and modifies the riboswitch-containing mRNA's protein production. In some embodiments, the riboswitch modified at least one of mRNA stability, translation rate, and translational elongation. In some embodiments, the riboswitch modifies translation rate. In some embodiments, binding of the effector molecule decreases or halts translation. In some embodiments, binding of the effector molecule increases or starts translation. It will be understood by one skilled in the art that the effector molecule is one of the cooperative inputs, specifically an input that regulates translation of the output molecule. In some embodiments, the effector molecule is a small molecule. In some embodiments, the effector molecule is a metabolite. In some embodiments, the effector molecule is theophylline. In some embodiments, the effector molecule is a cooperative input.

In some embodiments, the first promoter is responsive to a protein comprising more than one subunit. In some embodiments, the first promoter is responsive to a protein complex comprising more than one subunit. In some embodiments, the protein or protein complex consists of more than one subunit. In some embodiments, the protein or protein complex consists of 2, 3, 4, 5, 6, 7, 8, 9, 10, 11 or 12 subunits. Each possibility represents a separate embodiment of the invention. In some embodiments, the at least two cooperative inputs are at least two of the subunits. In some embodiments, the at least two cooperative inputs are all of the subunits of the protein or complex. In some embodiments, the at least two cooperative inputs are all of the subunits of the protein or complex required to regulate the promoter. In some embodiments, the cooperativity of the subunits is determined by the binding affinities of the subunits. In some embodiments, the cooperativity of the subunits is determined by the expression levels of the subunits.

In some embodiments, the protein consisting of more than one subunit is a transcription factor. In some embodiments, the protein consisting of more than one subunit is a polymerase. In some embodiments, the protein consisting of more than one subunit is a nuclease. In some embodiments, the nuclease is an endonuclease. In some embodiments, the polymerase is an RNA polymerase.

In some embodiments, the RNA polymerase is T7 RNA polymerase. In some embodiments, the at least two cooperative inputs are T7 RNA polymerase subunits. In some embodiments, the T7 RNA polymerase subunits are selected from an alpha-fragment subunit of T7 RNA polymerase, a sigma-fragment subunit of T7 RNA polymerase and a beta-core fragment subunit of T7 RNA polymerase. In some embodiments, the at least two inputs are an alpha-fragment subunit of T7 RNA polymerase, a sigma-fragment subunit of T7 RNA polymerase and a beta-core fragment subunit of T7 RNA polymerase. In some embodiments, the endonuclease is Cas9.

In some embodiments, the analog signal processing circuit of the invention further comprises a nucleic acid sequence coding for at least one of the subunits. In some embodiments, the analog signal processing circuit of the invention comprises a nucleic acid sequence coding for all the subunits. In some embodiments, the nucleic acid sequences coding for the subunits are operably linked to at least one promoter. In some embodiments, all the subunit-encoding nucleic acid sequences are operably linked to the same promoter. In some embodiments, all the subunit-encoding nucleic acid sequences are not operably linked to the same promoter. In some embodiments, all the subunit-encoding nucleic acid sequences are operably linked to different promoters. In some embodiments, the subunit-encoding nucleic acid sequences are operably linked to a plurality of promoters. In some embodiments, each subunit-encoding nucleic acid sequence is linked to one promoter. In some embodiments, each subunit-encoding nucleic acid sequence is linked to only one promoter, and at least two promoters are so linked. A skilled artisan will understand that each sequence can be linked to more than one promoter or to several promoters. Similarly, more than one sequence can be linked to a single promoter (thus having coordinated expression) or each sequence can have its own separate promoter (uncoordinated expression). Lastly, some of the sequences coding for subunits may be operably linked to the same promoter (coordinated expression), while others may have separate promoters (uncoordinated).

In some embodiments, the cooperativity of the inputs is determined by the binding affinities of the promoters. In some embodiments, the promoters are not constitutively active, and the cooperativity of the inputs is determined by the binding affinities of the promoters for an activating molecule. In some embodiments, at least one of the cooperative inputs is an activating molecule for a promoter operably linked to a nucleic acid sequence encoding a subunit. In some embodiments, the inputs are the activating molecules. In some embodiments, the inputs are the subunits and the activating molecules are used to tune the inputs. In some embodiments, the inputs are the subunits and the activating molecules are used to tune the cooperativity of the inputs.

In some embodiments, the at least two cooperative inputs are an enzyme and at least one of the enzyme's cofactors. As used herein, a "cofactor" refers to a molecule, other than the substrate, whose presence is essential for the activity of the enzyme. In some embodiments, the enzyme acts on the promoter. In some embodiments, the enzyme acts on a nucleic acid molecule comprising the promoter. In some embodiments, the enzyme is selected from a polymerase, a helicase, a nuclease, a recombinase and a transferase. In some embodiments, the cooperativity of the enzyme and cofactor is determined by the binding affinities to each other. In some embodiments, the cooperativity of the enzyme and cofactor is determined by the expression levels of the enzyme and cofactor. In some embodiments, tuning the cooperativity comprises mutating the enzyme or cofactor, or the interaction sites of the enzyme and cofactor.

In some embodiments, the enzyme is Cas9. In some embodiments, the cofactor is a small guide RNA (sgRNA). In some embodiments, the tunability of the Cas9 and sgRNA is determined by mutating the sgRNA sequence. In some embodiments, the tunability of the Cas9 and sgRNA is determined by altering a binding affinity of the Cas9 to the sgRNA. In some embodiments, mutating the sgRNA sequence alters the binding affinity of the Cas9 to the sgRNA.

According to some embodiments, Cas9, unwinds DNA duplex and searches for sequences matching the sgRNA to cleave. Target recognition occurs upon detection of complementarity between a "protospacer" sequence in the target DNA and the remaining spacer sequence in the sgRNA. Importantly, Cas9 cuts the DNA only if a correct protospacer-adjacent motif (PAM) is also present at the 3' end. According to certain embodiments, different protospacer-adjacent motif can be utilized. For example, the *S. pyogenes* system requires an NGG sequence, where N can be any nucleotide. Bioinformatic analyses have generated extensive databases of CRISPR loci in a variety of bacteria that may serve to identify additional useful PAMs and expand the set of CRISPR-targetable. In *S. pyogenes*, Cas9 generates a blunt-ended double-stranded break 3 bp upstream of the protospacer-adjacent motif (PAM) via a process mediated by two catalytic domains in the protein: an HNH domain that cleaves the complementary strand of the DNA and a RuvC-like domain that cleaves the non-complementary strand.

The term "single guide RNA" (sgRNA), is a 20 bp RNA molecule that can form a complex with Cas9 and serve as the DNA recognition module. sgRNA is typically designed as a synthetic fusion of the CRISPR RNA (crRNA) and the trans-activating crRNA.

Cas9 proteins are known to exist in many Type II CRISPR systems including, but not limited to the following: *Methanococcus maripaludis* C7; *Corynebacterium diphtheriae*; *Corynebacterium efficiens* YS-314; *Corynebacterium glutamicum* ATCC 13032 Kitasato; *Corynebacterium glutamicum* ATCC 13032 Bielefeld; *Corynebacterium glutamicum* R; *Corynebacterium kroppenstedtii* DSM 44385; *Mycobacterium abscessus* ATCC 19977; *Nocardia farcinica* IFM10152; *Rhodococcus erythropolis* PR4; *Rhodococcus jostii* RHA1; *Rhodococcus opacus* B4 uid36573; *Acidothermus cellulolyticus* 11B; *Arthrobacter chlorophenolicus* A6; *Kribbella flavida* DSM 17836 uid43465; *Thermomonospora curvata* DSM 43183; *Bifidobacterium dentium* Bdl; *Bifidobacterium longum* DJO10A; *Slackia heliotrinireducens* DSM 20476; *Persephonella marina* EX HI; *Bacteroides fragilis* NCTC 9434; *Capnocytophaga ochracea* DSM 7271; *Flavobacterium psychrophilum* JIP02 86; *Akkermansia muciniphila* ATCC BAA 835; *Roseiflexus castenholzii* DSM 13941; *Roseiflexus* RSI; *Synechocystis* PCC6803; *Elusimicrobium minutum* Peil91; uncultured Termite group 1 bacterium phylotype Rs D17; *Fibrobacter succinogenes* S85; *Bacillus cereus* ATCC 10987; *Listeria innocua*; *Lactobacillus casei*; *Lactobacillus rhamnosus* GG; *Lactobacillus salivarius* UCC1 18; *Streptococcus agalactiae* A909; *Streptococcus agalactiae* NEM316; *Streptococcus agalactiae* 2603; *Streptococcus dysgalactiae equisimilis* GGS 124; *Streptococcus equi zooepidemicus* MGCS 10565; *Streptococcus gallolyticus* UCN34 uid46061; *Streptococcus gordonii* Challis subst CHI; *Streptococcus mutans* NN2025 uid46353; *Streptococcus mutans*; *Streptococcus pyogenes* Ml GAS; *Streptococcus pyogenes* MGAS5005; *Streptococcus pyogenes* MGAS2096; *Streptococcus pyogenes* MGAS9429; *Streptococcus pyogenes* MGAS 10270; *Streptococcus pyogenes* MGAS6180; *Streptococcus pyogenes* MGAS315; *Streptococcus pyogenes* SSI-1; *Streptococcus pyogenes* MGAS 10750; *Streptococcus pyogenes* NZ131; *Streptococcus thermophiles* CNRZ1066; *Streptococcus thermophiles* LMD-9; *Streptococcus thermophiles* LMG 18311; *Clostridium botulinum* A3 Loch Maree; *Clostridium botulinum* B Eklund 17B; *Clostridium botulinum* Ba4657; *Clostridium botulinum* F Langeland; *Clostridium cellulolyticum* H10; *Finegoldia magna* ATCC 29328; *Eubacterium rectale* ATCC 33656; *Mycoplasma gallisepticum*; *Mycoplasma* mobile 163K; *Mycoplasma penetrans*; *Mycoplasma synoviae* 53; *Streptobacillus moniliformis* DSM 12112; *Bradyrhizobium* BTAil; *Nitrobacter hamburgensis* X14; *Rhodopseudomonas palustris* BisB18; *Rhodopseudomonas palustris* BisB5; *Parvibaculum lavamentivorans* DS-1; *Dinoroseobacter shibae* DFL 12; *Gluconacetobacter diazotrophicus* Pal5 FAPERJ; *Gluconacetobacter diazotrophicus* Pal 5 JGI; *Azospirillum* B510 uid46085; *Rhodospirillum rubrum* ATCC 11170; *Diaphorobacter* TPSY uid29975; *Verminephrobacter eiseniae* EF01-2; *Neisseria meningitides* 053442; *Neisseria meningitides* alpha14; *Neisseria meningitides* Z2491; *Desulfovibrio salexigens* DSM 2638; *Campylobacter jejuni* doylei 26997; *Campylobacter jejuni* 81116; *Campylobacter jejuni*; *Campylobacter lari* RM2100; *Helicobacter hepaticus*; *Wolinella succinogenes*; *Tolumonas auensis* DSM 9187; *Pseudoalteromonas atlantica* T6c; *Shewanella pealeana* ATCC 700345; *Legionella pneumophila* Paris; *Actinobacillus succinogenes* 130Z; *Pasteurella multocida*; *Francisella tularensis novicida* U112; *Francisella tularensis holarctica*; *Francisella tularensis* FSC 198;

*Francisella tularensis tularensis; Francisella tularensis* WY96-3418; and *Treponema denticola* ATCC 35405.

One skilled in the art will appreciate that any Cas9 known in the art may be utilized in the circuits and methods described herein. Any mutations or modifications to Cas9 such as are known in the art may also be used. Similarly, any sgRNA such as can be designed and will target a promoter of the invention may be used. There are a number of publicly available tools available to help choose and/or design target sequences as well as lists of bioinformatically determined unique gRNAs for different genes in different species, including but not limited to the Target Finder, (e.g., E-CRISP), the RGEN Tools: Cas-OFFinder, the CasFinder: Flexible algorithm for identifying specific Cas9 targets in genomes and the CRISPR Optimal Target Finder.

In some embodiments, the analog signal processing circuit further comprises a nucleic acid sequences encoding at least one of the inputs. In some embodiments, the nucleic acid sequences encoding the input is operably linked to a promoter. In some the input is tuned by adding a molecule that binds to the promoter and modulates translation. In some embodiments, the promoter is not constitutively active. In some embodiments, the expression of an input is tuned by the binding affinity of the promoter to the molecule that modulates translation. In some embodiments, the expression of the input is tuned by mutating or modifying the binding site for the molecule that modulates translation.

In some embodiments, the at least two cooperative inputs are at least two factors that share a common binding site. In some embodiments, the first promoter comprises the common binding site. In some embodiments, the at least two cooperative inputs compete for the common binding site. In some embodiments, the inputs are different molecules that share the same binding site. In some embodiments, the inputs bind different binding sites that overlap in the first promoter. In some embodiments, the two factors only bind to the binding site when both factors are expressed. In some embodiments, the factors modulate transcription. In some embodiments, the factors are transcription factors. In some embodiments, at least one factor modulates transcription. In some embodiments, the analog signal processing circuit further comprises the at least two factors that share a common binding site. In some embodiments, the at least two factors that share a common binding site are a Sigma factor and an anti-Sigma factor. DNA binding proteins with the same or overlapping binding sites are well known in the art, and any such factors where at least one would modulate transcription from the promoter may be used.

In some embodiments, the first promoter operably further comprises a fourth promoter that transcribes in a direction opposite to the transcriptional direction of the first promoter. Nested promoters are well known in the art. Such promoters can translate in the same direction or in opposite directions. Thus, two promoters can exist in the same sequence, but transcribe in opposite directions. Such opposite transcription causes interference between the two promoters as they compete to transcribe. In some embodiments, at least one input binds to active the first promoter and at least one input binds to active the fourth promoter. In some embodiments, binding of at least one of the at least two inputs to the fourth promoter interferes with transcription from the first promoter.

In some embodiments, the present invention provides an analog signal processing circuit comprising:
 a. a first tunable promoter operably linked to a nucleic acid sequence coding for a DNA recombinase;
 b. a second constitutive promoter operably linked to a nucleic acid sequence that when inverted codes for a first output molecule and wherein the nucleic acid sequence is flanked by recognition sites for the DNA recombinase; and
 c. decoy recognition sites for the DNA recombinase.

In some embodiments, the recombinase is a unidirectional recombinase. In some embodiments, the recombinase is a serine recombinase. In some embodiments, the recombinase is a PhiC31 recombinase. In some embodiments, the recombinase is non-reversible. In some embodiments, the recognition sites are identical. In some embodiments, the recognition sites are not identical. In some embodiments, the recognition sites no longer function if inverted. In some embodiments, the decoy recognition sites are inverses of the recognition sites. The location of the decoy sites may be anywhere in the system. In some embodiments, the decoy sites are within a nucleic acid molecule comprising the first tunable promoter. In some embodiments, the decoy sites are within a nucleic acid molecule comprising the second constitutive promoter. In some embodiments, the decoy sites are within a third nucleic acid molecule. In some embodiments, the decoy sites are within: (i) a nucleic acid molecule comprising (a), (ii) a nucleic acid molecule comprising (b), or (iii) a third nucleic acid molecule.

In some embodiments, the constitutive promoter produces no, or very low levels, of the output molecule. In some embodiments, the nucleic acid sequence comprising the output molecule further comprises an insulator component that reduces expression of the inverted output molecule, but not expression of the correctly oriented output. In some embodiments, the insulator is a ribozyme-based insulator. In some embodiments, the insulator is RiboJ. In some embodiments, the insulator is in the UTR of the output sequence. In some embodiments, the insulator is in the 5' UTR of the output sequence.

In some embodiments, the tunable promoter comprises a regulator binding site. In some embodiments, the regulator binding site is a Plux binding site, and the promoter is tunable by addition of AHL, Plux or both.

In some embodiments, in order to ensure low basal transcription from tunable promoters, the protein produced by the promoter comprises a degradation tag. In some embodiments, the degradation tag is a ssrA degradation tag. Such a tag may be used with any of the tunable promoters of the invention.

In some embodiments, the contacting comprises adding an input. In some embodiments, the contacting comprises expressing an input in the cell or circuit. In some embodiments, expressing an input comprises contacting the cell or circuit with a protein that binds to a promoter than transcribes an input. In some embodiments, the contacting comprises transfecting an input into the cell. In some embodiments, the contacting comprises contacting the cell or circuit with a protein that binds an input. In some embodiments, the contacting comprises contacting the cell or circuit with a protein that binds a promoter and induces transcription of an input. In some embodiments, the contacting comprises contacting the cell or circuit with at least one vector comprising a nucleic acid molecule of the invention. In some embodiments, at least one of the nucleic acid sequences of the invention are in a vector. In some embodiments, the nucleic acid sequences are in one vector. In some embodiments, the nucleic acid sequences are in a plurality of vectors. In some embodiments, the invention provides at least one vector comprising the nucleic acid molecules of the invention. In some embodiments, a circuit of the invention comprises at least one vector comprising the nucleic acid sequences of the invention.

Expressing of a gene within a cell is well known to one skilled in the art. It can be carried out by, among many methods, transfection, viral infection, or direct alteration of the cell's genome. In some embodiments, the gene is in an expression vector such as plasmid or viral vector. One such example of an expression vector containing p16-Ink4a is the mammalian expression vector pCMV p16 INK4A available from Addgene.

A vector nucleic acid sequence generally contains at least an origin of replication for propagation in a cell and optionally additional elements, such as a heterologous polynucleotide sequence, expression control element (e.g., a promoter, enhancer), selectable marker (e.g., antibiotic resistance), poly-Adenine sequence.

The vector may be a DNA plasmid delivered via non-viral methods or via viral methods. The viral vector may be a retroviral vector, a herpesviral vector, an adenoviral vector, an adeno-associated viral vector or a poxviral vector. The promoters may be active in mammalian cells. The promoters may be a viral promoter.

In some embodiments, the gene is operably linked to a promoter. The term "operably linked" is intended to mean that the nucleotide sequence of interest is linked to the regulatory element or elements in a manner that allows for expression of the nucleotide sequence (e.g. in an in vitro transcription/translation system or in a host cell when the vector is introduced into the host cell).

In some embodiments, the vector is introduced into the cell by standard methods including electroporation (e.g., as described in From et al., Proc. Natl. Acad. Sci. USA 82, 5824 (1985)), Heat shock, infection by viral vectors, high velocity ballistic penetration by small particles with the nucleic acid either within the matrix of small beads or particles, or on the surface (Klein et al., Nature 327. 70-73 (1987)), and/or the like.

The term "promoter" as used herein refers to a group of transcriptional control modules that are clustered around the initiation site for an RNA polymerase i.e., RNA polymerase II. Promoters are composed of discrete functional modules, each consisting of approximately 7-20 bp of DNA, and containing one or more recognition sites for transcriptional activator or repressor proteins.

In some embodiments, nucleic acid sequences are transcribed by RNA polymerase II (RNAP II and Pol II). RNAP II is an enzyme found in eukaryotic cells. It catalyzes the transcription of DNA to synthesize precursors of mRNA and most snRNA and microRNA.

In some embodiments, mammalian expression vectors include, but are not limited to, pcDNA3, pcDNA3.1 (±), pGL3, pZeoSV2(±), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

In some embodiments, expression vectors containing regulatory elements from eukaryotic viruses such as retroviruses are used by the present invention. SV40 vectors include pSVT7 and pMT2. In some embodiments, vectors derived from bovine papilloma virus include pBV-1MTHA, and vectors derived from Epstein Bar virus include pHEBO, and p205. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

In some embodiments, recombinant viral vectors, which offer advantages such as lateral infection and targeting specificity, are used for in vivo expression. In one embodiment, lateral infection is inherent in the life cycle of, for example, retrovirus and is the process by which a single infected cell produces many progeny virions that bud off and infect neighboring cells. In one embodiment, the result is that a large area becomes rapidly infected, most of which was not initially infected by the original viral particles. In one embodiment, viral vectors are produced that are unable to spread laterally. In one embodiment, this characteristic can be useful if the desired purpose is to introduce a specified gene into only a localized number of targeted cells.

Various methods can be used to introduce the expression vector of the present invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

In one embodiment, plant expression vectors are used. In one embodiment, the expression of a polypeptide coding sequence is driven by a number of promoters. In some embodiments, viral promoters such as the 35S RNA and 19S RNA promoters of CaMV [Brisson et al., Nature 310:511-514 (1984)], or the coat protein promoter to TMV [Takamatsu et al., EMBO J. 6:307-311 (1987)] are used. In another embodiment, plant promoters are used such as, for example, the small subunit of RUBISCO [Coruzzi et al., EMBO J. 3:1671-1680 (1984); and Brogli et al., Science 224:838-843 (1984)] or heat shock promoters, e.g., soybean hsp17.5-E or hsp17.3-B [Gurley et al., Mol. Cell. Biol. 6:559-565 (1986)]. In one embodiment, constructs are introduced into plant cells using Ti plasmid, Ri plasmid, plant viral vectors, direct DNA transformation, microinjection, electroporation and other techniques well known to the skilled artisan. See, for example, Weissbach & Weissbach [Methods for Plant Molecular Biology, Academic Press, NY, Section VIII, pp 421-463 (1988)]. Other expression systems such as insects and mammalian host cell systems, which are well known in the art, can also be used by the present invention.

It will be appreciated that other than containing the necessary elements for the transcription and translation of the inserted coding sequence (encoding the polypeptide), the expression construct of the present invention can also include sequences engineered to optimize stability, production, purification, yield or activity of the expressed polypeptide.

A person with skill in the art will appreciate that a gene can also be expressed from a nucleic acid construct administered to the individual employing any suitable mode of administration, described hereinabove (i.e., in vivo gene therapy). In one embodiment, the nucleic acid construct is introduced into a suitable cell via an appropriate gene delivery vehicle/method (transfection, transduction, homologous recombination, etc.) and an expression system as needed and then the modified cells are expanded in culture and returned to the individual (i.e., ex vivo gene therapy).

In some embodiments, the detecting comprises quantification of the output molecule. In some embodiments, the quantification comprises measuring the fluorescence of the output molecule. Methods of protein quantification are well known in the art, and include but are not limited to immunoblotting, ELISA, FACS to name but a few.

In some embodiments, the digital output is either a positive or a negative output. In some embodiments, the output is ether present or absent. In some embodiments, the method further comprises tuning a threshold for converting the analog input into a positive digital output. This threshold is the value at which the digital output is present. In some embodiments, the tuning comprises tuning expression of at least one of the at least two regulators. In some embodiments, the tuning comprises tuning a binding efficiency of at least one of the at least two inputs to a binding site. In some embodiments, the tuning comprises tuning a binding efficiency of at least one of the at least two regulators to a binding site. In some embodiments, the tuning comprises adding a molecule that binds to the regulatory sequence. In some embodiments, the tuning comprises adding a molecule that binds to the first output molecule and alters binding of the first output molecule to the third promoter. In some embodiments, the tuning comprises at least one of (a) tuning expression of at least one of said at least two regulators; (b) tuning a binding efficiency of at least one of said at least two inputs to a binding site; (c) tuning a binding efficiency of at least one of said at least two regulators to a binding site; (d) adding a molecule that binds to said regulatory sequence; and (e) adding a molecule that binds to said first output molecule and alters binding of said first output molecule to said third promoter.

Mapping Neural Networks to Molecular Networks

The basic computational element in ANNs is the perceptron (FIG. 1A), which performs three operations: (i) summing all the inputs in analog fashion, (ii) multiplication of each input ($x_i$) by analog scalar ($w_i$) that represents the synaptic (strength) weight, and (3) a non-linear neural activation (thresholding). The corresponding perceptron's output is given by:

$$z = \begin{cases} "1" & \sum_i w_i \cdot x_i - y_{th} \geq 0 \\ "0" & \text{otherwise} \end{cases} \quad (1)$$

Figure 1B:
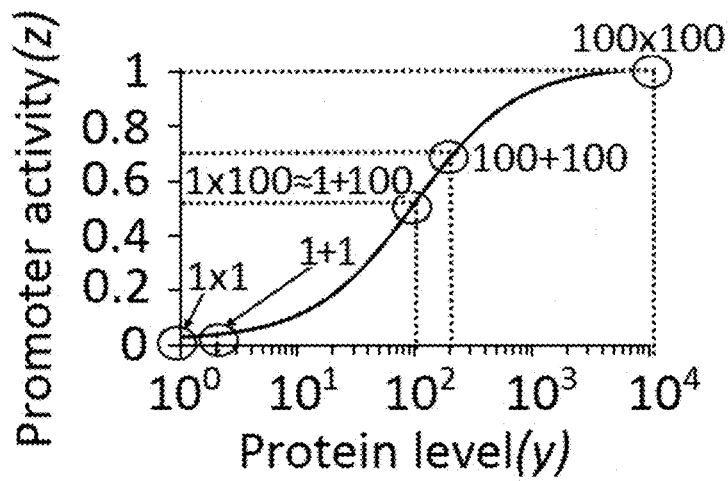
Figure 1C:
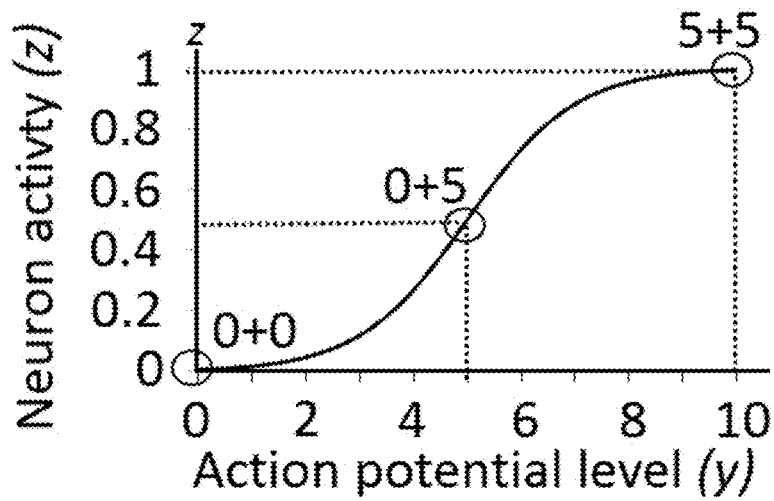
Figure 1D:
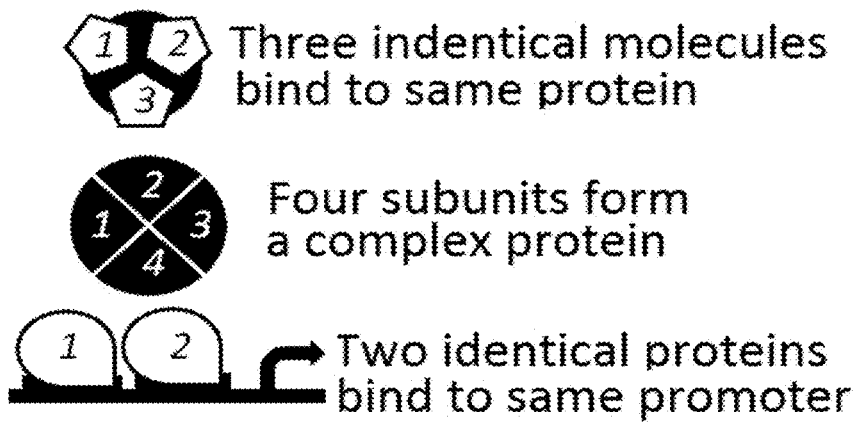

In equation (1), a shifted signum (step) activation function was used. The perceptron is an abstract model that can capture the computational power of biological neurons. Because, as was previously shown, biological and neural architectures share many features, a novel simple transformation between the basic computational structure of perceptron and molecular processing unit can be discerned. Accordingly, an interaction between proteins and DNA that controls the promoter activity ($P_r$) can be viewed either as a node or as an activation function which, in turn, can be simply described by a Michaelis-Menten model. Promoter is a region of DNA that initiates transcription of a particular gene. In human genetic circuits, transcription is followed by translation that leads to a protein synthesis. A sigmoid function can be then used to describe the promoter activity:

$$P_r = P_{on} \frac{e^{\ln(y/K_d)}}{1 + e^{\ln(y/K_d)}} + P_{off} \quad (2)$$

where, $K_d$ is a dissociation constant of protein (y) binding to DNA, $P_{off}$ is the basal level, and $P_{on}$ is the maximum activity achieved by the system. In equation (2), a single binding site in the promoter was assumed. The promoter activity can be simply viewed as a sigmoid function in a log-linear domain. As a first-order approximation, for $y \geq K_d$ or $y \leq 0.1\ K_d$, the promoter activity asymptotically accepts two discrete levels ($P_{on}$ and $P_{off}$). Now, it may be assumed that y is represented by a combinational analog function of input vector, (y is a multi-protein complex formed by other proteins that bind together). In this case, and in analogy to perceptron, y will be the inputs' multiplication outcome $y = \Pi_i x_i$ rather than their summation outcome ($y = \Sigma_i x_i$ Equation 1 when $w_i = 1$). As can be gleaned from FIG. 1B that, to activate the log-linear sigmoid function from a low to a high level, the two inputs must be multiplied by each other rather summated; summing them could activate the linear-linear sigmoid function from a low to a high level (FIG. 1C). The next chronological step is to define the strength (weight) of the inputs. While biologists have shown that "two is better than one," little is known about the design principles of cooperative binding, a phenomenon that occurs in biochemistry to enhance and stabilize the biological complexity of reactions, for scaling the computational complexity of biological networks in living cells. There are three main models of cooperativity in living cells (FIG. 1D): (i) identical molecules bind to a protein that contains multiple binding sites, (ii) protein subunits bind to form a multiprotein complex (quaternary structure); the subunits are regulated by the same open reading frame/promoter/operon, (iii) identical proteins/transcription factors bind to promoters with multiple binding sites. In the three models, cooperativity often increases the affinity for binding of the other subunits and is modeled by a power law function ($x^n$, where n is known as the Hill coefficient, which denotes the effective number of identical units that interact). From an engineering perspective, cooperativity in living cells can be described as the number of independent components that collectively act, analogous to the computational role of synapses in ANNs. Thus, the strength of every input (weight) activated by a log-linear sigmoid will be determined by the cooperativity, is given by:

$$z = \begin{cases} "1" & \frac{\Pi_i x_i^{n_i}}{y_{th}} > 1 \\ "0" & \text{otherwise} \end{cases} \quad (3)$$

or $$z = \begin{cases} "1" & \sum_i n_i \cdot \ln(x_i) - \ln(y_{th}) > 0 \\ "0" & \text{otherwise} \end{cases}$$

Figure 1E:
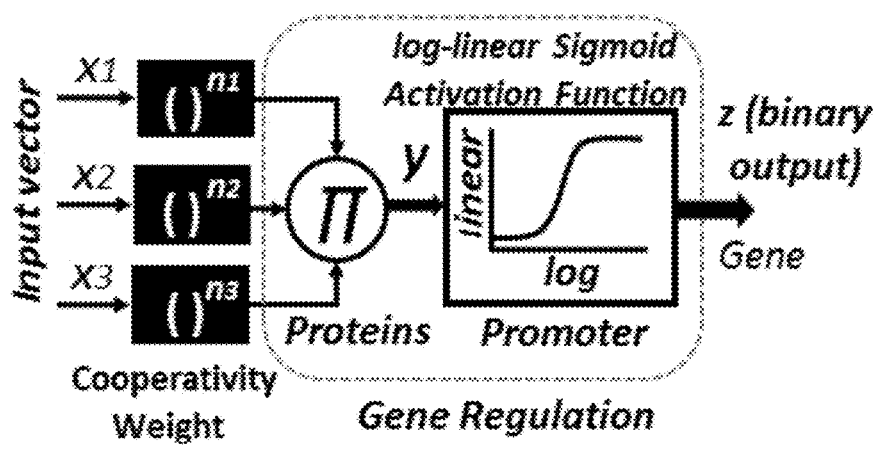
Figure 1F:
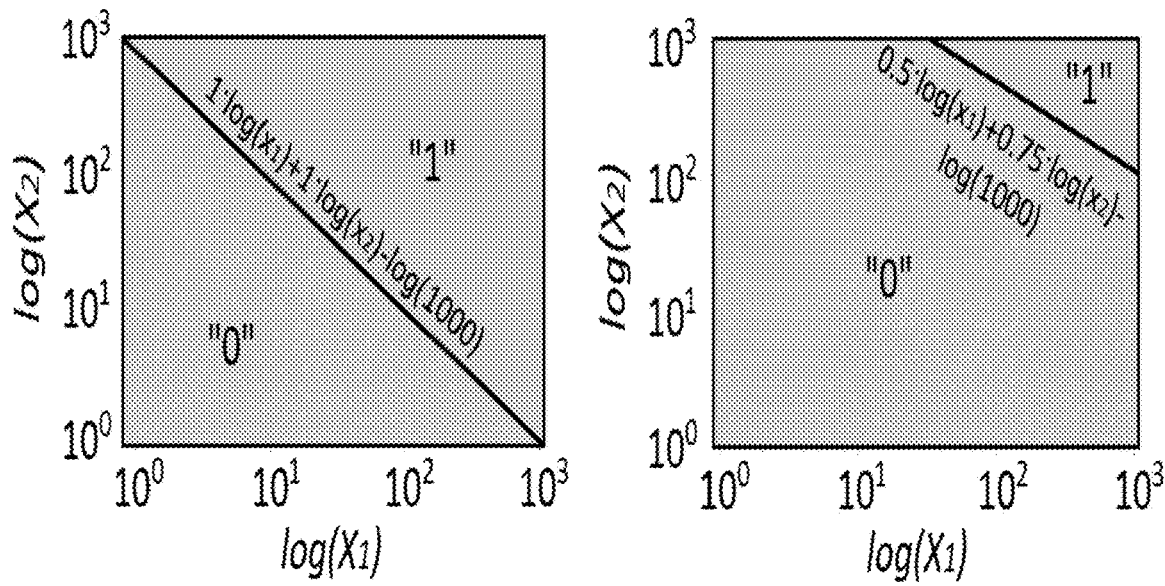

In analogy to the perceptron, it was assumed that the activity of the promoter in equation (3) is a signum function, however in natural and synthetic systems, it is approximated as a log-linear sigmoid function (Hill-function). By this, there was developed a new model, termed 'perceptgene,' inspired by molecular biology (FIG. 1), with powerful computational abilities. Equation (3) is equivalent to equation (1) (perceptron/linear-classifier) in a log-linear domain, as illustrated in FIG. 1E. The perceptgene is inspired by molecular biology and has a computational process identical to that of the perceptron, i.e., consisting of three operations: (i) multiplication of all the inputs in analog fashion (this process is mainly implemented by binding reactions), (ii) each input ($x_i$) is invoked by a power law function with a coefficient n, that represents the cooperativity binding reaction, and (iii) a log-linear activation function that is implemented by promoter activity or a bio-enzymatic reaction (thresholding). The corresponding binary-fashion perceptgene output depends on the threshold accordingly. The simulation results (FIG. 1F) of equation (3) suggest that the perceptgene is a type of a linear classifier in a log-linear domain and, in contrast to the perceptron, a small change in the cooperativity weight causes large separability. In summary, a perceptron is a binary classifier that makes its decision based on a linear predictor function combining a set of weights with the input vector. Analogously, the perceptgene is a binary classifier that makes its decision based on a log-linear predictor function, multiplying a set of non-linear weights with the input vector.

Synthetic Molecular Networks (SMNs) in Living Cells

Figure 2A:
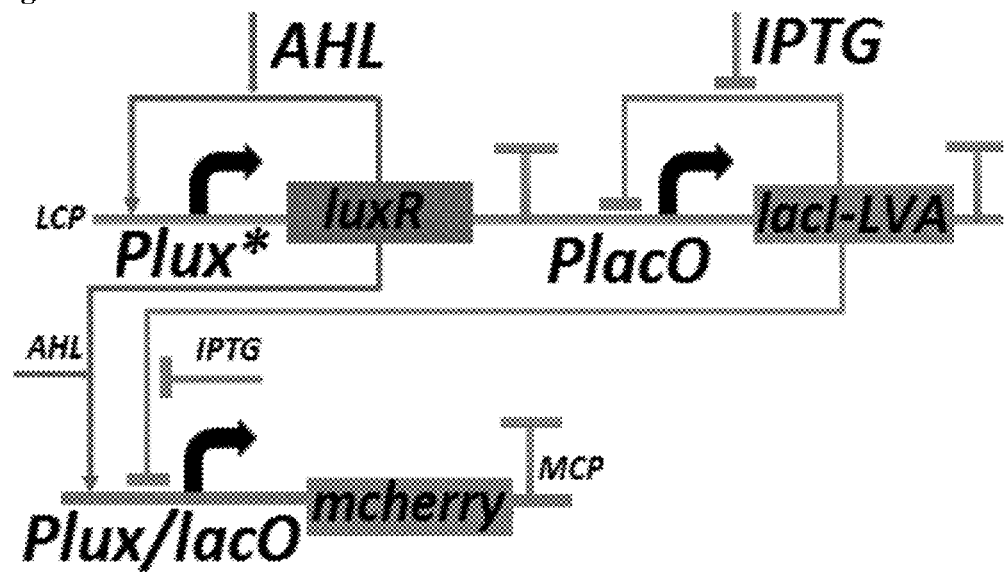
FIGS. 2A-H: (2A) & (2B) construction and experimental results of a genetic analog multiplier based on a hybrid promoter in E. coli, (2C) & (2D) construction and experimental results of a genetic analog multiplier based on a riboswitch in E. coli, (2E) & (2F) construction and experimental results of a perceptgene in E. coli, (2G) simulation results of summation, and (2H) simulation results of the perceptron.
Figure 2B:
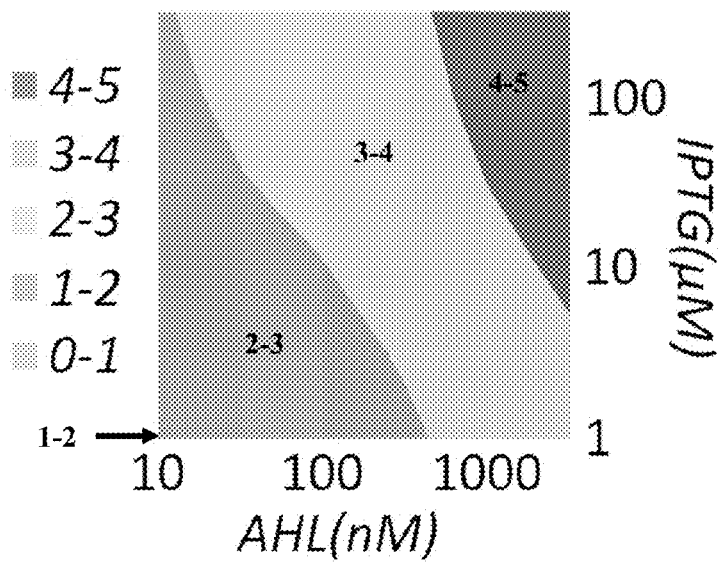
Figure 2C:
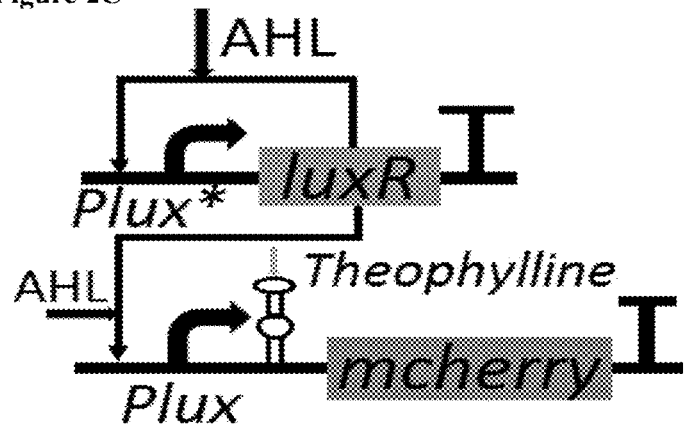
Figure 2D:
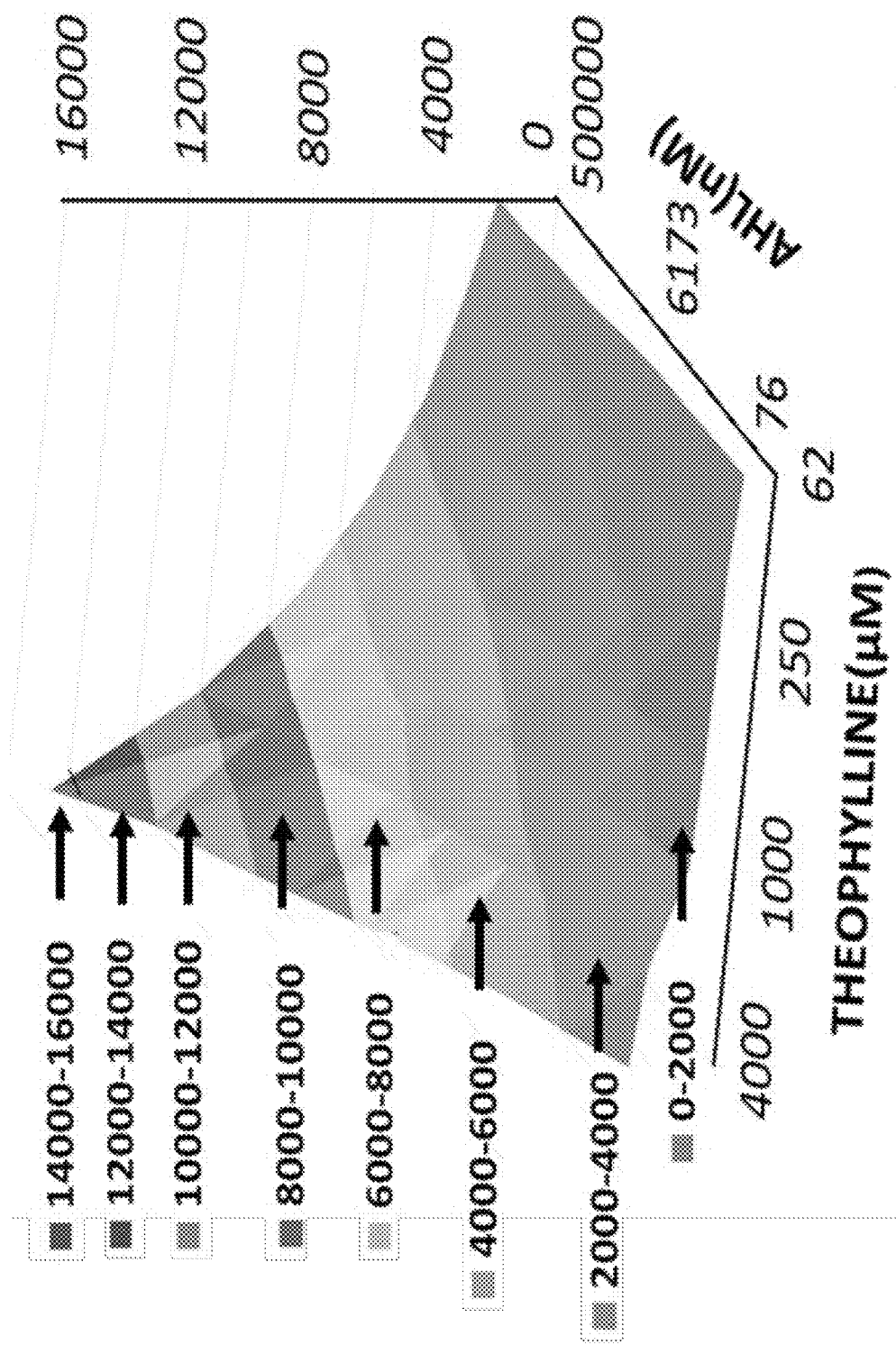
Figure 2E:
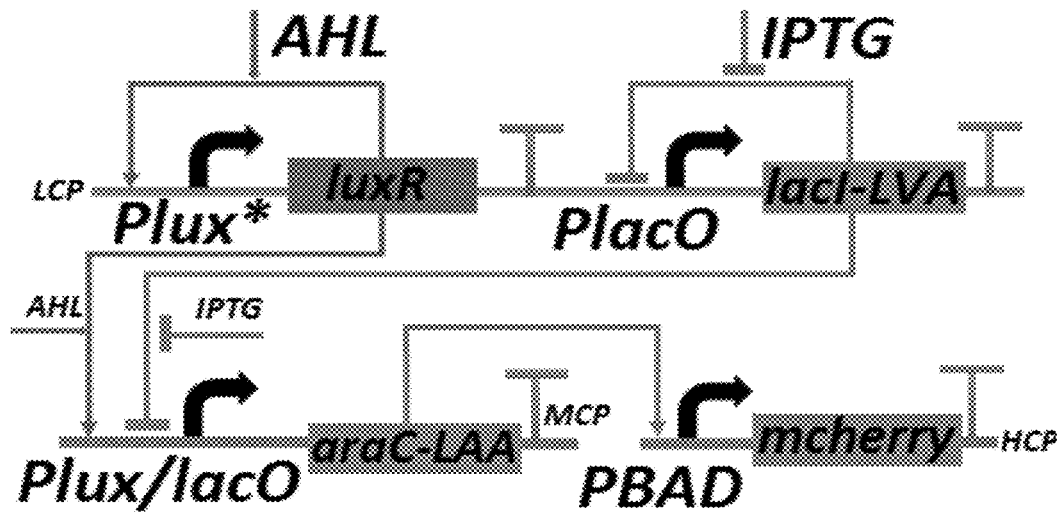
Figure 2F:
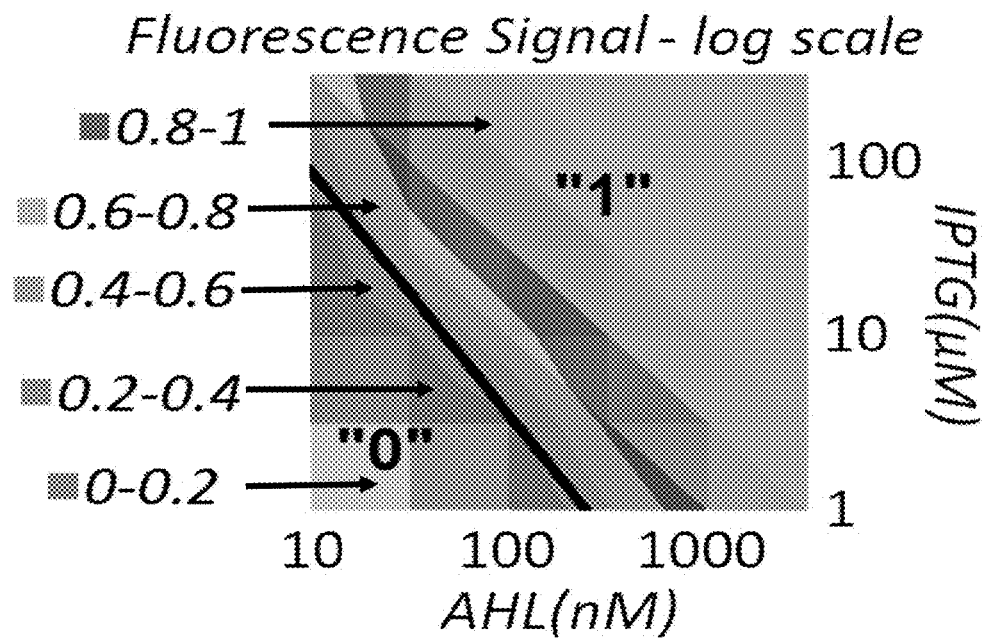
Figure 2G:
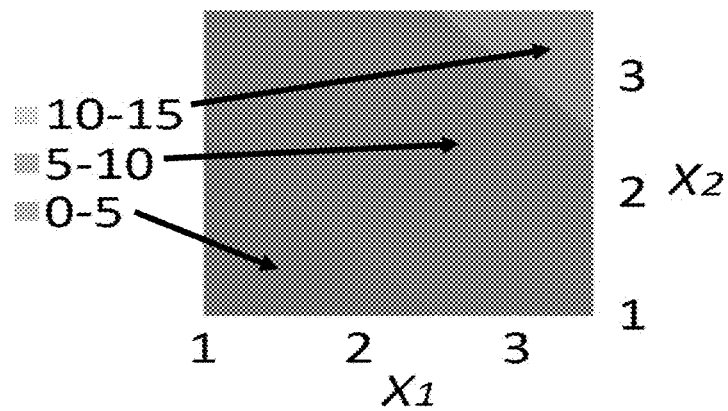
Figure 2H:
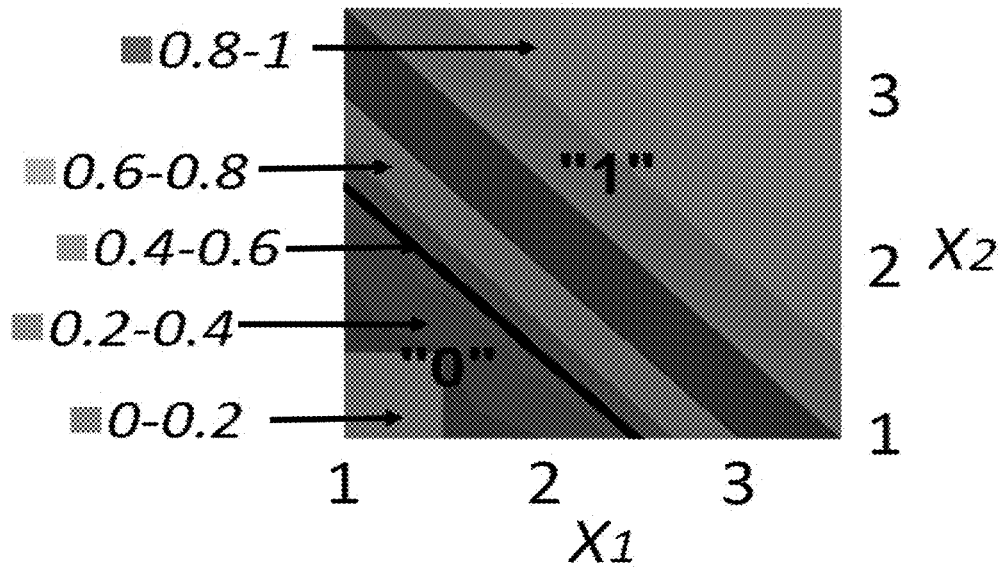

SMNs attempt to transfer principles of neural networks into biological design, to build large-scale robust-intelligent living systems. As a proof of concept, a synthetic perceptgene was constructed in living cells, which acts as a log-linear classifier (FIG. 2A-H). As a first step, there will be described two different systems performing a multiplication with weighted cooperativity. The systems accept AHL and IPTG chemicals as inputs and express a fluorescent protein (GFP or mcherry) as an output. The first system is implemented by a well-known synthetic hybrid promoter consisting of the LuxR activator and LacI repressor. In asymptotic boundary conditions, the hybrid promoter is only activated in the presence of LuxR and absence of LacI at the promoter. AHL and IPTG molecules bind to LuxR and LacI, respectively, and change their protein structure, which change protein's binding activity to the promoter. Asymptotically, at high concentrations of both AHL and IPTG, LuxR is bound and LacI is free, therefore, the promoter is activated. This circuit is widely used in synthetic biology to implement AND logic gate. To achieve an analog multiplication rather than an AND logic gate, an ssrA degradation tag was added to the LacI repressor, which reduces the life-time and the copy number of LacI in steady state. Furthermore, graded positive feedback (PF) and negative feedback (NF) loops were used to regulate the expression of LuxR and LacI, respectively, thereby strikingly increasing the dynamic ranges of AHL and IPTG input. The graded PF loop was achieved by creating random mutations in the LuxR-DNA binding site sequence within the promoter, causing reduced binding efficiency of LuxR to promoter. The NF and PF loops were cloned on low copy number of plasmids (LCP) and the hybrid promoter was cloned on a medium copy number of plasmids (MCP), which acts as a shunt. The purpose of adding a shunt is to prevent oscillations of the NF loop and to broaden the dynamic ranges of transcription factors (TFs) inputs. The experimental result of the analog multiplier based on a hybrid promoter is presented in FIG. 2B. The effective Hill coefficients of the system is 0.5 for AHL and 0.7 for IPTG. In natural systems, two AHL molecules bind to one LuxR protein, and one complex AHL-LuxR binds to the promoter, thus, the Hill coefficient of the LuxR system should theoretically be equal to 2, however, the inherent negative feedback in the binding reactions between the LuxR and AHL (the concentration of total LuxR is constant) reduced it to lower values. Furthermore, in our systems, the mutated PF loop and hybrid promoter also reduced the Hill coefficient. A similar explanation could be given for IPTG-LacI cooperativity. The second multiplier system is implemented in the transcription-translation level using LuxR and Riboswitch (FIG. 2C). The system has two inputs, theophylline and AHL (FIG. 2D). Theophylline is a small molecule that interacts with the untranslated region of mRNA (5' UTR), and regulates the translation process of targeted gene expression. The Hill coefficient of such a system is 0.5 for theophylline and 0.2 for AHL, unequal to the first system. This can be explained because both systems were cloned on different copy number shunt plasmids. Eventually, a perceptgene in living cells was implemented by cascading a log-linear sigmoid activation function to the analog multiplier. This was achieved by replacing the output of the $P_{lux/lacO}$ hybrid promoter with the araC gene and adding the $P_{BAD}$ promoter that controls the output GFP protein (FIG. 2E). An araC was used as an activator, by adding arabinose to the cell culture. The arabinose-AraC complex binds strongly to the $P_{BAD}$ promoter, eliciting a sharp input-output transfer response. Thus, it can act with a log-linear sigmoid behavior. FIG. 2F shows experimental results of the perceptgene in living cells; the activation function that is implemented by the $P_{BAD}$ promoter converts the analog behavior of the multiplier to a first-order binary classifier. To better understand these results, a linear domain classifier (perceptron) was simulated by transforming perceptgene parameters (weights, threshold and scale) from log scale to linear scale. Our simulation results show that a summation in linear scale (FIG. 2G) has a similar behavior to a multiplication in log-scale (FIG. 2B), and that a perceptron (FIG. 2H) based on a sigmoid activation function, has a similar behavior to a perceptgene based on a Hill function (FIG. 2E).

An Analog Synthetic Parts Library

Figure 3A:
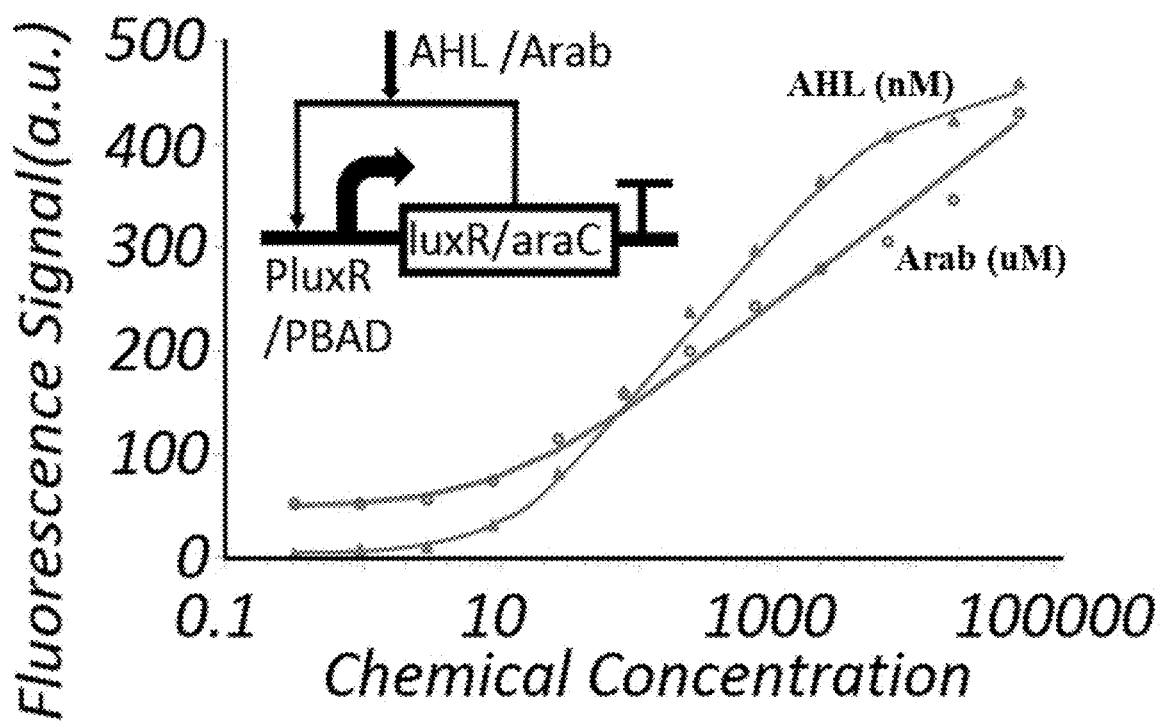
FIGS. 3A-F: (3A) PF and shunt circuit for linearization, (3B) & (3C) proposed analog multiplier based on T7 RNAp and CRISPR system, respectively, (3D) PF and shunt circuit for cooperativity weight fine-tuning, (3E) Control of the threshold of the perceptgene based on competition between promoters, and (3F) Control of the threshold of the perceptgene based on decoy binding sites.

The experimental results of hybrid promoters and other complex proteins have been shown in several synthetic biology works, which aimed to realize 'AND-logic-gate', binging researchers construct them mainly by reducing the input dynamic range of these synthetic parts. The novelty of the present invention lies in exploiting the analog complex operations naturally existing in living cells, e.g., binding reactions that mimic analog multiplication, and integrating them with digital components, to achieve very powerful computing networks (perceptgene in SMNs). As a first step, a library of analog synthetic parts was built with a wide input dynamic range, using feedback loops and log-linear input-output transfer functions. The synthetic parts performance was improved upon by developing new methods for increasing their input dynamic range. For example, FIG. 3A shows new graded PF circuits which have a very wide input dynamic range, with five orders of magnitude for AHL-LuxR and arabinose-AraC. In some embodiments, these circuits may be further improved by more than one order of magnitude. These results were based on an analytical model of graded PF (see, e.g., gates in single cells. *Nature*. 2012; 491(7423):249-253. doi:10.1038/nature11516.

46. L R, Y R. Noise Tolerance Analysis for Reliable Analog and Digital Computation in Living Cells. *J Bioeng Biomed Sci*. 2016; 6(2). doi:10.4172/2155-9538.1000186). Furthermore, well-known methods in synthetic biology were applied to either control the slope of input-output transfer function or to adjust the basal level of our analog synthetic biology parts. This method may then be generalized to other synthetic parts (e.g., T7 RNA polymerase, CRISPR, Segma Factor, LacI and others).

A Library of Analog Multipliers and Control the Cooperativity Weights

Figure 3B:
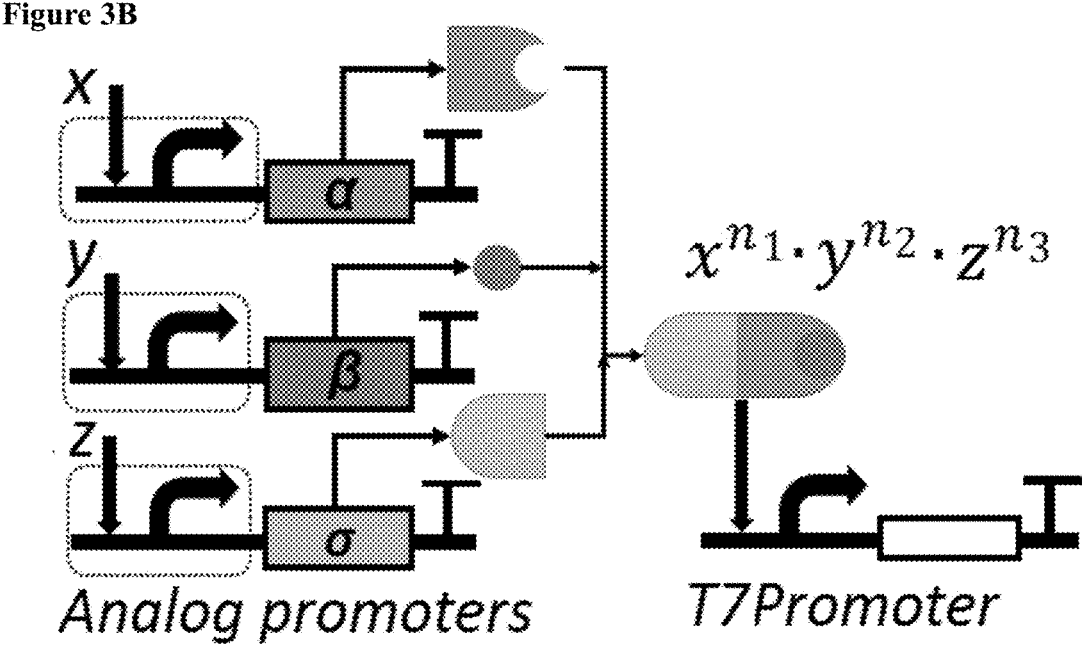
Figure 3C:
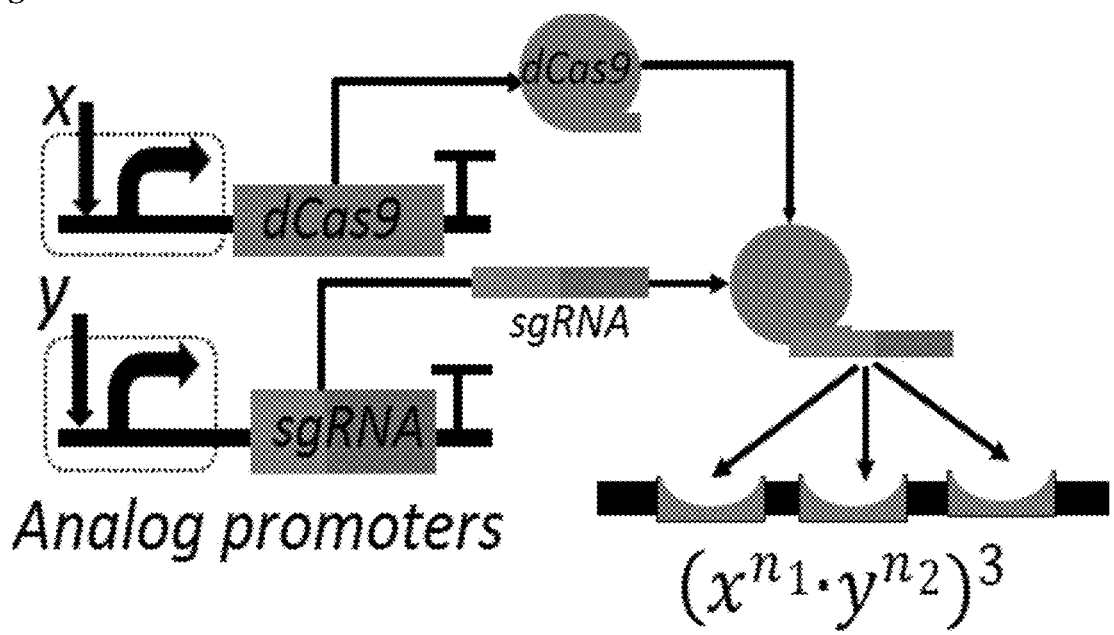

It was shown above that genetic circuits that inherently exhibit binding reactions in living cells, can be applied to construct analog multipliers (FIG. 2). Previously, synthetic biologists have successfully developed several robust synthetic systems that demonstrate binding reactions in living cells (bacteria, yeast and mammalian cells). Thus, these systems may be further used to build a library of analog multipliers with programmable cooperativity weights. Three systems may be thus used:

The T7 RNA polymerase (RNAp) system, which is widely used in synthetic biology and has recently been successfully divided to several fragments that have to be functionally co-expressed. This system mainly consists of three subunits: (i) σ-fragment (DNA-binding loop), (ii) β-core fragment and (iii) α-fragment. FIG. 3B illustrates an example of construction of an analog multiplier with three inputs. In the proposed circuit, the cooperativity weights will be set by the binding reaction and the analog promoters. When two subunits of T7 RNAp are regulated with the same analog promoter, the cooperativity weight will be doubled. This system demonstrates very low toxicity when cloned in E. coli;

CRISPR, which is another synthetic biology system widely used to regulate gene expression, was recently constructed to implement an AND-logic gate. The CRISPR system consists of dCas9 protein and small guide RNAs (sgRNAs), both of which have to be expressed to function. In this research, we will exploit the interaction between dCas9 and sgRNAs to build an analog multiplier. This system has several advantages; (i) the system can be used a repressor or activator when the dcas9 is fused to the omega (w) subunit of RNAp, (ii) the sgRNA can be programmed to interact with different genetic binding sites. In this case, the binding efficiency of the interaction between the dCa9 protein and sgRNA can be programmed by running a random mutation on the sgRNA sequence, which is considered a simple technique for programming cooperativity binding. FIG. 3C shows a circuit proposed for construction of an analog multiplier with programmed cooperativity weights based on the CRISPR system. Moreover, in this research we will use different methods to generate libraries of split dCas9 protein into several subunits (e.g., incremental truncation, multiplex inverse PCR and others). There are some challenges in using CRISPR system. For example, when dCas9 or sgRNA is combined with a strong promoter, it might cause severe growth defects and toxicity to cells; and Orthogonal O-ribosome, which is another synthetic biology system that we will use to construct an analog multiplier. Recently, it was applied to construct an AND logic gate with two inputs. The system consists of two inputs that must be co-expressed to receive a signal. One input will regulate the transcriptional process, while the second will regulate the translational process. We have applied this system in our lab and got reasonable results (ratio between gene expression of high level and low level ~60 fold). In brief, the O-ribosome efficiently and specifically translates its cognate orthogonal mRNA (O-mRNA), which is not a substrate for the endogenous wild-type ribosome.

All these systems will be very useful in scaling gene networks based on SMN architecture.

NF and PF Loop for Cooperativity Weight Fine Tuning

Figure 3D:
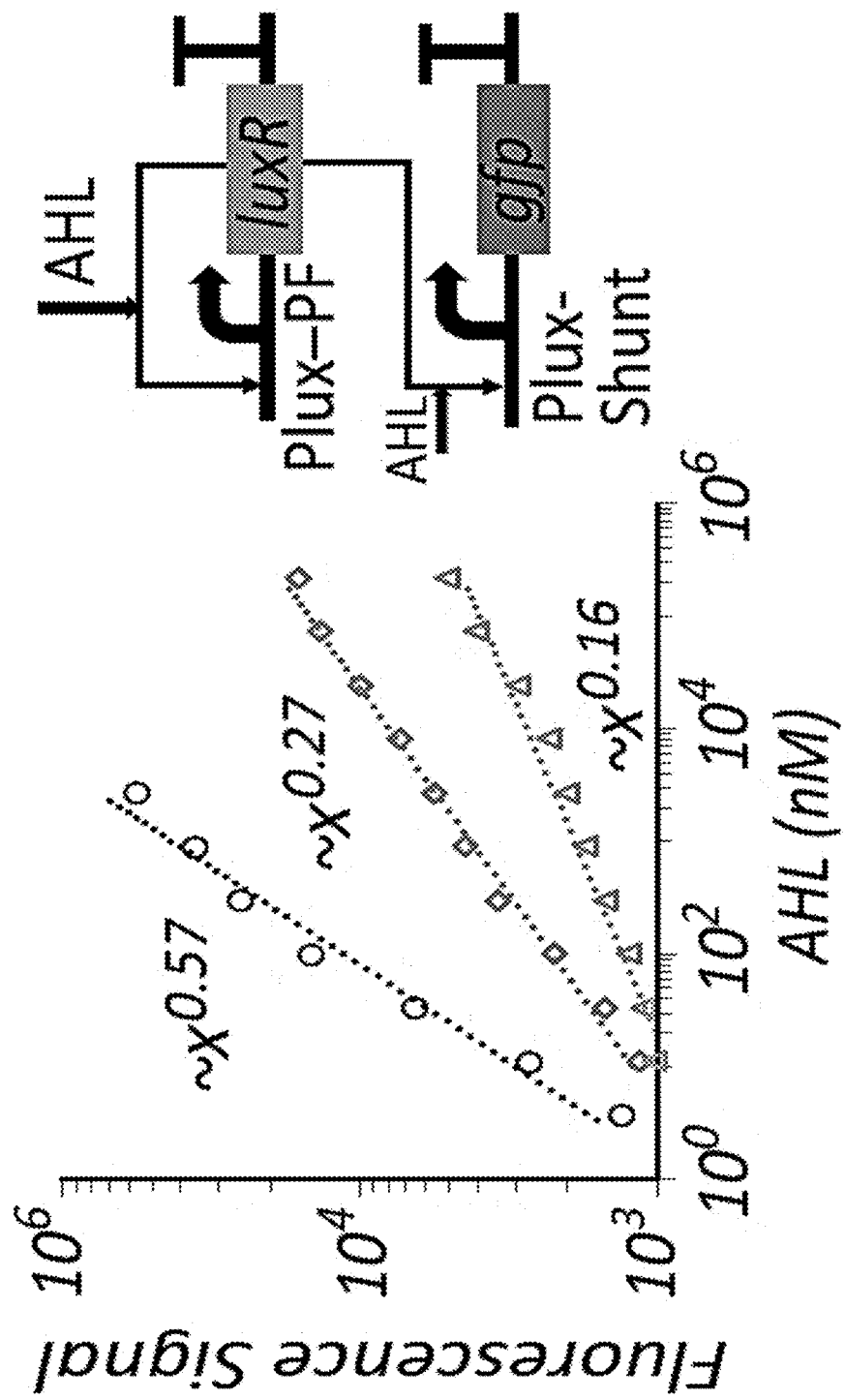

The simulation of the perceptgene (FIG. 1F) showed that small changes in the cooperativity weight leads to large changes in the system function. Therefore, it is highly important to optimize the cooperativity weight of the perceptgene when building large-scale SMNs. To achieve that, PF and NF loops may be used. FIG. 3D shows that by altering the promoter binding efficiency of the PF loop versus the shunt, we can tune the Hill coefficient to different values. The same effect is achieved by altering the strength of the NF loop (data not shown).

Programing the Activation Function of Perceptgene

Figure 3E:
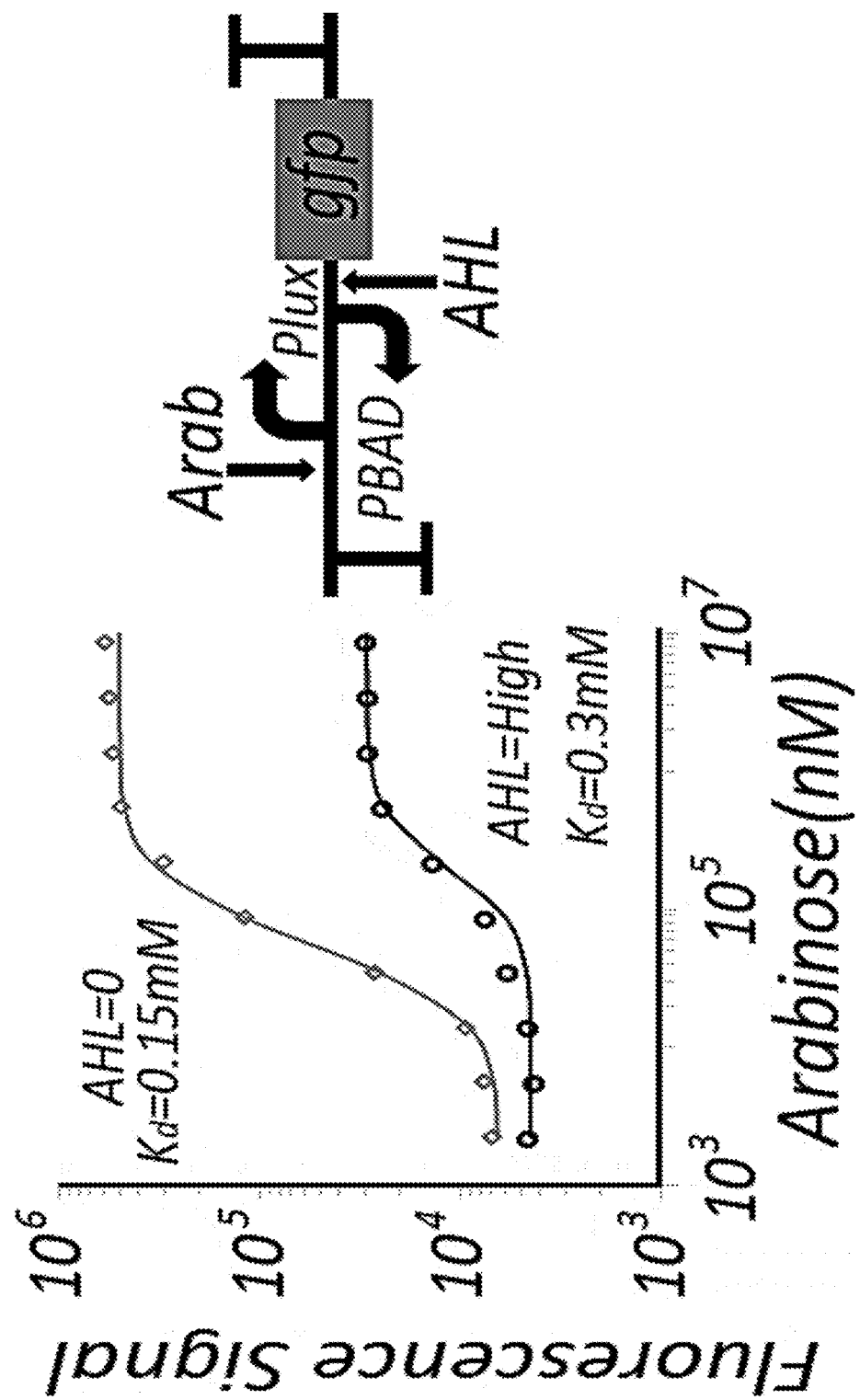
Figure 3F:
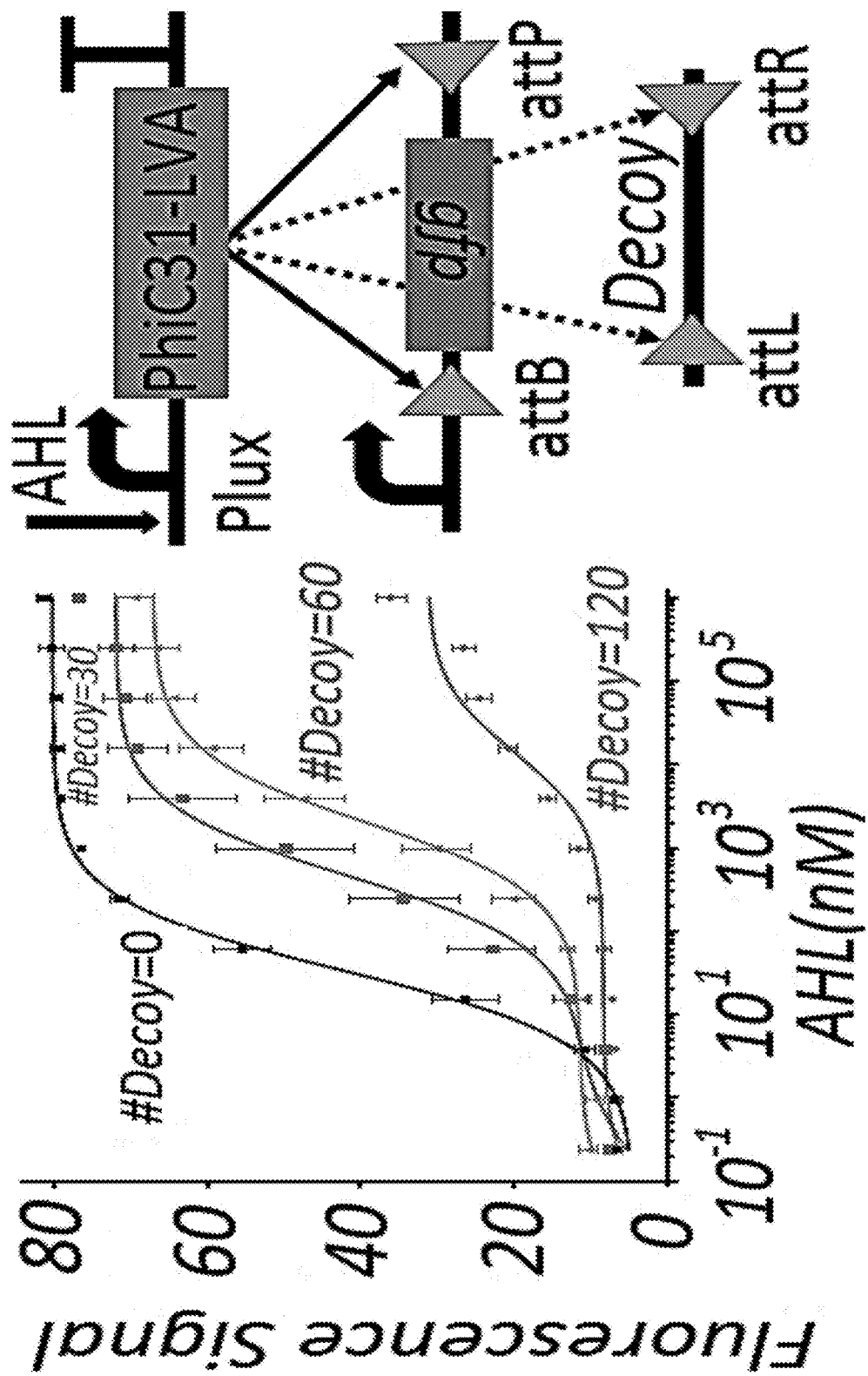

The threshold of the activation function in the perceptron or perceptgene mainly sets the "0" and "1" logic levels of the analog inputs. Moreover, its value significantly impacts signal propagation in ANNs or AMNs, system performance, noise margin and system resource consumption. For example, a system with a low threshold and low cooperativity weights can achieve the same performance of a system with a high threshold and high cooperativity weights. However, the first system consumes fewer resources than the second. Thus, it may be advantageous to control the threshold of the perceptgene activation function. To this end, three synthetic biological systems may be used which exploit a competition between parts: (i) competition between promoters, (ii) competition between proteins and (iii) competition between binding sites. FIG. 3E shows two promoters that are located in opposite orientation to each other. Experimental results (FIG. 3E) shows that there is interference between the convergent promoters, which causes a shift in the threshold or effective dissociation constant. Transcriptional interference between convergent promoters has been reported in biology. The next system will be based on competition between transcription factors and dCas9 on the same binding site. This system is expected to shift the threshold as a function of dCas9 level. The dCas9 protein can be programmed to bind to any binding site that includes a specific DNA sequence called PAM. In this way, the same promoter can be used with different dissociation constants. The same behavior can be achieved by competition between the Sigma and anti-Sigma factors. These systems have only three, rather than four, thermodynamic states: (i) No transcription factors are bound, (ii) only the input transcription factor-RNA polymerase complex is bound and (iii) only the competitor transcription-RNA polymerase complex is bound. This simple model shows a shift in the threshold value as a function of the competitor protein level. The latter system is based on a recombinase protein and decoy binding sites. Recently, it has been shown that repetitive stretches of DNA that contain transcription factor binding sites, can sequester transcription factors and act as a decoy, yielding an increase in the effective dissociation constant of input-to-output transfer functions. A PhiC31 unidirectional serine recombinase was used, which targets its own cognate pair of non-identical recognition sites, known as attB and attP. PhiC31 can irreversibly invert or excise DNA on the basis of the orientation of the surrounding pair of recognition sites. The inverted recognition sites are known as attL and attR. The system consists of:

phiC31 cloned under the control of the mutated $P_{lux}$ linearization circuit to achieve fine-tuned gene expression with a broad region of linearity. To ensure low basal transcription levels in the absence of input (AHL), there was added an ssrA degradation tag (AAV) to PhiC31 recombinase proteins;

a constitutive promoter proD, which regulates the expression level of the inverted green fluorescent protein gene (gfp), which is located between the two recognition sites attB and attP, and is cloned on a single copy number plasmid backbone BAC (FIG. 3F). In the absence of PhiC31, proD regulates the inverted gfp gene, that gives a background GFP signal (very low GFP). In the presence of PhiC31 within the cell, the PhiC31-attB and PhiC31-attP complexes flip the inverted gfp gene, such that it will be in the same orientation as the proD promoter, resulting in a high GFP signal. A ribozyme-based insulator component (RiboJ) was added to the 5' UTR of the gfp gene to reduce the background signal; and Decoy binding sites to sequester the PhiC31 recombinase protein. This was achieved by introducing the two inverted recognition sites, attL and attR, into medium and high copy number plasmids (MCP and HCP), shifting the AHL-to-GFP transfer function (FIG. 3F).

A Perceptgene with a Negative Weight

ANNs often include positive and negative weights. For example, to construct the XOR logic gate (exclusive operation), three layers of a perceptron with negative and positive weights need to be cascaded. Therefore, in some embodiments, a perceptgene may be built in living cells with negative weights ($x^{-n}$). This is achieved by applying two methods. The first one is based on integration of repressors in an analog multiplier, to yield an analog divider rather than analog multiplier. The second method is based on controlling the threshold. By reviewing equation 3 above, it can be seen that a negative weight can be implemented by controlling the threshold of the perceptgene by the system inputs. Two methods to achieve this goal have been described herein above.

SMNs with Emergent Cooperative Analog Computational and Evolutionary Abilities

Figure 4A:
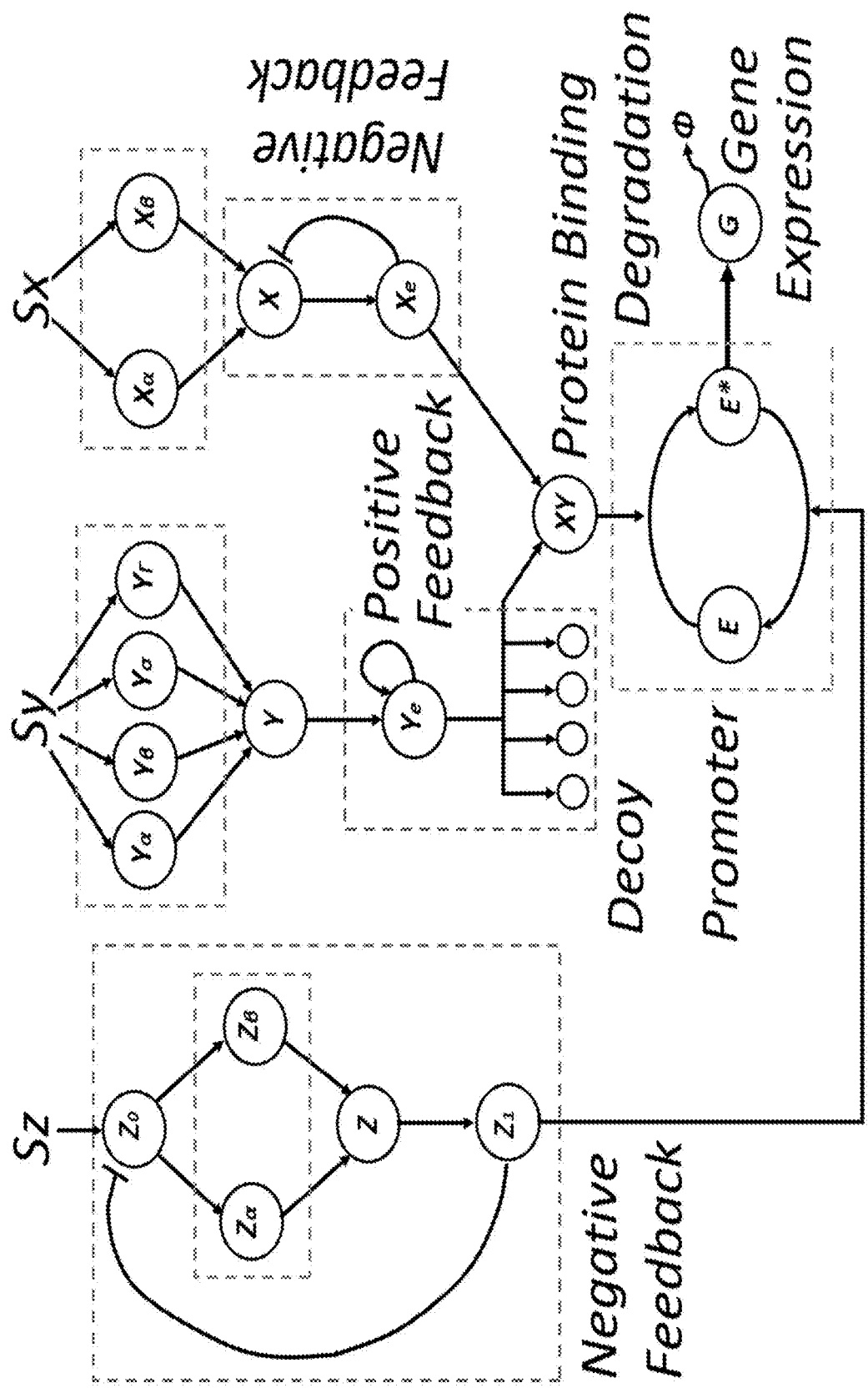
FIGS. 4A-D: (4A) and (4B) mapping SMN to ANN, the NF and PF in the SMN are used to tune cooperativity, (4C) stochastic simulation results of the perceptgene when intrinsic noise is added to the multiplication of Equation 3, and (4D) Stochastic simulation results of the perceptron when intrinsic noise is added to the summation of the equation, and a log-linear activation function is used.
Figure 4B:
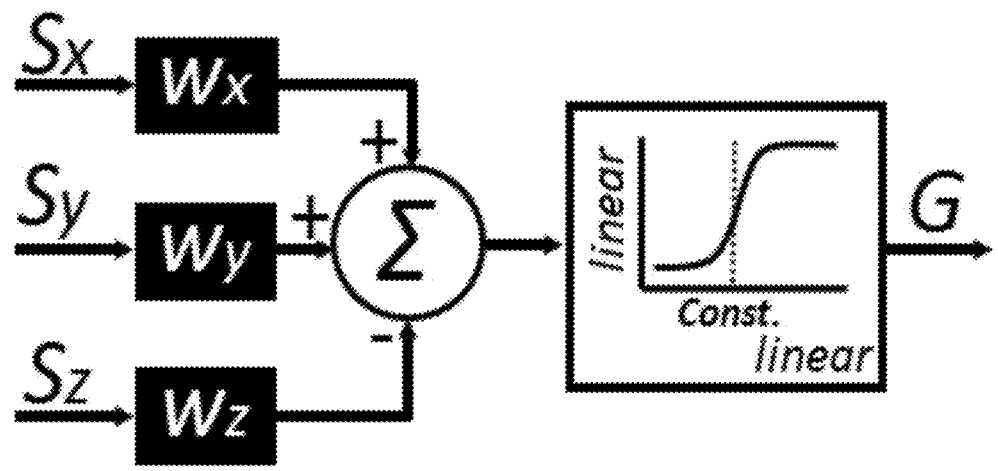
Figure 4C:
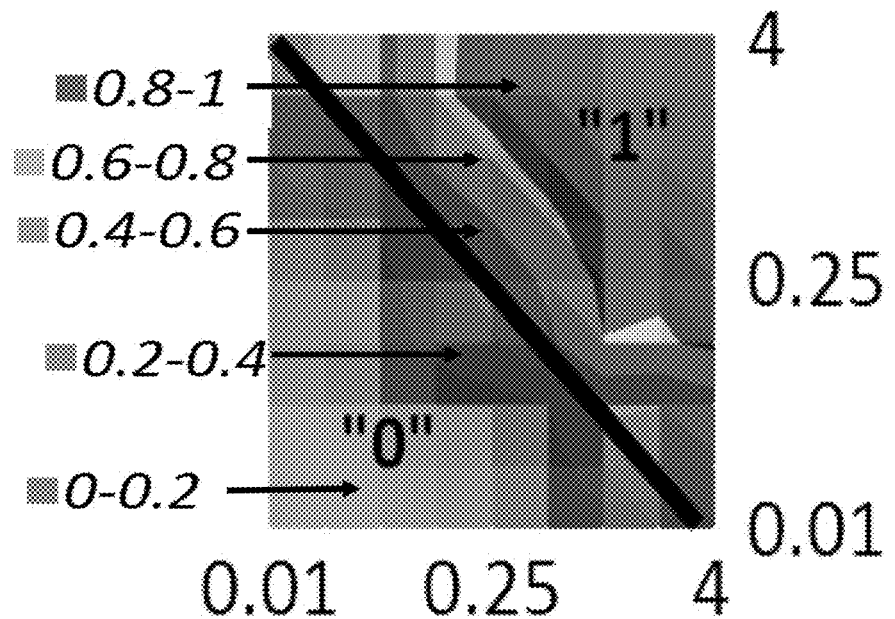
Figure 4D:
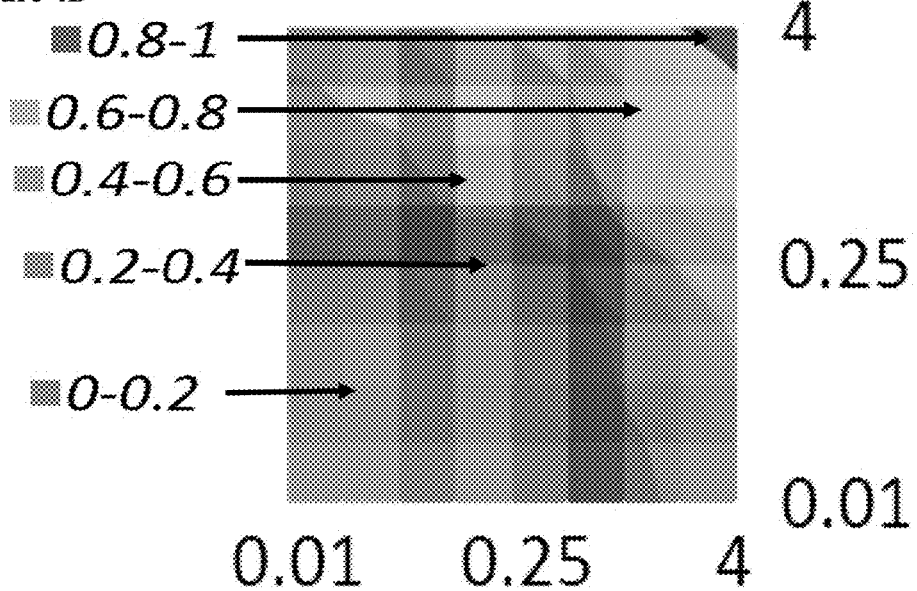

FIG. 4A shows one example of mapping an ANN to an SMN, and vice versa. By mapping the complex biochemical reaction network (FIG. 4A) to a linear domain, the function of this network can be simplified as a linear classifier (FIG. 4B) using three inputs with different weights ("1" if $w_x \cdot S_x + w_y \cdot S_y - w_z \cdot S_x >$ Cosnt, "0" otherwise). The threshold constant is set by the forward and reverse rates of the bio-enzymatic reaction. PF and NF loops are used to tune the weights $1 \le w_x \le 2$, $3 \le w_y \le 4$ and $1 \le w_z \le 2$. Below, it will further be shown that SMNs can be integrated into more complex networks to build large-scale biological systems with minimal requirements of host cell resources. These are intelligent parallel processing units that can execute sophisticated computational and learning (evolutionary) functions in living cells and electronics. Details about the construction of these systems will be provided after first establishing the theoretical framework for mapping SMNs and biological systems to ultra-low power electronics. Naturally, biological signals propagate through networks with random fluctuations, which can be described by a Poisson process. FIGS. 4C and 4D show stochastic simulation results of two systems; perceptgene (two inputs that are fed into a log-linear activation function are multiplied), and perceptron (two inputs that are fed into a log-linear activation function are summed up). The simulation results show that perceptron fails to act as a binary classifier (there are no clear "0" and "1" states—FIG. 4D) when intrinsic noise is added to the system. By contrast, a perceptgene has clear "0" and "1" states (FIG. 4C).

Mapping Molecular Networks to Nanoelectronics

Neuromorphic engineering is a multidisciplinary field that interpolates/extrapolates principles of neural networks into/from electronics. For example, it has been shown that a BJT/MOS-subthreshold transistor can mimic neural activity, and recently, it has been shown that memristor can mimic synapses. Alternately, neural networks have been implemented in electronics to build intelligent systems for problem optimization and classification (e.g., retina for object recognition, regression and computation). Similarly, in some embodiments, the present invention provides for a new framework, termed 'cytomorphic electronics,' which aims to mimic the dynamic behavior of biological systems in living cells using electronic circuits. The goal of cytomorphic electronics is to study, predict and build synthetic and natural biological systems by providing a reliable and rapid simulation framework. In some embodiments, cytomorphic may be a multidisciplinary framework that translates principles of molecular networks to engineering, and vice versa, just as neuromorphic engineering has led to neuro-inspired engineered systems (adaptive artificial intelligent mixed-signals electronics circuits). As was shown above, the thermodynamic Boltzmann exponential equations describe the electron flow in the electronic subthreshold MOS transistor as well as molecular flux in chemical reactions. This similarity suggests that log-domain analog computations in electronics can be mapped to log-domain analog computations in biology, and vice versa. Thus, trans-linear circuits in subthreshold MOS transistors can be utilized to mimic the behavior of biochemical reactions and genetic circuits. However, it is challenging to capture the random fluctuations of biochemical reactions that involve a very small number of proteins, such as a DNA-protein binding reaction, primarily because the number of electrons that flow in subthreshold MOS transistors is much higher than the number of proteins that are involved in biochemical reactions in living cells. Therefore, stand-alone artificial noise generation circuits for low SNR had to be constructed. Such circuits often involve many analog and digital circuits and increase the design complexity of scaling cytomorphic integrated electronics. To overcome this challenge, it is suggested to combine translinear circuits with Nanoelectronics. Herein, it will be shown that memristor devices can mimic the deterministic as well the stochastic dynamics of bio-chemical reactions and genetic circuits. Recently, it has been shown that the rate of switching in memristor devices is determined by the bias-dependent activation energy (voltage/current controlled), following Boltzmann statistics $\Gamma = A \cdot \exp(-E_g(v)/K_B T)$, while an increase in voltage decreases the energy barrier. This simple analysis shows that the reaction time ($\tau_{reaction}$) of protein binding to DNA and the delay time of switching memristor ($\tau_{switch}$), follow a Poisson distribution. As a first-order analysis, in asymptotic boundary conditions, the memristor can mimic the binding process of biochemical reactions. For example, for low protein levels, the binding site is empty with minimum activity and for high protein levels, all the binding sites are occupied, with maximum activity. In a similar fashion, when no programming voltage is applied on the memristor, the $TiO_2$ layer is empty by ionic oxygen vacancies, with very low activity (the memristor conductance is very low), and when a high programming voltage is applied on the memristor, the $TiO_2$ layer is occupied by ionic oxygen, with maximum activity (the memristor conductance is very high). Thus, binding reactions and memristor devices exhibit a non-linear, input-output transfer function, with two logic states—"0/1". Moreover, the stochastic behavior of biochemical reactions and switching memristors is similar. These analogies suggest that one can efficiently mimic large-scale genetic-processing systems in biological networks on a hybrid memristor-analog-digital electronic chip.
Artificial Molecular Networks (AMNs) in Electronics AMNs attempt to apply principles of molecular networks in electronic circuit design, to yield novel biologically inspired robust, intelligent and energy-efficient systems. In some embodiments, the present invention integrates memristors and translinear circuits to design and fabricate ultra-low power electronic circuits exploiting the computational power of the perceptgene model (see equations 2 and 3 above). The basic AMN model consists of three parts:

Multiplication (binding reaction): Translinear circuit design exploits the exponential current-voltage non-linearity relationship in semiconductors to perform inherent/built-in complex mathematical operations such as multiplication and division. They enable powerful, ultra-low power analog circuit analysis and synthesis framework. Translinear circuits perform these complex computations without using differential voltage signals and could feasibly be integrated into device-level circuit design methodology. Translinear circuits can be implemented by bipolar junction transistors (BJT) in design of systems with high speed or by subthreshold CMOS transistors in design of ultra-low power systems. The output current ($I_{out}$) is given by:

$$I_{out} = \frac{I_{i_1} \cdot I_{i_2}}{I_{Ref}} \quad (4)$$

(ii) Power-law function (Cooperativity weight): The simplest way to interpolate the power law function into our analog translinear circuits is by adding a resistive divider to these circuits. When $R_1$ and $R_2$ are very large, very small currents will pass through the resistors compared to the currents that pass through the transistors. Thus, the output current ($I_{out}$) can be written as:

$$I_{out} = I_T \cdot \left(\frac{I_{in}}{I_{Ref}}\right)^n, \quad n = \frac{R_1 + R_2}{R_2} \quad (5)$$

The main advantage of using memristors to implement cooperativity weight (or Hill coefficient) lies in the control of the Hill coefficient values online, and in this case, intelligent and adaptive electronics can be trained by machine learning algorithms. Moreover, because the Hill coefficient is set by the ratio of the resistors, high resistance can be used, and in this case a small amount of power will be dissipated on the resistors.

Log-linear activation function: It is simple to show that Michaelis-Menten kinetics (Equation 2) can be modeled by Kirchhoff's voltage law (KVL) or kickoff current law (KCL) and by a voltage divider between resistances of value Y and $K_d$. In this circuit, the number of programming pulses (#P) controls the memristance and represents the concentration of transcription factors. The second memristor represents the dissociation constant $K_d$ (in this case, it will be initially programmed to have a constant value). The power supply voltage represents the maximum activity of the promoter ($P_{ON}$). The voltage that is dropped on the capacitor in steady state represents the bound promoter and is given by:

$$V_{Pr} = V_{Pon} \cdot \frac{R_y}{R_y + R_{Kd}}, \quad R_y = f(\#P) \quad (6)$$

The first Equation of 6 represents KVL and the second equation represents memristor flux-charge integration characteristics, while the function $f$ depends on memristor structure/physics features and program pulse waveform distribution. This circuit has several advantages: (i) the statistical distribution of a switching memristor device exhibits a Poisson distribution after each switching event, thus, it can capture the stochastic dynamics of biochemical reactions. (ii) It provides for a programmable dissociation constant for design of large-scale-AMNs. The other option of building a log-linear activation function is to use a differential subthreshold CMOS translinear circuit. The output current ($I_{Pr}$) represents the bound promoter and is given by:

$$I_{Pr} = I_{Pon} \cdot \frac{I_Y}{I_Y + I_{Kd}} \quad (7)$$

To capture the stochastic behavior of genetic circuits, the differential subthreshold CMOS translinear circuit may be combined with a memristor, using a current mirror circuit.
Adaptive Genetic and Electronic Networks for Intelligent-Parallel-Computation Machine learning is the science of getting artificial machines to act intelligently without being explicitly programmed. In the past decade, machine learning-based ANNs have been attracting vast attention as potential new architectural components and models for computing a wide variety of problems, such as pattern classification, object recognition, image processing, signal processing and optimization solving. One of the key elements of ANN is its ability to learn. A neural network is a complex adaptive system, meaning it can change its internal structure based on the information flowing through it. Typically, this is achieved through the weights adjustment, based on a first-order optimization algorithm that tends to converge to the global minimum of the gradient descent of the mean square error metric function.
A Learning and Adaptation Model in AMNs and SMNs (Supervised Learning)

Figure 5A:
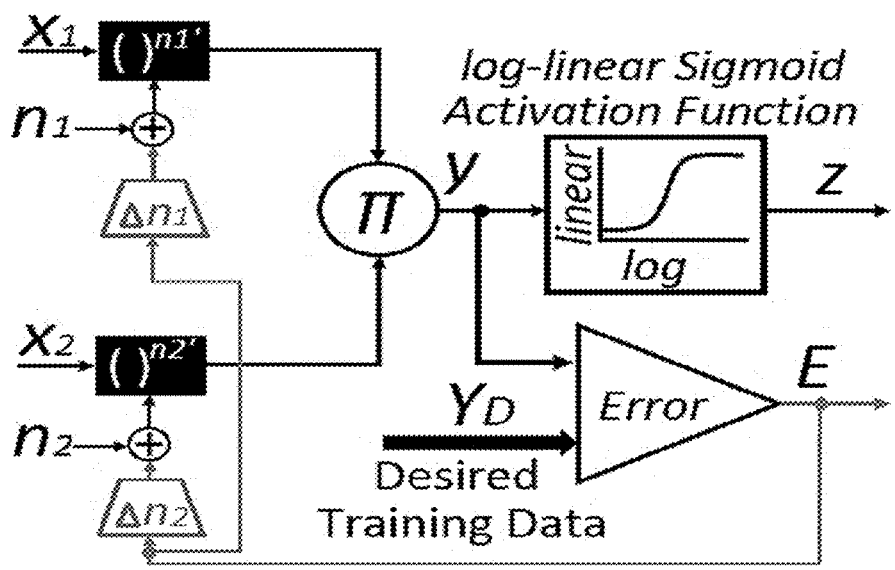
FIGS. 5A-E: (5A) the learning algorithm-based perceptgene model, (5B) & (5C) construction of an OR logic gate, based on the perceptron and perceptgene, (5D) simulation results of perceptron training, using the Adaline algorithm and perceptgene training using the Adalogline to learn OR logic functions (learning rate for both systems 0.04), and (5E) simulation results of perceptron (Adaline algorithm) and of the perceptgene (Adalogline algorithm) to learn an OR logic function when intrinsic noise is added to the output of the both system.

An innovative learning algorithm can be developed based on a perceptgene abstract model. Based on this, SMNs and AMNs can build adaptive biological systems with supervised evolutionary abilities, as well as artificial, intelligent ultra-low power, bioinspired translinear electronic circuits for a new era of robust big data computing. In some embodiments, the present learning algorithm is based on two features: (i) computation of the perceptgene depends on the cooperativity weights and therefore, by adjusting their values (Hill coefficient), a wide range of possible target output can be obtained for specific inputs, and (ii) the training rule minimizes the output error, using its gradient descent in a log-linear domain. The perceptgene-based learning algorithm is shown in FIG. 5A and is given by the following equations:

$$E_i = \frac{1}{2} \cdot [\ln(y_i) - \ln(Y_{Di})]^2 = \frac{1}{2} \cdot \left[\ln\left(\frac{y_i}{Y_{Di}}\right)^2\right] \quad (8)$$

Equation (8) calculates the error between the desired data ($Y_D$) and the actual perceptgene output (y), before the activation function i, using the least-mean square rule in a log-linear domain ($E_i=0$ when $y_i=Y_{Di}$). Then, the desired function will be achieved by adjusting the values of cooperativity weight based on:

$$n'_{ij} = n_{ij} - \ln\left[\left(\frac{y_i}{Y_{Di}}\right)^\lambda\right] \cdot \ln\left(\frac{x_j}{K_j}\right) \quad (9)$$

Figure 5B:
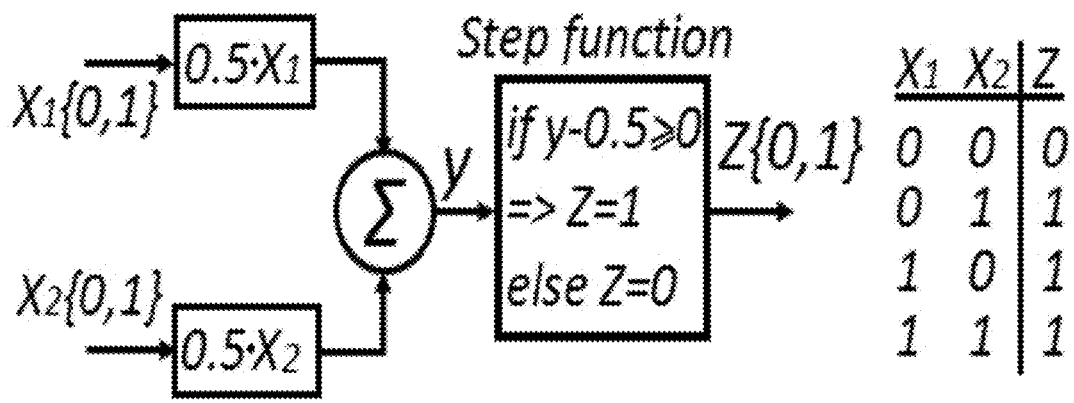
Figure 5C:
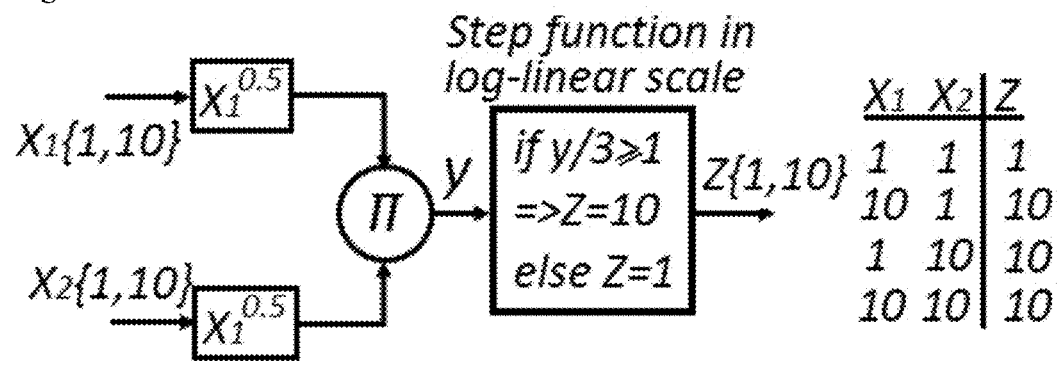
Figure 5D:
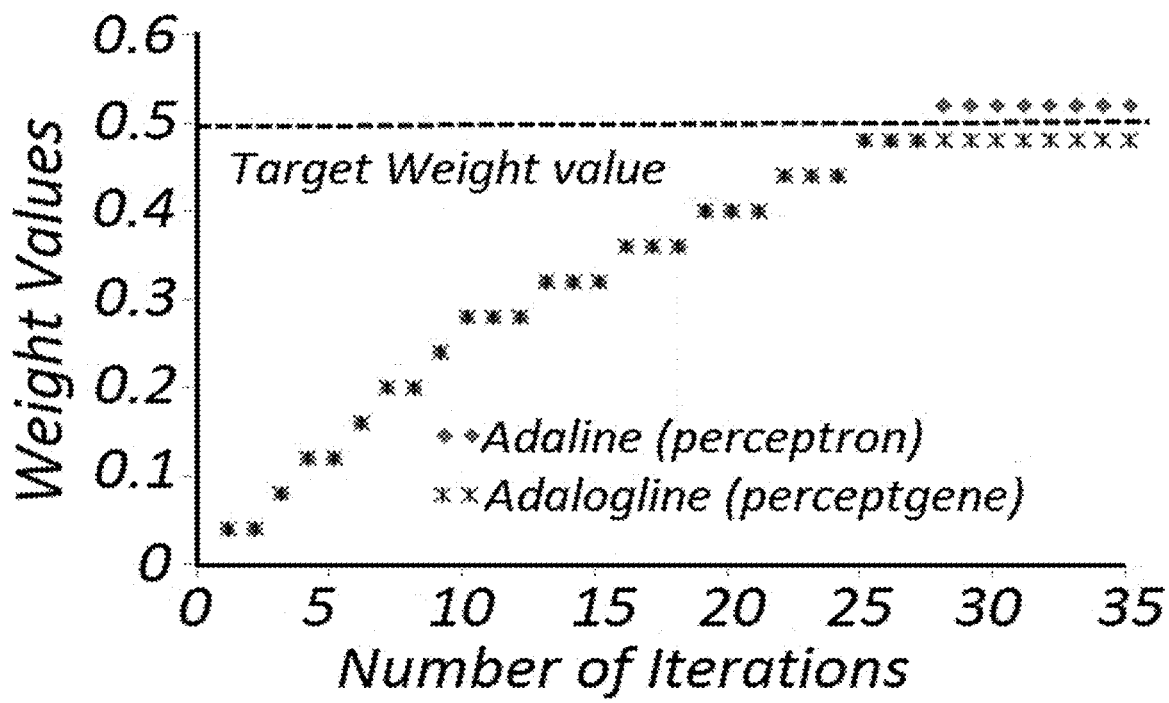
Figure 5E:
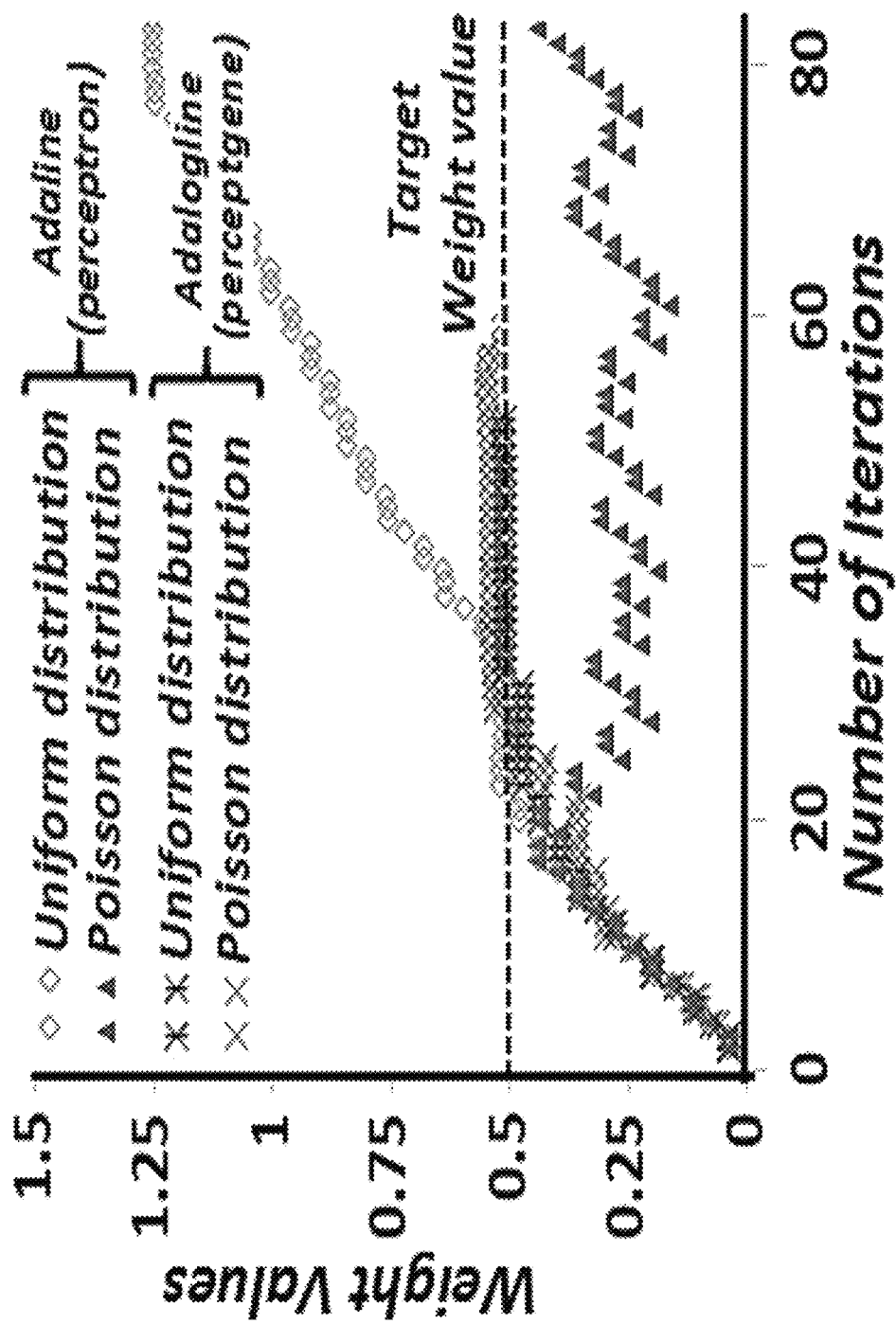
Figure 6A:
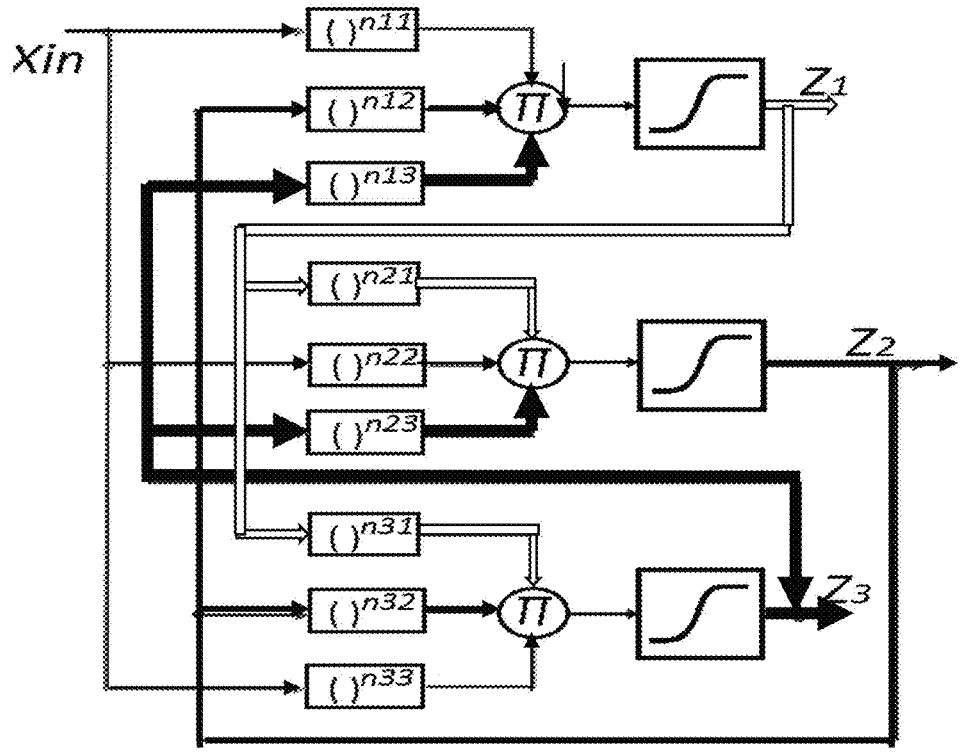
FIGS. 6A-D: (6A) the basic structure of a Hopfield molecular network (HMN) based on a perceptgene model, (6B) analog trans-linear subthreshold MOS circuit demonstrating an HMN, (6C) a log-linear analog-to-digital converter (ADC), and (6D) A schematic model of the energy landscape in the vicinity of the global minima for two analog input voltages.
Figure 6B:
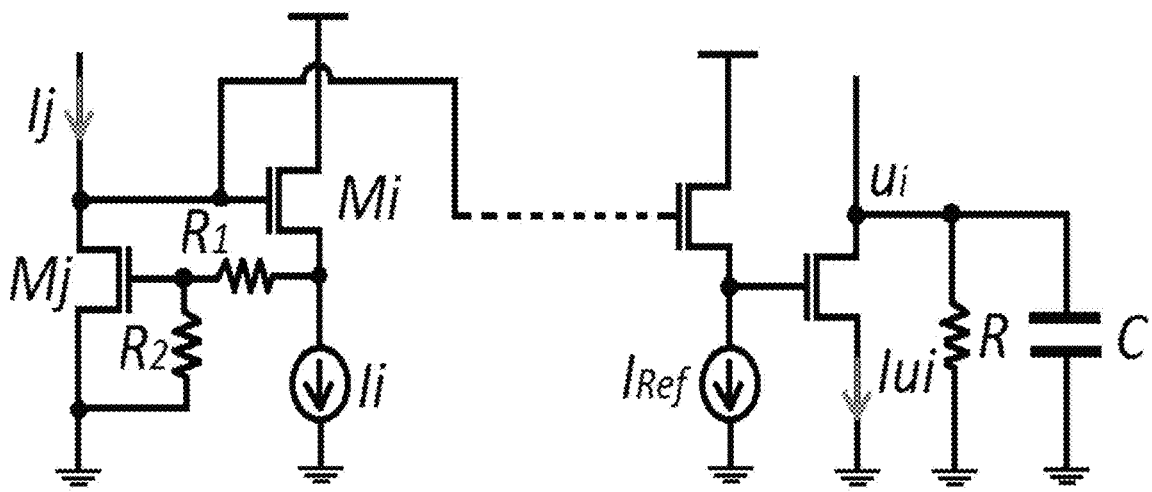
Figure 6C:
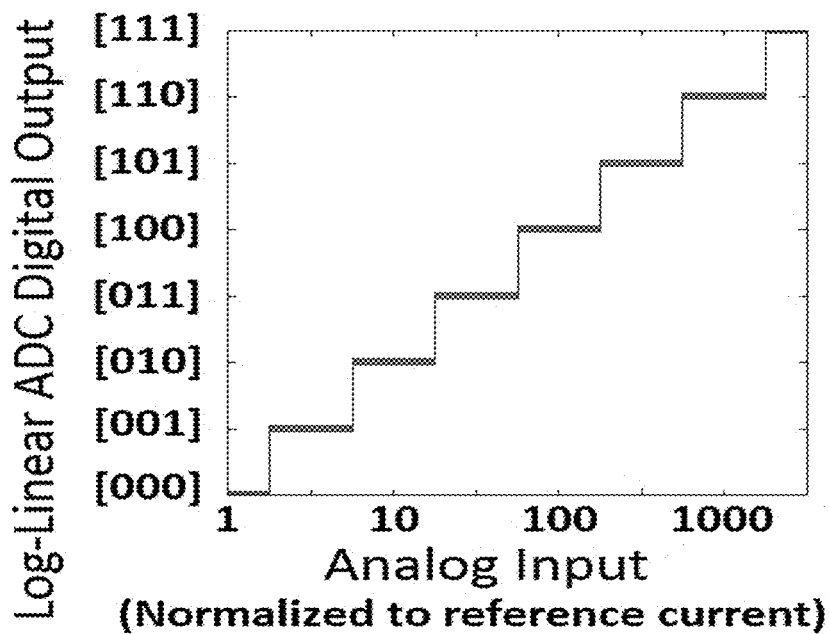

Equation (9) calculates the new value of cooperativity weights ($n'_{ij}$) based on the old value ($n_{ij}$) and gradient descent rule ($-\lambda \cdot dE_i/dy_{ij} = -\lambda \cdot [dE_i/dy_i] \cdot [dy_i/dn_{ij}]$). j is an index number of inputs, $\lambda$ is a learning$_{rate}$, and $K_j$ is a normalization parameter. The importance of equations (8) and (9) is the capacity to regulate the weight update by smaller steps, ensuring high resolution and guarantee of a global minimum in tradeoff with training time and number of samples. These equations can also be applied in multi-layer perceptgenes to describe more complex dynamics. This novel update rule may be called the adaptive logarithm linear gene (Adalogline) algorithm, analogous to the Adaptive linear neuron (Adaline) algorithm, used in adaptive signal processing and control. The Adalogline algorithm can be simply implemented in synthetic biology (binding reactions, binding cooperativity and gene regulation), translinear electronics circuits (multiplication, power law and KVL). Moreover, it has been shown that the log-transformed ratio of two input inducers can be achieved using analog synthetic biology. As a first step, the Adalogline was compared to the Adaline algorithm, which is widely used in machine learning, based on the perceptron model. FIGS. 5B and 6C show a 2-input OR-logic gate constructed with a perceptron and perceptgene, respectively. It was assumed that synaptic/cooperativity weights of the perceptron/perceptgene, and that it will be trained in a supervised manner to learn the logical OR function based on the information flowing through it and by desired labels. To achieve that, Adaline was ran on the perceptron and Adalogline on the perceptgene, with the same learning rate and dataset. The simulation results (FIG. 5D) show that both algorithms required the same number of iterations to reach the target weight values (with ~zero error). In the next step, an intrinsic noise was added to the output of the perceptron/perceptgene ($\bar{z}+\Delta z$), that was uniformly distributed between [0-1]/[1-10] or alternatively, was Poisson distributed ($\Delta z^2/\bar{z}=1$). FIG. 5E shows that the perceptron model-based Adaline algorithm becomes oscillating/divergent when noise is added. By contrast, the perceptgene model-based Adalogline algorithm was successfully trained when noise was added and acted as an OR logic function. The main reason for this behavior is that the perceptgene model is based on a logarithm function, which has a memory property, where the change depends on the history of the system ($dy/y=dx/x$), while the perceptron model is based on a linear relation without memory ($dy=dx$). This is a very important feature rendering the perceptgene model and Adalogline algorithm the best candidates to be applied in biological systems and in noise-tolerant analog electronics systems where noise is present. In some embodiments, the perceptgene model and Adalogline algorithm may be configured for building an adaptive log-linear classifier in living systems and electronics, based upon the following stapes:
  (i) Construct a single layer of SMN, based on the above, that can be trained. PF and NF loops will be used to control the values of the cooperativity weight. The training will be performed offline, in-situ, as a first step and then online by using a microfluidics, photodetector electronic circuit, and computer to adjust the values of cooperativity weight based on the Adalogline algorithm. In some embodiments, a single layer of SMN may be constructed to be trained in vivo using the Cas9 system and analog synthetic biology circuits. The Cas9 will bind and mutate PF and NF promoters. This will change the promoter binding efficiency, that will lead to changes in the values of the cooperativity weights; and
  (ii) fabricate AMNs, based on above, that can be trained online. By replacing the resistors with memristors, the values of cooperativity weights can be adjusted based on the Adalogline algorithm. Memristors have been successfully integrated with analog CMOS and trained online using gradient descent update rule for neuromorphic computing. The integration of memristors and translinear circuits based on subthreshold CMOS technology can be challenging, and as an alternative, BJT transistors may be used. As a first step, a Cadence simulation will be using 0.18 um TowerJazz technology. The power estimation of N-input perceptgene is 0.2 $\mu W \cdot N^2$, by contrast, the power estimation of N-input perceptron based on operational amplifier is 200 $\mu W \cdot N^2$ (we used 0.18 um TowerJazz technology).

SMNs and AMNs with Parallel Computational Abilities Using Hopfield Networks

Recurrent ANNs have been proposed as a model to construct asynchronous parallel computing networks (Hopfield networks). In this model, each perceptron behaves as an elementary unit that is fully cross-connected by symmetric weight feedbacks, allowing bidirectional data traversal to the rest of the ensemble. Hopfield networks have been proposed to solve several complex tasks that require massively parallel and compact computing processors with few parts such as: analog-to-digital conversion, NP-complete problems (Traveling-Salesman Problem) and content addressable memories (associative). A perceptgene model can be used to build parallelly-interconnected ultra-low power electronics, as well as to scale the computational complex dynamics of synthetic biological systems based on the Hopfield paradigm. Hopfield networks are energy-based that recursively converge to optimum in steady state. In some embodiments, the perceptgene model has energy features similar to those of a perceptron within a Hopfield network, termed a Hopfield Molecular Network (HMN). FIG. 6A shows a basic structure of HMN with three nodes. The three nodes are fully connected with $n_{ij}$ weights. In early works on Hopfield networks, it was shown that without auto-feedback and symmetric weight interconnections ($n_{ij}=n_{ji}$), the equations of the network dynamic motion could describe convergence to stable states, in which the output of all neurons (in our case, the output of the genes) remain constant without oscillations. As a first step, an energy function based on the perceptgene model must be introduced to harness the theoretical complexities posed by such an approach, equivalent to ANNs (perceptron). Analogous to the Hopfield analytic model, the power consumption formula of an elementary circuit (FIG. 6B) of an AMN may be extracted to formalize the Hopfield energy function of perceptgene is $$E_i = -\frac{K_B T}{q} \cdot \left[\sum_{i=1} I_i \cdot \ln\left(\prod_{j=1}\left(\frac{I_j}{I_{ref}}\right)^{n_{ij}}\right) - \sum_{i=1} I_i \cdot \ln\left(\frac{I_i}{I_{ref}}\right)\right] \quad (10.1)$$

-continued $$\Delta E_i = -\frac{K_B T}{q} \cdot \Delta I_i \cdot \left[ \ln\left(\prod_{j=1} \left(\frac{I_j}{I_{ref}}\right)^{n_{ij}}\right) - \ln\left(\frac{I_i}{I_{ref}}\right) - 1 \right] \quad (10.2)$$

where q is an electron charge, $I_i$ is a current that flows through Mi transistor and represents the input signal of perceptgene unit i, $I_j$ is a current that flows through the Mj transistor and represents the feedback signal of other perceptgene j units, $i_{Ref}$ is normalization current, and $n_{ij}$ is the Hill coefficient between perceptgene i and perceptgene j (equation 5). Equation (10.1) exactly fits the energy function that was developed in Hopfield networks in a log-linear domain (Translinear circuits). Equation (10.2) describes the change in the energy due to change in the input. Thus, the model for altering L causes E to be a monotonically decreasing function. States recursive change will continue until an optimal E is reached. This can be viewed by evaluating the motion equations of the circuit in FIG. 6B:

$$C \cdot \frac{du_i}{dt} + \frac{u_i}{R} = \frac{K_B T}{q} \cdot \left[ \ln\left(\prod_{j=1} \left(\frac{I_j}{I_{ref}}\right)^{n_{ij}}\right) - \ln\left(\frac{I_{ext}}{I_{Ref}}\right) \right] \quad (11)$$

Figure 6D:
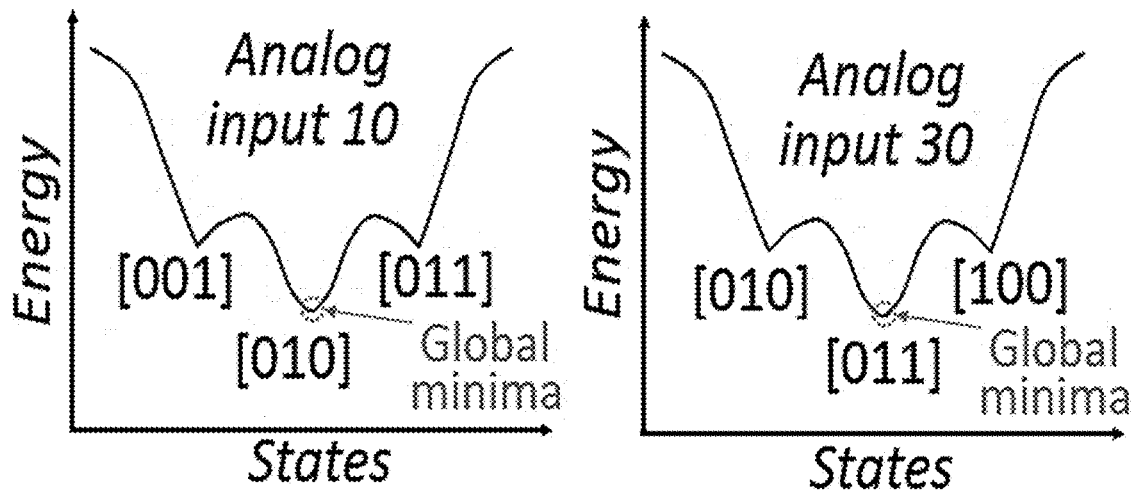

The circuit will reach stable steady state when equation (11) equal zero, and by fitting the external current ($i_{ext}$), we will get $\Delta E_i$=0. The energy function of the Hopfield neural/molecular network, which is considered to be a Lyapunov function, describes the macroscopic dynamics of the network. It characterizes the energy minimization process and convergence of the network from an initial state to a minimum energy steady state. By defining an optimization equation for a specific application and reordering it in an energy-like style, the corresponding weights that fit the network specifications and application demands can be extracted. The main advantage of the new network (HMN) compared to the Hopfield neural network (based on perceptron), lies in the inherent implementation of the Boltzmann machine system using the stochastic dynamics of subthreshold transistors, memristor and genetic circuits. Due to the nature of the energy function, the solution of the Hopfield network is highly dependent on its initial state. Unfortunately, the energy function may decrease and then settle to one of the equilibrium points called a "local minima" that does not correspond to the correct state. However, stochastic recurrent networks (when noise is added to Hopfield networks similar to our systems) could avoid this situation because stochastic dynamics can provide energy to the system resonating it to the global minimum. Thus there can be built:

(i) A log-linear 4/8-bits analog-to-digital converter (ADC) using AMNs (electronic) based on HMN design (FIG. 6C). Biological and physiological signals often have a log-linear input-output transfer function. Therefore, ADC that can directly convert the measured analog signal in a logarithm domain to a digital signal will improve the performance of biomedical devices. It has shown that the Hopfield energy function satisfies the ADC problem in a linear-linear domain with connection weights $2^{i+j}$, however, it failed to solve the ADC problem in a log-linear domain. By contrast, our new Hopfield energy function (Equation 10) inherently satisfies the ADC problem in a log-linear domain with connection weights i+j. In our ADC design, all the inputs of the HMN are connected to the same analog input. The second advantage of the proposed HMN is that the ratio of the maximum and minimum coefficients is small compared to the original Hopfield network. The Hopfield neural and molecular network for ADC, recursively solved evolving from initial state and converge to digital steady state (FIG. 6D compares the energy function between two different analog inputs). There can be built an ultra-low power analog supercomputer, with parallel computational and adaptive abilities, to solve complex stochastic cognitive tasks in real time with high precision. Alternatively, asymmetric Hopfield networks may be applied based only on feed-forward topologies; and (ii) content addressable memory (CAM) using SMNs (in living cells) based on HMN design. The construction of biological systems in living cells with memory abilities has recently gained widespread attention for its potential in new biotechnology and biomedical applications as well as to study systems biology. So far, living cells with two states have been successfully constructed using positive feedback loops (e.g., the toggle switch). To go beyond this, the fact that the Hopfield energy function guarantees convergence to local minima may be used, and therefore, the HMN network can serve as a system that can store pattern with an associative memory element, co-localizing memory and computation. The new HMN design may be used to construct biological systems in living cells with memory abilities of three rather than two states, and investigate computation within memory, utilizing associative processing capacities.

Figure 7A:
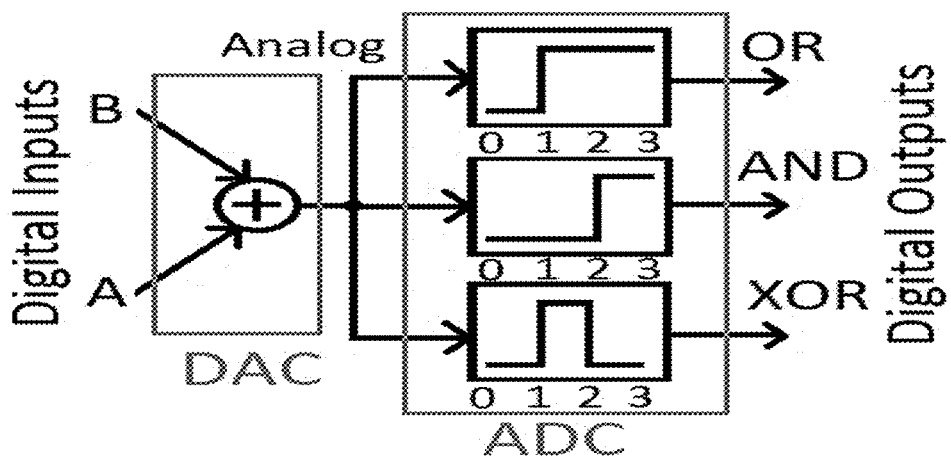
Figure 7E:
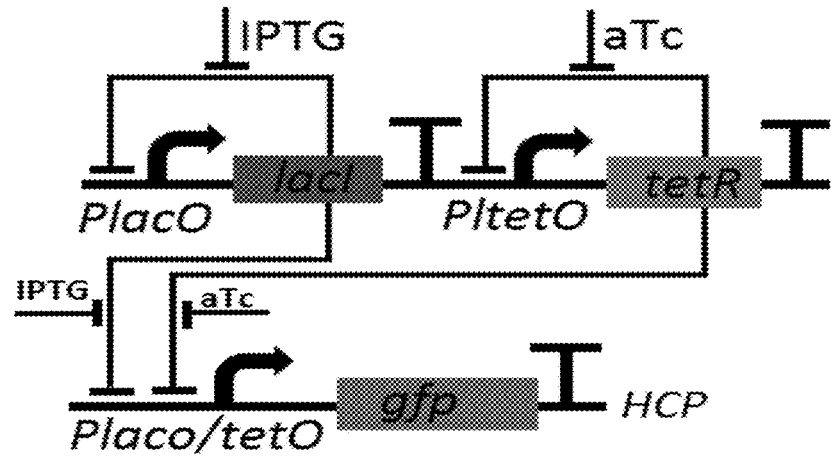
Figure 7F:
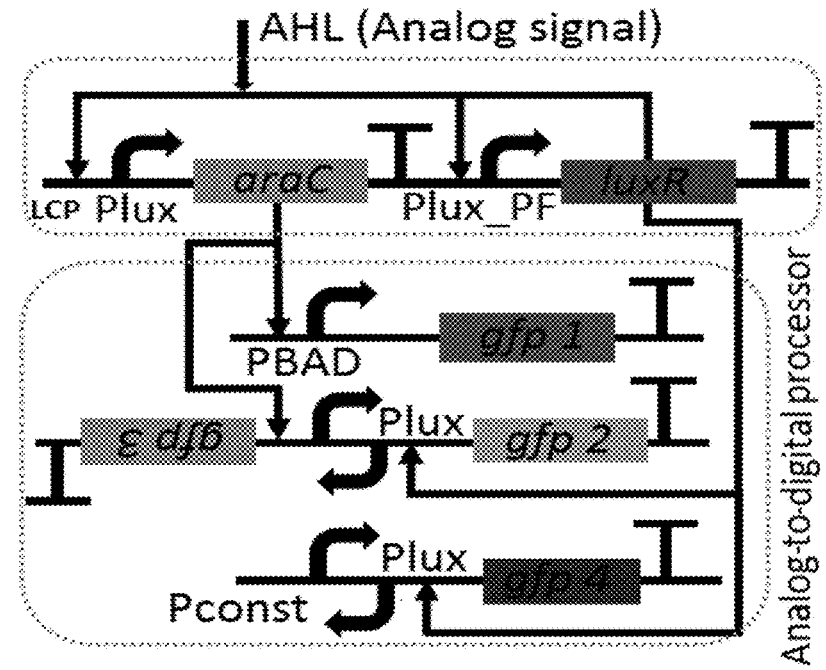
Figure 7G:
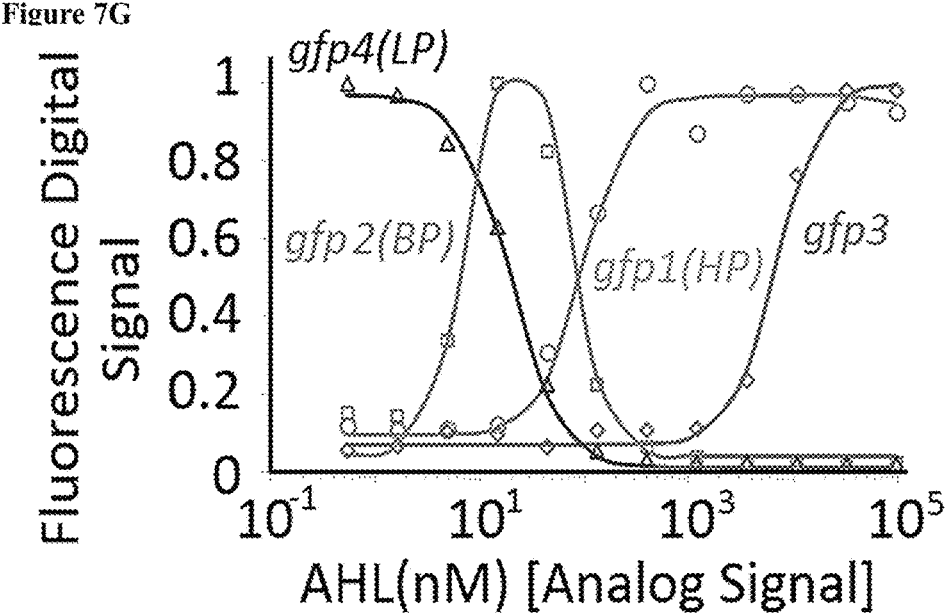
Figure 7H:
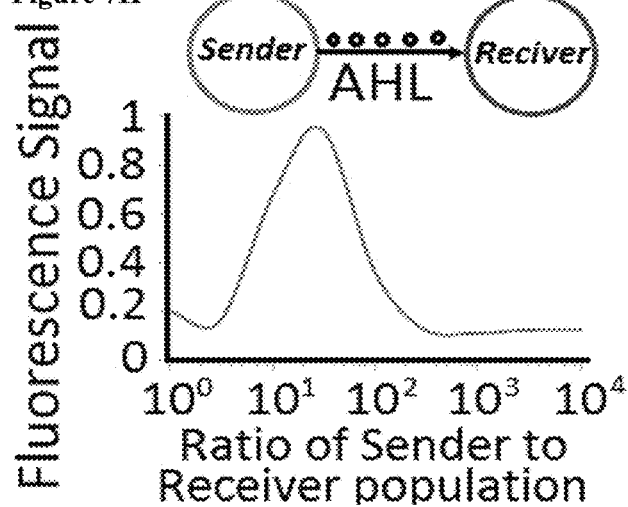

Scaling Gene Networks in Living Cells Based on a Log-Linear Threshold Unit Model:

The early works of ANNs were based on a linear threshold unit (LTU) and were specifically targeted to serve as a computational model of the "nerve net" in the brain. The LTU model consists of two parts; (i) digital-to-analog converter (DAC) which sums all the inputs and (ii) an ADC that converts the analog signals to digital outputs by designing the different shapes of the activation function. It has been shown that the LTU model can implement any Boolean logic function. For example, AND/OR logic gates can be implemented by a simple perceptron, by varying the threshold values (FIG. 7A). An XOR logic function can be implemented by constructing a band pass (FIG. 7B) through cascading two perceptron layers. In some embodiments, a perceptgene model and SMNs may be used to build a log-linear threshold unit ($L^2TU$) for scaling gene networks in living cells with a minimal number of synthetic parts. The inputs and outputs are binary discrete numbers, the weights are unchanged, with no engineering role and a more flexible threshold value. The $L^2TU$ is an alternative biodesign model to the conventional Boolean algebra model and is based on analog and digital design rules. In analogous to LTU, the $L^2TU$ consists of two parts: (i) linear-log DAC, which multiplies the digital inputs together and (ii) a log-linear ADC that converts the analog signals to digital outputs by designing its activation function. In some embodiments, two examples for constructing complex logic functions based on the $L^2TU$ model may be configured:

(i) Scaling a full-bit adder: First, there will be constructed a 1-bit full adder that has three inputs: A, B and Carry in ($C_{in}$), and two outputs: Sum and Carry out ($C_{out}$). The truth table of a 1-bit full adder is shown in FIG. 7B. The analog signal is the multiplication of the digital inputs (A·B·$C_{in}$) that have features of analog signals such as current or molecular concentration. By presenting the digital output signals (Sum & $C_{out}$) as a function of the analog signal (A·B·$C_{in}$), one can observe the activation function of every output (FIG. 7C). For example, the Cout output can be viewed as a high pass filter with a threshold of 100 a.u., and the Sum output is a combination of the band pass (10-100 a.u.) and high pass filters with a threshold of 1000 a.u. The full construction of a 1-bit full adder is presented in FIG. 7D. Hybrid promoters and proteins binding reactions will be used to implement a log-linear DAC. FIG. 7E shows an example of construction of a 2-inputs-log-linear DAC using the lacI/tetR hybrid promoter in living cells. The log-linear DAC acts as an analog multiplier when the inputs accept digital values. The design and construction of the log-linear ADC is more challenging than of the DAC. In some embodiments, the analog circuit design discussed above may be utilized and combined with the digital circuit design discussed above, to engineer the shape of the activation function achieving a log-linear ADC processor. The new circuit will rely on a hybrid analog-digital design and mixed signal. FIG. 7F shows a two-component genetic circuit for construction of a low/high/band pass filter with programmable threshold values: (I) a wide dynamic range circuit based on graded PF that accepts AHL as an analog input and controls the expression level of LuxR and AraC in analog fashion, (II) an ADC processor. A band pass was achieved using competition between $P_{BAD}$ and $P_{lux}$, both of which are controlled with the AHL input (FIG. 7G). The same circuit can behave as a high pass filter, with a very high threshold value when the gfp signal that is controlled by $P_{lux}$ is read rather than $P_{BAD}$. For high AHL concentrations, the $P_{lux}$ promoter wins the competition and leads to a signal in the 3-5' direction (FIG. 7G). A low pass filter has been achieved by competition between a constitutive promoter and the $P_{lux}$ promoter (FIG. 7G). Note that cloning the promoters in different copy numbers can increase/decrease the threshold values (data not shown). Furthermore, adding decoy binding sites of $P_{BAD}$ and $P_{lux}$ will affect the transfer function. Quorum sensing cell-to-cell communication may be used to wire the DAC and ADC. This mechanism has been widely used in synthetic biology. For example, a bacterial sender strain was constructed that constitutively produces AHL molecules and we combined them with a bacterial receiver strain that includes a band pass filter based on $P_{lux}$ promoter in the same solution medium (FIG. 7H). Equivalently, the DAC will produce AHL molecules by replacing the gfp gene with luxI gene and the ADC will accept the AHL molecules.

(ii) 4-input XOR gate: this may be achieved by combining a 4-bits log-linear DAC and a log-linear ADC processor that consists of two shifted band pass circuits. The main advantage of the L²TU biodesign framework compared to other frameworks, is that fewer devices are needed to carry out a given computation with minimal requirements of host cell resources (1-bit full adder will require only 5 synthetic parts, and a 4-input XOR will require 6 synthetic parts), and at the same time, the output results are as reliable as in the digital biodesign framework. In some embodiments, a biocomputer may thus be built, which includes the basic Arithmetic-logic operations (e.g., 4-bit full Adder, 4-bit Subtractor, and logic gates) and memory, that operates across living cells with a minimal number of synthetic parts and minimal requirements of host cell resources, to solve complex tasks in real time with high precision. The proposed biocomputer can operate as an embedded system or can be integrated with bioelectronics to perform biomarker analysis for diagnostic and therapeutic applications (e.g, detect and respond to changes in the state of health). In some embodiments, the intelligent genetic systems discussed above may be combined with stress promoters, e.g., to detect toxins in water.

The Architecture of Biological Systems to Scale-Up SMNs and AMNs

Figure 8A:
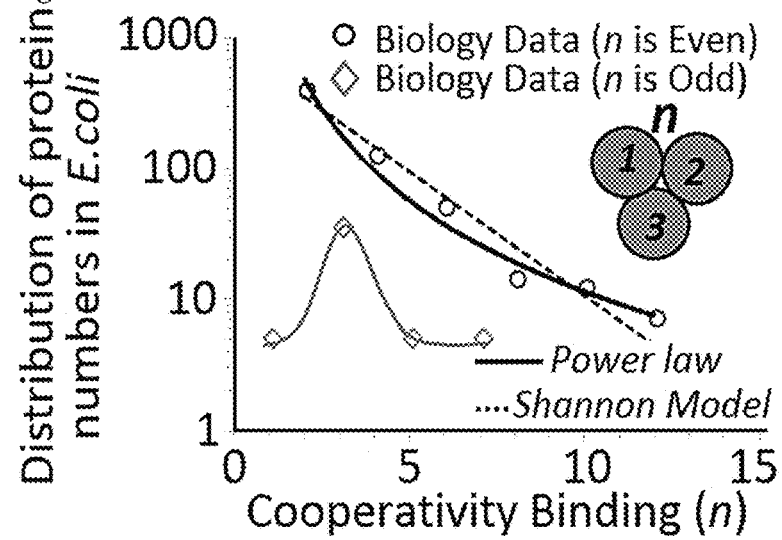
FIGS. 8A-B: (8A) distribution number of protein subunits in E. coli, and (8B) Shannon model for a perceptgene in the presence of intrinsic noise within the biochemical reaction.
Figure 8B:
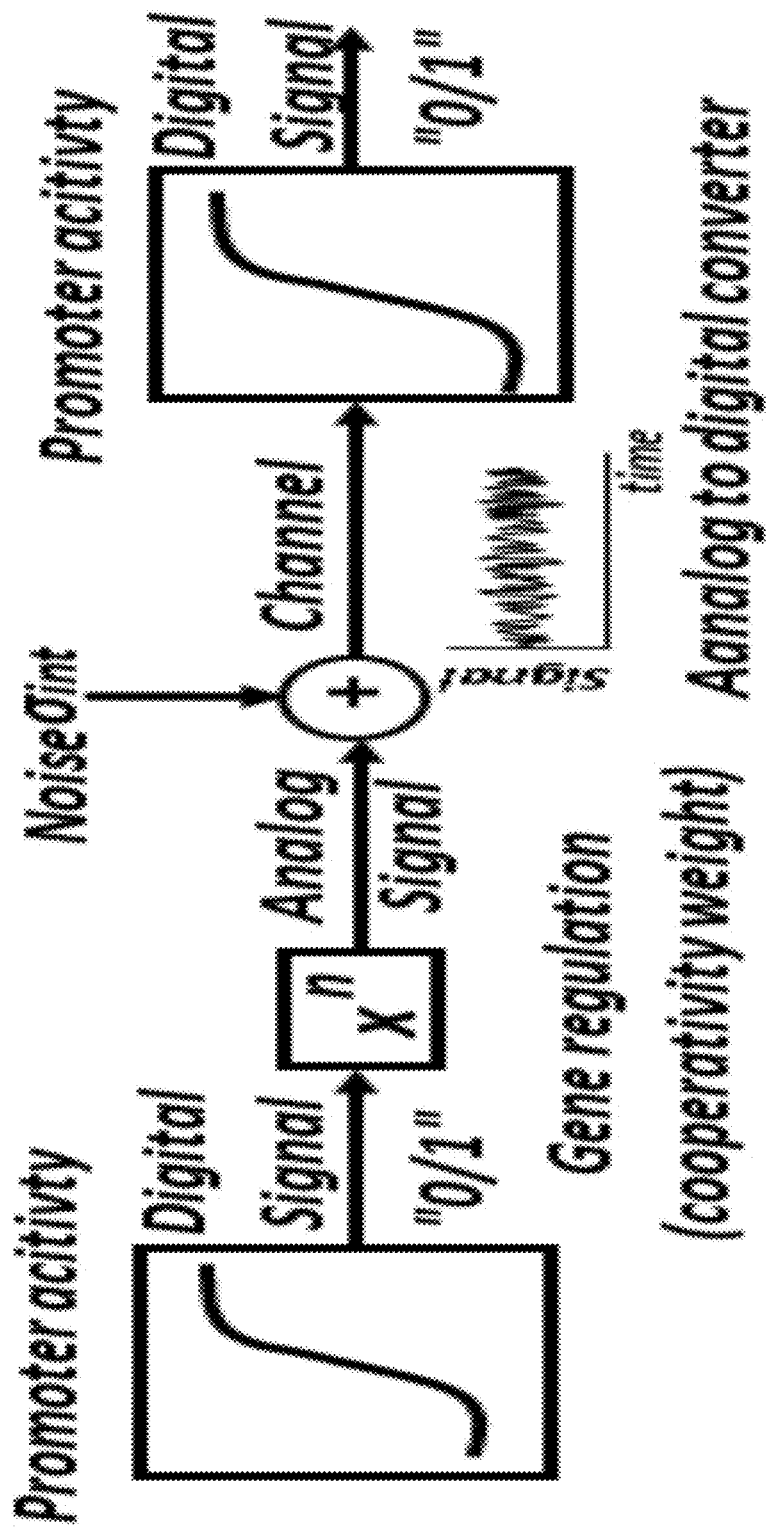

FIG. 8A illustrates the number of protein subunits (n) in *E. coli*. FIG. 8A shows that the distribution of odd number protein subunits (n=1, 3, 5 . . . ) follows Poisson statistics, which indicates that most nodes have approximately the same number of links. Such networks are known as a random network. By contrast, the distribution of even number protein subunits (n=2, 4, 6, . . . ) is characterized by a power-law degree distribution, termed Scale-free networks. It has been shown that many biological networks are characterized as a scale-free networks. In such networks, the probability that a node is highly connected is statistically more significant than in a random network. This provides robustness to the network. Moreover, in some embodiments, the present invention provides for an informative model that fits power-law distribution based on an analog-digital processing unit using the Shannon theorem (FIG. 8A). In this model, the quantitative Fig. of Merit (evaluates performance, speed and energy) of a perceptgene is approximated in the presence of intrinsic noise. It is assumed that the intrinsic noise follows Poisson statistics (FIG. 8B). Both models indicate that cells optimize considering an overwhelming tradeoff between power, speed and precision. In some embodiments, this model may be further tested for other organisms and used to scale-up the design of synthetic biological and electronic systems.

In some embodiments, the present invention merges many new and innovative ideas from neuroscience, systems biology and electrical engineering, to offer a novel framework for collective computational intelligent abilities, as detailed in table 1 below. This framework naturally presents in synthetic biological and translinear electronic systems. The present approach is supported by several preliminary experimental and theoretical results, and most importantly, it underlies the analog synthetic biology and cytomorphic works. In some embodiments, *Escherichia coli* and yeast may be used as host cells for the circuits. Electronic circuits may be fabricated by TowerJazz Semiconductor.

TABLE 1

| perceptron vs perceptgene properties and features | | |
|---|---|---|
| Features | Perceptron | Perceptgene |
| Bio-inspired | Brain | Cell Biology |
| Activation | Neuron | Gene Regulation |
| Connection Weighting | Synapse (wij) | Cooperativity Binding (nij) |

TABLE 1-continued perceptron vs perceptgene properties and features

| Features | Perceptron | Perceptgene |
|---|---|---|
| Operation Domain | Linear | Log-Linear |
| Activation Function | Sigmoid | Hill-Function |
| Collective Process | Addition | Multiplication |
| Gradient Descent learning rule | $\Delta w_{ij} = \eta \sum_j (y_{ij} - d_{ij}) \cdot x_{ij}$ | $\Delta n_{ij} = \sum_j \ln\left(\left(\frac{y_{ij}}{d_{ij}}\right)^\eta\right) \cdot \ln(x_{ij})$ |
| Noise tolrtance | Training is Sensitive | Training is Robust |
| Change in Energy | $\Delta E_i = -\Delta y_i \cdot \sum_{j \neq i} w_{ij} \cdot y_j$ | $\Delta E_i = -K_B T \cdot \Delta y_i \cdot \ln\left(\prod_{j \neq i} \left(\frac{y_j}{y_0}\right)^{n_{ij}}\right)$ |
| Content-Addressable Memory | Hopfield | Boltzmann |
| Network Topology | Feedforward/Recurrent | Feedforward/Recurrent |
| Causality | None | Weber's law |
| Implementation | CMOS Mixed Signal | Translinear circuits |
| Activation Function | Differential Amplifier | KVL/KCL |
| Connection Weighting | Memristor | Memristor |
| Speed | High | High |
| Power | High | Low |
| Design | Simple | Complex |

Experimental Results

Figure 9A:
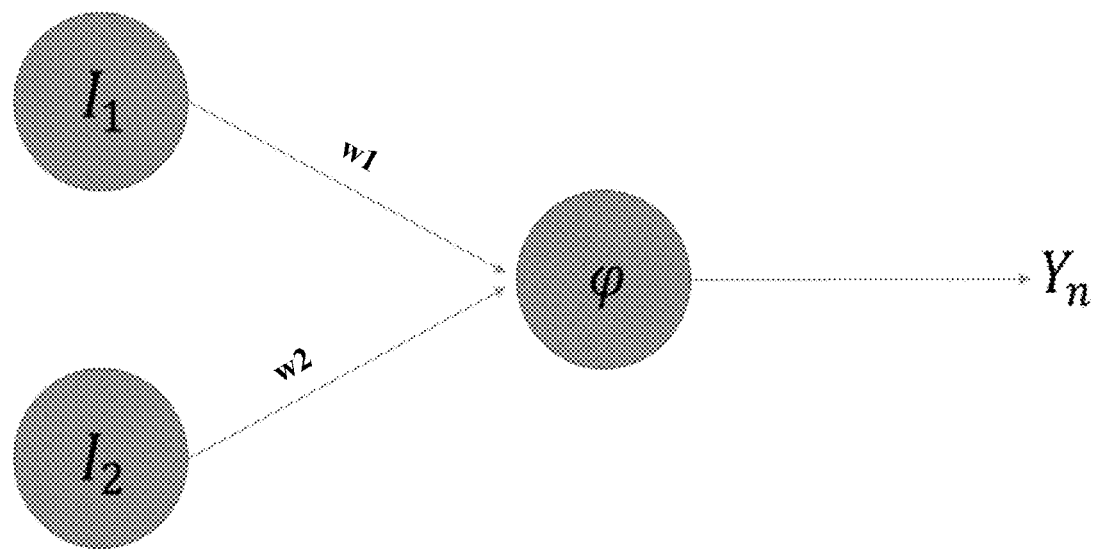
FIGS. 9A-9G illustrate experimental results.

As noted above, the present invention provides for a perceptgene-based neural network. FIG. 9A illustrates a single neural cell, where $I_1$, $I_2$ are the inputs, $w_1$, $w_2$ are input weights, $\varphi$ is the activation function, and n is the iteration number. The perceptron algorithm functions as follows:

$$v_n = w_{1,n} I_1 + w_{2,n} I_2$$

$$y_n = \begin{cases} 0, & v_n - Y_{th} < 0 \\ 1, & v_n - Y_{th} \geq 0 \end{cases}$$

$$E_{rr} = \frac{1}{2}(Y_{exp} - y_n)^2$$

$$W_{i,n+1} = W_{i,n} - \eta(y_n - Y_{exp})I_i$$

whereas the perceptgene algorithm functions based on the following:

$$v_n = I_1^{w_{1,n}} I_2^{w_{2,n}}$$

$$y_n = \begin{cases} 1, & \frac{v_n}{Y_{th}} < 3 \\ 10, & \frac{v_n}{Y_{th}} \geq 3 \end{cases}$$

$$E_{rr} = \frac{1}{2}\left(\log\left(\frac{y_n}{Y_{exp}}\right)\right)^2$$

$$W_{i,n+1} = W_{i,n} - \eta \log\left(\frac{y_n}{Y_{exp}}\right) \log\left(\frac{I_i}{2}\right)$$

Figure 9B:
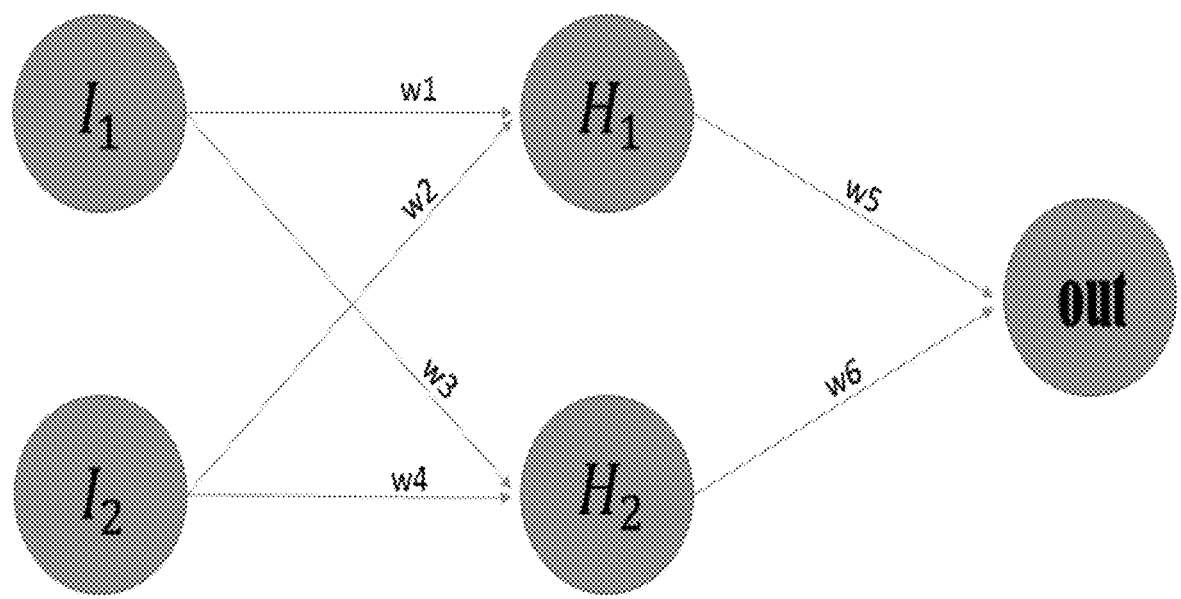

With reference to FIG. 9B, in some embodiments the present invention provides for a three-layer neural network comprising an input layer having N inputs, an intermediate layer having M neural cells, and an output layer having a single neural cell. In FIG. 9B, $I_1, I_2, \ldots I_N$ represent inputs, $H_1, H_2, \ldots H_M$ represent interim layers neural cells, and out is the output layer neural cell. $V_x$ will represent the input of neural cell X, and $O_x$ the output of neural cell X.

In this configuration, a perceptron-based network may use the logistic activation function $$\varphi(v) = \frac{1}{1 + \exp(-v)}$$

The forward pass algorithm of this network will then be, generally:

$$v_{H_m} = \sum_{k=1}^{N} w_{N*(m-1)+k} * I_k$$

$$O_{H_m} = \varphi(v_{H_m})$$

$$v_{out} = \sum_{k=1}^{M} O_{H_k} * w_{N*M+k}$$

$$O_{out} = \varphi(v_{out})$$

And in the case of the network illustrated in FIG. 9B:

$$v_{H_1} = w_1 * I_1 + w_2 * I_2,$$

$$v_{H_2} = w_3 * I_1 + w_4 * I_2$$

$$O_{H_1} = \varphi(v_{H_1}) = \frac{1}{1 + \exp(-v_{H_1})}$$

$$O_{H_2} = \varphi(v_{H_2}) = \frac{1}{1 + \exp(-v_{H_2})},$$

$$v_{out} = w_5 * O_{H_1} + w_6 * O_{H_2}$$

$$O_{out} = \varphi(v_{out}) = \frac{1}{1 + \exp(-v_{out})}$$

The backpropagation algorithm of this network will be, for training rate n, where $$E_{rr} = \frac{1}{2}(Y_{exp} - O_{out})^2,$$

$$\frac{\partial E_{rr}}{\partial w_5} = \frac{\partial E_{rr}}{\partial O_{out}} \frac{\partial O_{out}}{\partial v_{out}} \frac{\partial v_{out}}{\partial w_5}$$

$$\frac{\partial E_{rr}}{\partial O_{out}} = -(Y_{exp} - O_{out})$$

$$\frac{\partial O_{out}}{\partial v_{out}} = O_{out}(1 - O_{out})$$

$$\frac{\partial v_{out}}{\partial w_5} = O_{H_1}$$

$$\frac{\partial E_{rr}}{\partial w_1} = \frac{\partial E_{rr}}{\partial O_{out}} \frac{\partial O_{out}}{\partial v_{out}} \frac{\partial v_{out}}{\partial O_{H_1}} \frac{\partial O_{H_1}}{\partial v_{H_1}} \frac{\partial v_{H_1}}{\partial w_1}$$

$$\frac{\partial v_{out}}{\partial O_{H_1}} = w_5$$

$$\frac{\partial O_{H_1}}{\partial v_{H_1}} = O_{H_1}(1 - O_{H_1})$$

$$\frac{\partial v_{H_1}}{\partial w_1} = I_1$$

After finding the partial derivatives of the weighted error, the weightings vector will be updated as follows:

$$w_{i,n+1} = w_{i,n} - \eta \frac{\partial E_{rr}}{\partial w_{i,n}}$$

For the perceptgene-based network, the forward pass algorithm is, generally:

$$v_{H_m} = \prod_{k=1}^{N} I_k^{w_{N*(m-1)+k}}$$

$$O_{H_m} = \varphi(v_{H_m})$$

$$v_{out} = \prod_{k=1}^{M} O_{H_k}^{w_{N*M+k}}$$

$$O_{out} = \varphi(v_{out})$$

Figure 9C:
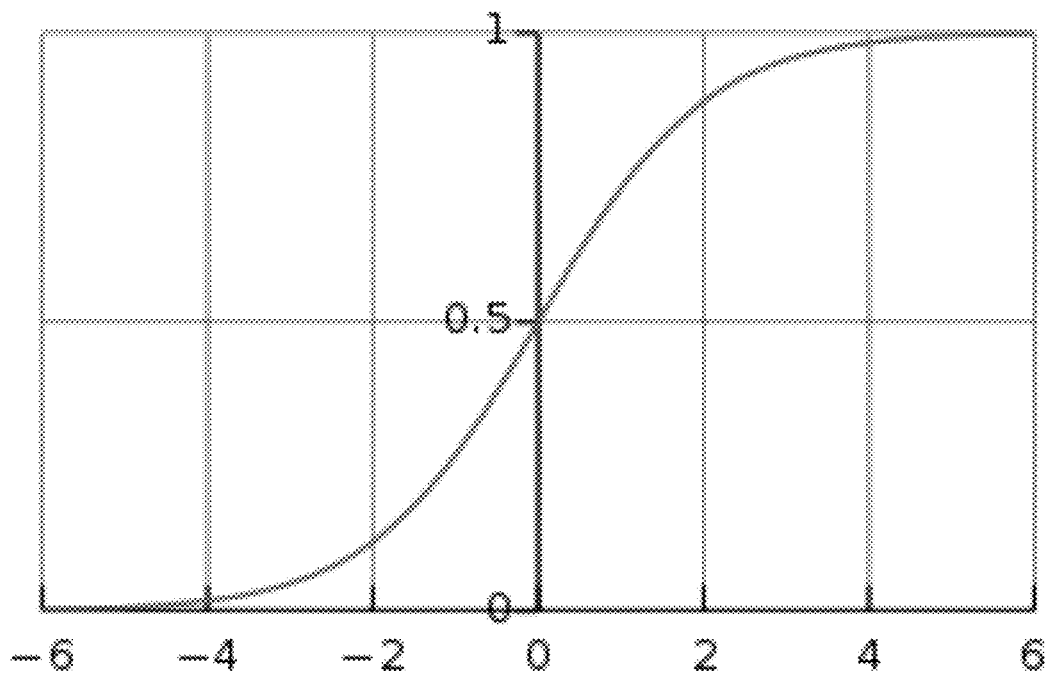

The same activation function as for the perceptron-based network may be used:

$$\varphi(v) = \frac{1}{1 + \exp(-v)}$$

whereby the function is illustrated in FIG. 9C. Both networks were run over a training set comprising 342 samples, with a verification set of 114 samples. However, the classification by perceptgene would need to be tagged by [1,10] rather than [0,1], to enable performing a logarithmic function. Accordingly, the activation function for perceptgene may be modified as follows:

$$\varphi(v) = 10^{\frac{1}{1+\exp(-\log 10(v))}}$$

The back propagation algorithm for the perceptgene network, for training rate n, will be:

$$E_{rr} = \frac{1}{2}\left(\log\left(\frac{O_{out}}{Y_{exp}}\right)\right)^2$$

$$\frac{\partial E_{rr}}{\partial w_5} = \frac{\partial E_{rr}}{\partial O_{out}} \frac{\partial O_{out}}{\partial v_{out}} \frac{\partial v_{out}}{\partial w_5}$$

$$\frac{\partial E_{rr}}{\partial O_{out}} = 2*0.5*\log\left(\frac{O_{out}}{Y_{exp}}\right)*\frac{1}{\frac{O_{out}}{Y_{exp}}}*\frac{1}{Y_{exp}} = \log\left(\frac{O_{out}}{Y_{exp}}\right)\frac{1}{O_{out}}$$

$$\frac{\partial O_{out}}{\partial v_{out}} = \frac{\partial \varphi(v_{out})}{v_{out}}$$

$$= \frac{1}{v_{out}}*\varphi(v_{out})*\log_{10}(\varphi(v_{out}))*$$
$$(1 - \log_{10}(\varphi(v_{out})))$$

$$= \frac{1}{v_{out}}*O_{out}*\log_{10}(O_{out})*(1 - \log_{10}(O_{out}))$$

$$\frac{\partial v_{out}}{\partial w_5} = O_{H_2}^{w_6}*O_{H_1}^{w_5}*\log_{10}(O_{H_1}) = v_{out}*\log_{10}(O_{H_1})$$

$$--> \frac{\partial E_{rr}}{\partial w_5} =$$

$$\log\left(\frac{O_{out}}{Y_{exp}}\right)\frac{1}{O_{out}}\frac{1}{v_{out}}*O_{out}*\log_{10}(O_{out})*(1-\log_{10}(O_{out}))v_{out}$$

$$\log_{10}(O_{H_1}) = \log\left(\frac{O_{out}}{Y_{exp}}\right)\log_{10}(O_{out})(1-\log_{10}(O_{out}))\log_{10}(O_{H_1})$$

$$\frac{\partial E_{rr}}{\partial w_1} = \frac{\partial E_{rr}}{\partial O_{out}} \frac{\partial O_{out}}{\partial v_{out}} \frac{\partial v_{out}}{\partial O_{H_1}} \frac{\partial O_{H_1}}{\partial v_{H_1}} \frac{\partial v_{H_1}}{\partial w_1}$$

$$\frac{\partial v_{out}}{\partial O_{H_1}} = w_5 O_{H_1}^{w_5-1} O_{H_2}^{w_6} = w_5 O_{H_1}^{w_5} O_{H_1}^{-1} O_{H_2}^{w_6} = w_5 O_{H_1}^{-1} v_{out}$$

$$\frac{\partial O_{H_1}}{\partial v_{H_1}} = \frac{1}{v_{H_1}}*O_{H_1}*\log_{10}(O_{H_1})*(1 - \log_{10}(O_{H_1}))$$

$$\frac{\partial v_{H_1}}{\partial w_1} = v_{H_1}\log(v_{H_1})$$

After finding the partial derivatives of the weighted error, the weightings vector will be updated as follows:

$$w_{i,n+1} = w_{i,n} - \eta \frac{\partial E_{rr}}{\partial w_{i,n}}$$

Figure 9D:
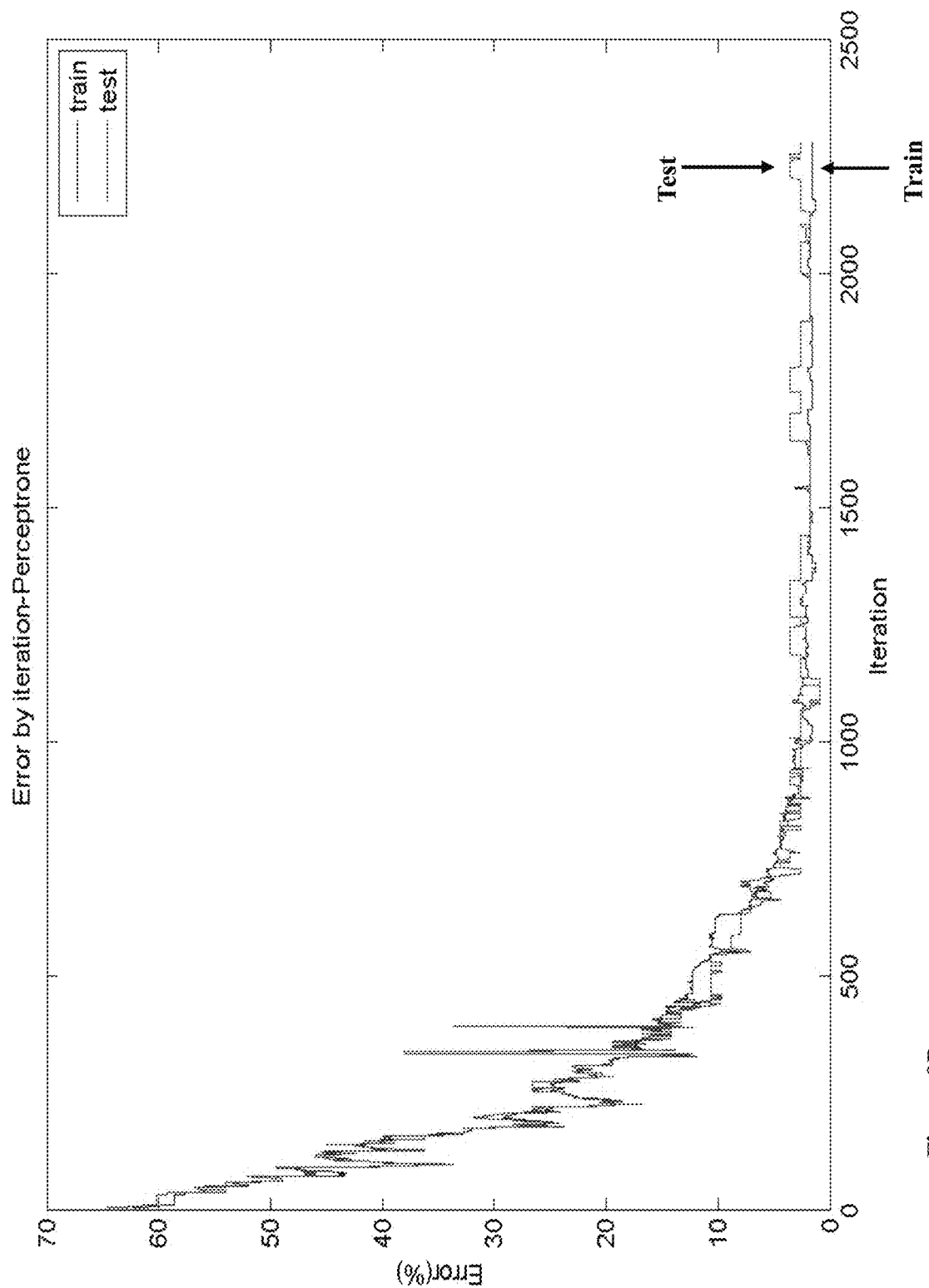
Figure 9E:
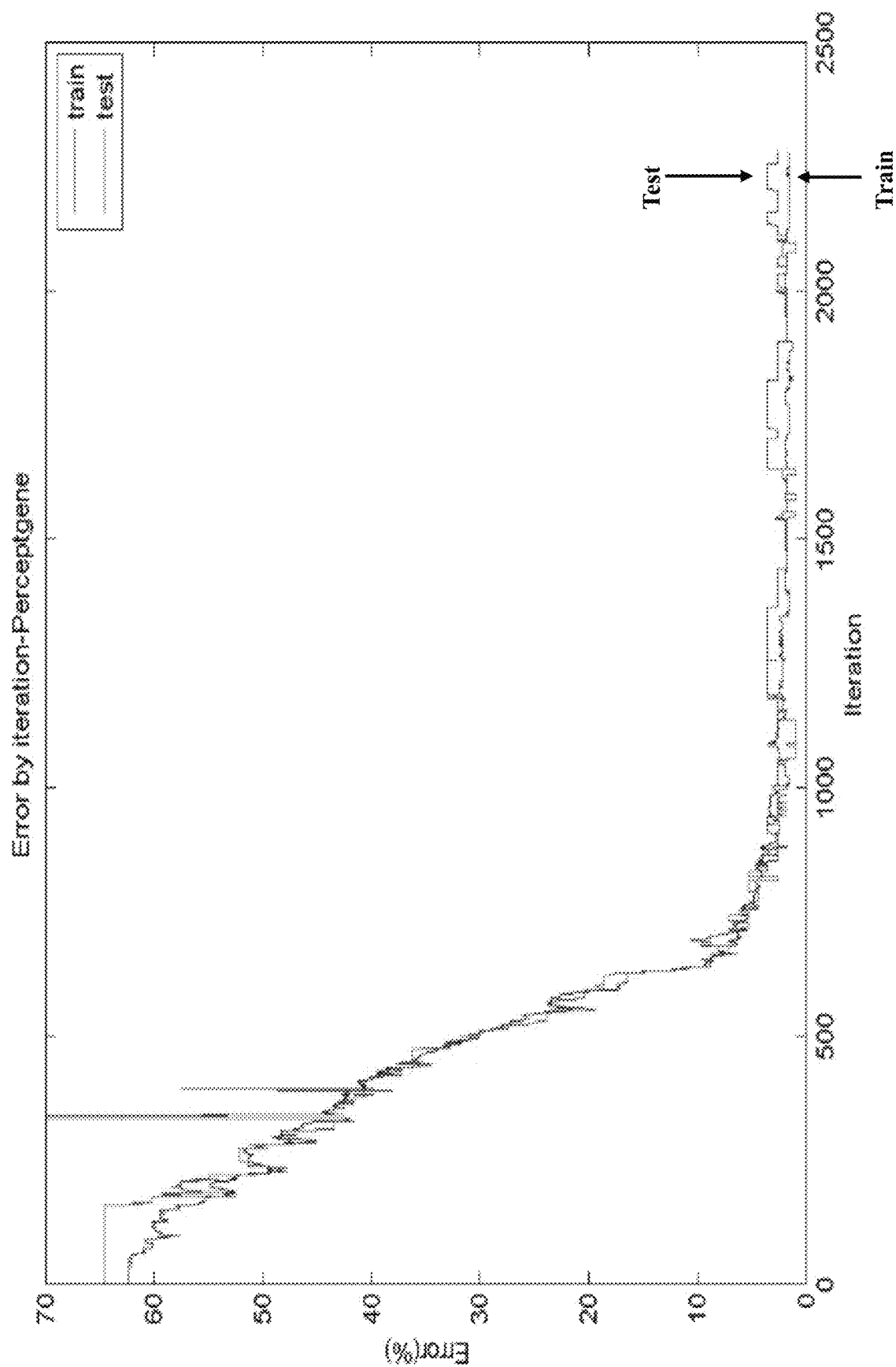
Figure 9F:
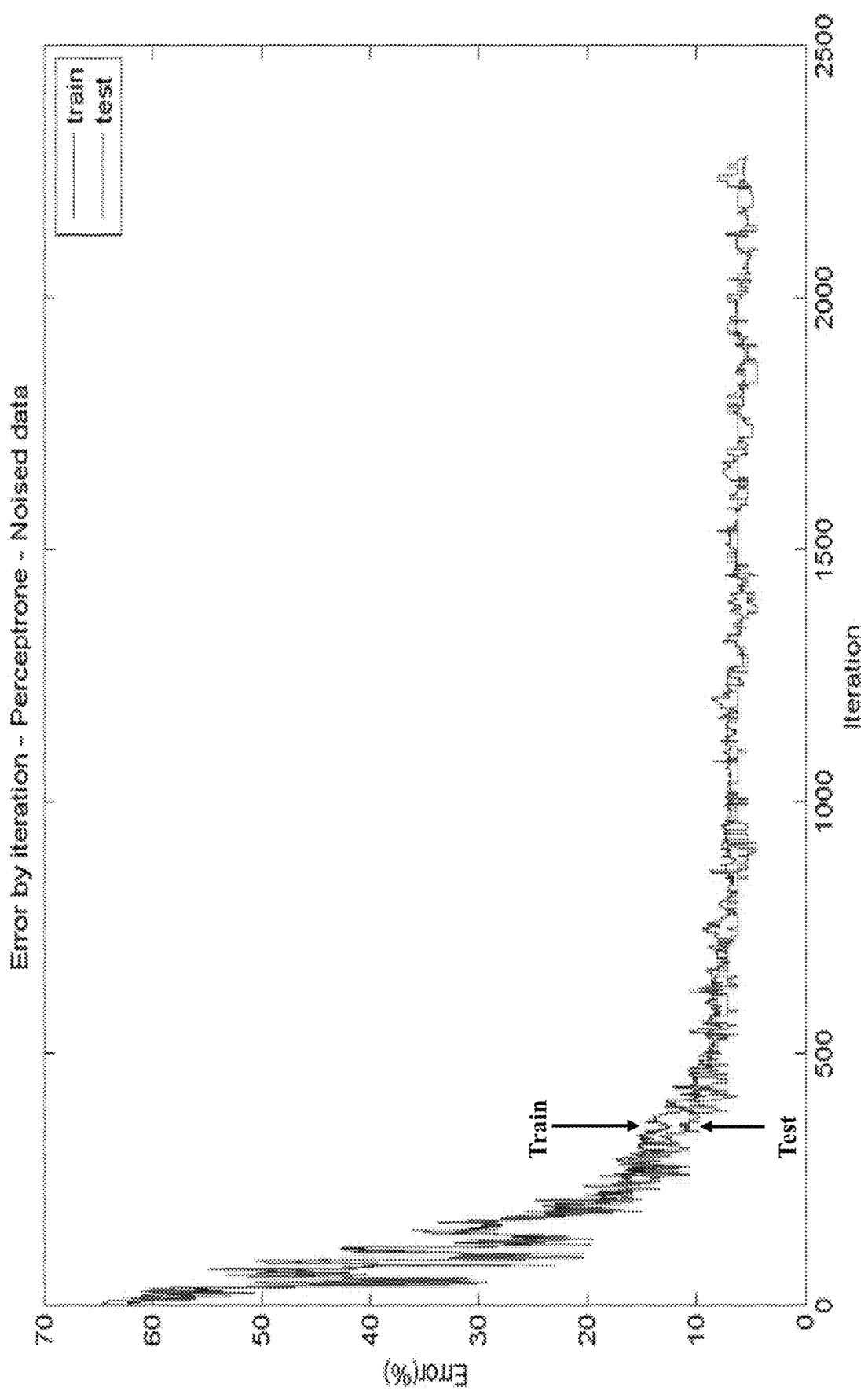
Figure 9G:
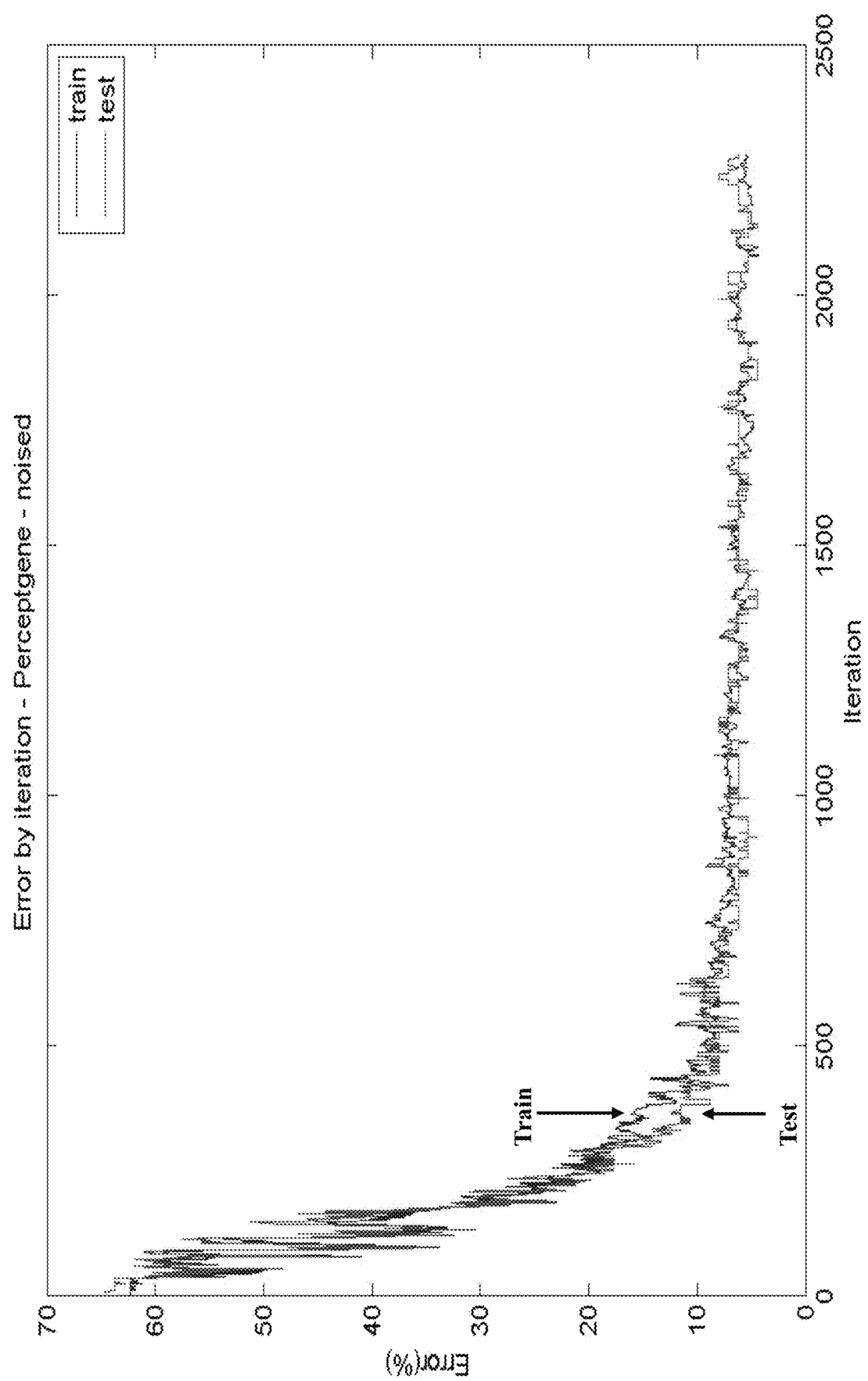

The results of running both algorithms—perceptron and perceptgene—on the training set (using a training rate of n=0.5 and 10 neural cells in the intermediate layer) are given in FIGS. 9D-9G. FIGS. 9D-9E illustrate the error rate as a function of iteration number for perceptron and perceptgene, respectively. FIG. 9F-9G illustrate the error rate as a function of iteration number for perceptron and perceptgene, respectively, when noise is added. As can be seen, the perceptgene network reaches error rates which are as low as those of perceptron. In addition, both algorithms do not show significant effect when noise is added. Accordingly, it may be concluded that a perceptgene-based neural network may reach at least the performance levels of a perceptron-based network.

Figure 10:
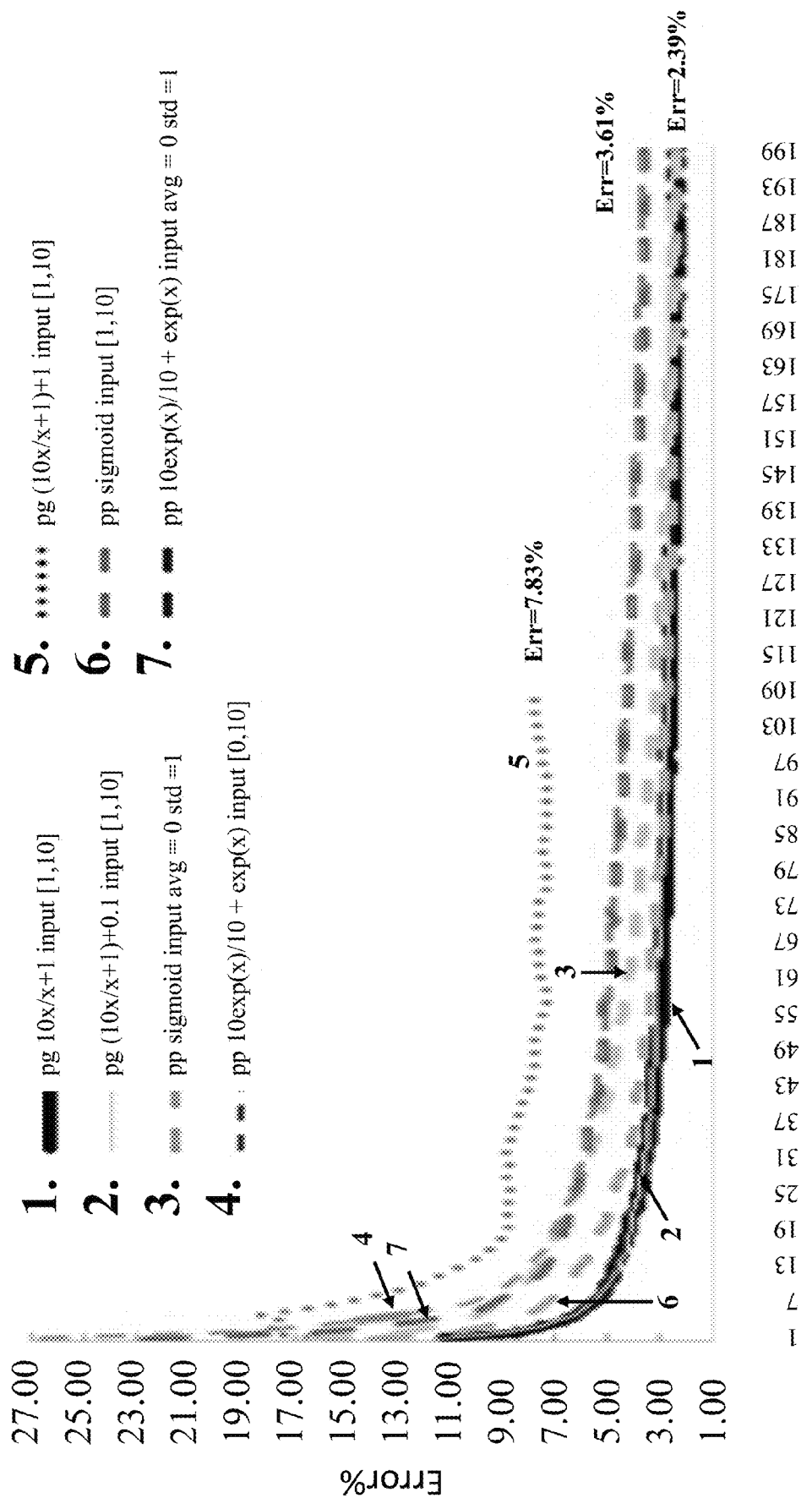
FIG. 10 A line graph showing comparative experimental results of pg and pp MINIST test results 60000 train 10000 test batch 100 learning rate 0.01.

In another experiment, the algorithm of the present invention—perceptgene—was tested against a perceptron-based algorithm using the Modified National Institute of Standards and Technology (MNIST) database, based on a 400-300-10 configuration, a learning rate of 0.1 and 1000 iterations. The results are presented in FIG. 10 and in table 2 below:

TABLE 2

Learning rate 0.001 pg/0.01 pp (batch size = 1) 700X300X10

| [1, 10] | 10 exp(x)/1 + exp(x) Perceptron | | 10 x/1 + x Perceptgene | |
|---|---|---|---|---|
| | Accuracy | Iterations | Accuracy | Iterations |
| 100 | — | 10 | 60.2% | 10 |
| 500 | 37.8% | | 83.7% | |
| 1000 | 43.9% | | 88.3% | |
| 5000 | 83.4% | | 93.9% | |

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object-oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a hardware processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowcharts and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the description and claims of the application, each of the words "comprise" "include" and "have", and forms thereof, are not necessarily limited to members in a list with which the words may be associated. In addition, where there are inconsistencies between this application and any document incorporated by reference, it is hereby intended that the present application controls.

What is claimed is:

1. An analog signal processing electrical circuit comprising:
   two or more analog, power-law function circuits, configured to produce at least two respective power-law signals, each representing expression of one of at least two cooperative biological inputs;
   an analog multiplication circuit, configured to produce, based on said power-law signals, a multiplication signal representing binding of the at least two biological inputs to a promoter, wherein said promoter is operably linked to a nucleic acid sequence encoding an output molecule; and
   an analog log-linear activation circuit, configured to produce, based on said multiplication signal, an activation signal representing transcription of the output molecule.

2. The analog signal processing circuit of claim 1, wherein said promoter is a hybrid promoter comprising at least two regulator binding sites.

3. The analog signal processing circuit of claim 2, wherein
   a. at least one of said at least two regulator binding sites binds an activator and at least one of said at least two regulator binding sites binds a repressor;
   b. said at least two inputs bind to said at least two regulator binding sites, or wherein said at least two inputs bind to at least two regulators that bind to said at least two regulator binding sites; or
   c. said at least two regulatory bindings sites are a LuxR binding site and a LacI binding site, optionally wherein said at least two inputs are acyl-homoserine lactone (AHL) and isopropyl β-d-thiogalactopyranoside (IPTG).

4. The analog signal processing circuit of claim 1, wherein the analog multiplication circuit is configured to produce, based on said power-law signals, at least one of:
   a. a multiplication signal representing binding of the at least two biological inputs to a second promoter, operably linked to a nucleic acid sequence encoding at least one of said cooperative inputs, wherein said second promoter comprises a binding site for said at least one of said cooperative inputs, optionally wherein said binding site in said second promoter comprises a modification that alters a binding affinity of said at least one cooperative input to said binding site relative to a binding affinity of said at least one cooperative input to an unmodified binding site;
   b. a multiplication signal representing binding of the at least two biological inputs to a third promoter operably linking to a nucleic acid sequence encoding a second output molecule, wherein said third promoter is responsive to said first output molecule, optionally wherein said third promoter comprises a pBAD promoter, and said first output molecule is araC protein.

5. The analog signal processing circuit of claim 4, wherein the activation signal represents at least one of:
   a regulatory sequence that regulates translation of said first output molecule and is located between said first promoter and said nucleic acid sequence encoding said first output molecule; optionally wherein said regulatory sequence is a riboswitch responsive to theophylline; and
   a regulatory sequence that regulates translation of said second output molecule and is located between said third promoter and said nucleic acid sequence encoding said second output molecule, optionally wherein said regulatory sequence is a riboswitch responsive to theophylline.

6. The analog signal processing circuit of claim 1, wherein
   a. a binding affinity to said first promoter of said at least two inputs, or said at least two regulators bound to said inputs, is tunable;
   b. said at least two cooperative inputs are at least two factors that share a common binding site and wherein said first promoter comprises said common binding site, optionally wherein said at least two factors that share a common binding site are a Sigma factor and an anti-Sigma factor; or
   c. said analog signal processing circuit further comprises said at least two factors that share a common binding site, or wherein said at least two cooperative inputs are Cas9 and a small guide RNA (sgRNA), optionally wherein said tunability of said Cas9 and said sgRNA is determined by mutating said sgRNA sequence to alter a binding affinity of said Cas9 to said sgRNA.

7. The analog signal processing circuit of claim 1, wherein said first promoter is responsive to a protein or protein complex consisting of more than one subunit, and wherein said at least two cooperative inputs are at least two of said subunits; wherein said protein consisting of more than one subunit is selected from:
   a. T7 RNA polymerase and said at least two cooperative inputs are an alpha-fragment subunit of T7 RNA polymerase, a sigma-fragment subunit of T7 RNA polymerase and a beta-core fragment subunit of T7 RNA polymerase, optionally further wherein the analog signal processing circuit further comprises a nucleic acid sequence coding for said alpha-fragment subunit, a nucleic acid sequence coding for said sigma-fragment subunit and a nucleic acid sequence coding for said beta-core fragment subunit, wherein said nucleic acid sequences coding for said T7 RNA polymerase subunits are operably linked to at least one promoter and optionally wherein said nucleic acid sequences coding for said T7 RNA polymerase subunits are operably linked to a plurality of promoters, wherein all three nucleic acid sequences are not linked to the same promoter and wherein the cooperativity of the inputs is determined by the binding affinities of said plurality of promoters; and
   b. Cas9.

8. The analog signal processing circuit of claim 1, wherein said first promoter is operably linked to a nucleic acid sequence encoding a first output molecule, and wherein the analog multiplication circuit is configured to produce, based on said power-law signals, a multiplication signal representing binding of the at least two biological inputs to a fourth promoter that transcribes in a direction opposite to a transcriptional direction of said first promoter, and wherein binding of at least one of said at least two cooperative inputs to said fourth promoter interferes with transcription from said first promoter.

9. A method for converting an analog signal into a digital output, comprising contacting the analog signal processing circuit of claim 1, with said at least two inputs and detecting said first output molecule, said second output molecule, or both thereby converting an analog signal into a digital output.

10. The method of claim 9, wherein said detecting comprises quantification of said output molecule.

11. The method of claim 9, wherein said digital output is either a positive or a negative output optionally wherein said method further comprises tuning a threshold for converting said analog input into a positive digital output wherein said tuning comprises at least one of:

i. tuning expression of at least one of said at least two regulators;
ii. tuning a binding efficiency of at least one of said at least two inputs to a binding site;
iii. tuning a binding efficiency of at least one of said at least two regulators to a binding site;
iv. adding a molecule that binds to said regulatory sequence, wherein said molecule that binds said regulatory sequence is theophylline; and
V. adding a molecule that binds to said first output molecule and alters binding of said first output molecule to said third promoter, wherein said molecule that binds to said first output molecule is arabinose.

12. The analog signal processing circuit of claim 1, wherein said two or more power-law function circuits are further configured to tune the respective power-law signals, to reflect the cooperativity of said at least two biological inputs.

* * * * *